(12) United States Patent
Desmadryl et al.

(10) Patent No.: US 10,195,195 B2
(45) Date of Patent: *Feb. 5, 2019

(54) SELECTIVE HISTAMINE H4 RECEPTOR ANTAGONISTS FOR THE TREATMENT OF VESTIBULAR DISORDERS

(71) Applicant: INSERM (Institut National de la Sante de la Recherche Medicale), Paris (FR)

(72) Inventors: Gilles Desmadryl, Montpellier (FR); Christian Chabbert, Montpellier (FR)

(73) Assignee: INSERM (INSTITUT NATIONAL DE LA SANTE ET DE LA RECHERCHE MEDICALE), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/345,570

(22) Filed: Nov. 8, 2016

(65) Prior Publication Data
US 2017/0056397 A1  Mar. 2, 2017

Related U.S. Application Data

(63) Continuation of application No. 13/141,652, filed as application No. PCT/EP2009/067897 on Dec. 23, 2009, now Pat. No. 9,526,725.

(30) Foreign Application Priority Data

Dec. 24, 2008 (EP) .................................. 08306013

(51) Int. Cl.
A61K 31/496 (2006.01)
A61K 9/00 (2006.01)

(52) U.S. Cl.
CPC .......... *A61K 31/496* (2013.01); *A61K 9/0046* (2013.01)

(58) Field of Classification Search
CPC ........................ A61K 31/496; A61K 31/0046
See application file for complete search history.

(56) References Cited

U.S. PATENT DOCUMENTS

| | | | |
|---|---|---|---|
| 6,093,417 A | 7/2000 | Petrus | 424/437 |
| 6,803,362 B2 | 10/2004 | Carruthers et al. | 514/183 |
| 8,431,580 B2 * | 4/2013 | Carceller Gonzalez | C07D 403/04 514/256 |
| 2004/0048878 A1 | 3/2004 | Cai et al. | 514/254.08 |
| 2004/0058934 A1 | 3/2004 | Carruthers et al. | 514/252.16 |
| 2004/0105856 A1 | 6/2004 | Thurmond et al. | 424/143.1 |
| 2004/0127395 A1 | 7/2004 | Desai et al. | 514/1 |
| 2004/0132715 A1 | 7/2004 | Dunford et al. | 514/211.15 |
| 2005/0070527 A1 | 3/2005 | Edwards et al. | 514/218 |
| 2005/0070550 A1 | 3/2005 | Arienti et al. | 514/253.09 |
| 2005/0261309 A1 | 11/2005 | Buzard et al. | 514/253.09 |
| 2007/0238771 A1 | 10/2007 | Edwards et al. | 514/394 |
| 2008/0188452 A1 | 8/2008 | Altenbach et al. | 514/210.16 |
| 2008/0261946 A1 | 10/2008 | Dyke et al. | 514/210.21 |
| 2008/0269239 A1 | 10/2008 | Harris et al. | 514/252.16 |
| 2009/0069343 A1 | 3/2009 | Dunford et al. | 514/254.08 |
| 2009/0275748 A1 | 11/2009 | Edwards et al. | 540/575 |
| 2012/0015953 A1 | 1/2012 | Beauregard et al. | 514/250 |

FOREIGN PATENT DOCUMENTS

| | | |
|---|---|---|
| WO | WO 2002/072548 | 9/2002 |
| WO | WO 2004/021999 | 3/2004 |
| WO | WO 2005/014556 | 2/2005 |
| WO | WO 2005/014579 | 2/2005 |
| WO | WO 2007/038949 | 9/2005 |
| WO | WO 2006/050965 | 5/2006 |
| WO | WO 2005/054239 | 6/2006 |
| WO | WO 2006/056848 | 6/2006 |
| WO | WO 2007/031529 | 3/2007 |
| WO | WO 2007/039467 | 4/2007 |
| WO | WO 2007/072163 | 6/2007 |
| WO | WO 2007/090852 | 8/2007 |
| WO | WO 2007/090853 | 8/2007 |
| WO | WO 2007/090854 | 8/2007 |
| WO | WO 2007/117399 | 10/2007 |
| WO | WO 2007/120690 | 10/2007 |
| WO | WO 2008/003702 | 1/2008 |
| WO | WO 2008/008359 | 1/2008 |
| WO | WO 2008/031556 | 3/2008 |
| WO | WO 2008/060767 | 5/2008 |
| WO | WO 2008/074445 | 6/2008 |
| WO | WO 2008/100565 | 8/2008 |
| WO | WO 2008/122378 | 10/2008 |
| WO | WO 2009/038673 | 3/2009 |
| WO | WO 2009/047255 | 4/2009 |
| WO | WO 2009/056551 | 5/2009 |
| WO | WO 2009/068512 | 6/2009 |
| WO | WO 2009/071625 | 6/2009 |
| WO | WO 2009/077608 | 6/2009 |

(Continued)

OTHER PUBLICATIONS

California Ear Institute (http://www.californiaearinstitute.com /ear-disorders-vestibular-neuritis-bay-area.php, May 2008), S.*
hupert (Vestibular Disorders, Feb. 15, 2006).*
Strupp et al. (J Neurol, 2011, 258, 1207-1222).*
Brandt et al., "Medical treatment of vestibular disorders". Expert Opin Pharmacother. Jul. 2009;10(10):1537-48.
Leurs et al., "Molecular and biochemical pharmacology of the histamine H4 receptor". Br J Pharmacol. May 2009;157(1):14-23.
Shupak et al., "Prednisone treatment for vestibular neuritis". Otol Neurotol. Apr. 2008;29(3):368-74.
Arrang JM "Actions of betahistine at histamine receptors in the brain." Eur J Pharmacol. Apr. 23, 1985; vol. 111 No. 1 pp. 73-84.
Baloh RW Differentiating between peripheral and central causes of vertigo. Otolaryngol Head Neck Surg. Jul. 1998;119(1):55-9.
Baloh RW Vertigo. Lancet. Dec. 5, 1998;352(9143):1841-6.

(Continued)

*Primary Examiner* — Umamaheswari Ramachandran
(74) *Attorney, Agent, or Firm* — Norton Rose Fulbright US LLP

(57) ABSTRACT

The invention relates to Histamine H4 receptor antagonists or inhibitors of Histamine H4 receptor gene expression for the treatment and/or the prevention of vestibular disorders.

5 Claims, 4 Drawing Sheets

(56) References Cited

FOREIGN PATENT DOCUMENTS

Figure 1:
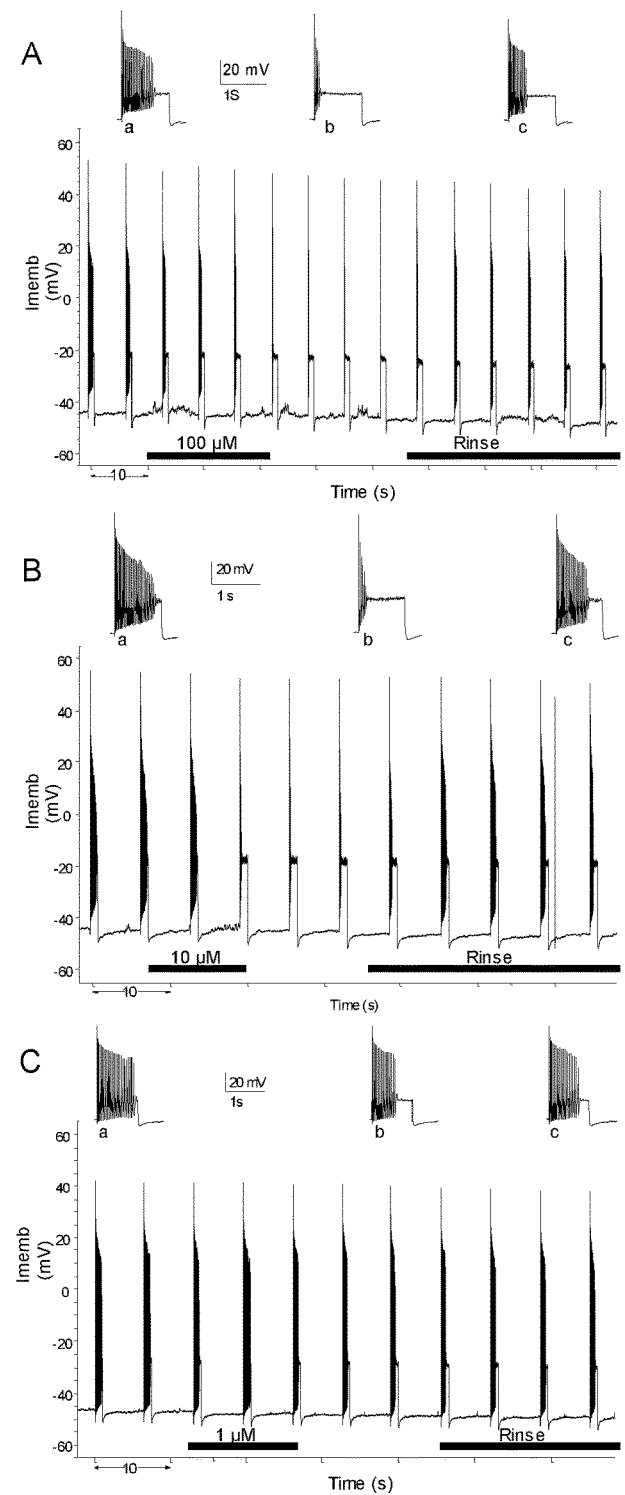

| WO | WO 2009/079001 | | 6/2009 |
|---|---|---|---|
| WO | WO 2009/080721 | | 6/2009 |
| WO | WO 2009/080721 | * | 7/2009 |
| WO | WO 2009/107767 | | 9/2009 |
| WO | WO 2009/114575 | | 9/2009 |
| WO | WO 2009/115496 | | 9/2009 |
| WO | WO 2009/123967 | | 10/2009 |
| WO | WO 2009/134726 | | 11/2009 |
| WO | WO 2009/137492 | | 11/2009 |

OTHER PUBLICATIONS

Botta et al., "Effects of betahistine on vestibular receptors of the frog," *Acta. Otoaryngol. (Stockh).*, 118:519-523, 1998.
Brummelkamp TR, et al. A system for stable expression of short interfering RNAs in mammalian cells. Science. Apr. 19, 2002; vol. 296 No. 5567 pp. 550-553.
Carter P, et al. Improved oligonucleotide site-directed mutagenesis using M13 vectors. Nucleic Acids Res. Jun. 25, 1985;vol. 13 No. 12 pp. 4431-4443.
Chavez et al., "Histamine ($H_3$) receptors modulate the excitatory amino acid receptor response of the vestibular afferents," *Brain Research*, 1064:1-9, 2005.
Colas P, et al. "Genetic selection of peptide aptamers that recognize and inhibit cyclin-dependent kinase 2." Nature. Apr. 11, 1996; vol. 380 No. 6574 pp. 548-550.
Coruzzi et al. "Antiinflamatory and antinociceptive effects of the selective histamine H4-receptor antagonists JNJ7777120 and VUF6002 in a rat model of carrageenan-induced acut inflammation" *European J of Pharmacology*, 563: 240-244. 2007.
Cote RJ, et al. Generation of human monoclonal antibodies reactive with cellular antigens. Proc Natl Acad Sci U S A. Apr. 1983; vol. 80 No. 7 pp. 2026-2030.
Cowart et al., "Rotationally constrained 2,4-diamino-5,6-disubstituted pyrimidines: a new class of histamine H4 receptor antagonists with improved druglikeness and in vivo efficacy in pain and inflammation models," *J. Med. Chem.*, 51:6547-6557, 2008.
Desmadryl et al. Histamine H4 receptor antagonists as potent modulators of mammalian vestibular primary neuron excitability May 2012 Br. J. Pharm vol. 167 No. 4 pp. 905-916.
Dijkstra d et al "Human Inflammatory Dendritic Epidermal Cells Express a Functional Histamine H4 Receptor" J Invest Dermatol. Jul. 2008; vol. 128 No. 7 pp. 1695-1703.
Dorwald, *Side Reactions in Organic Synthesis: A Guide to Successful Synthesis Design.* Wiley-VCH. Weinheim. 2005, p. 1-4.
Elbashir SM, et al. Duplexes of 21-nucleotide RNAs mediate RNA interference in cultured mammalian cells. Nature. May 24, 2001; vol. 411 No. 6836 pp. 494-498.
Ghabou et al., "Compared pharmacology of human histamine H3 and H4 receptors: structure-activity relationships of histamine derivatives," *British Journal of Pharmacology*, 147:744-754, 2006.
Godot et al., "H4 histamine receptor mediates optimal migration of mast cell precursors to CXCL12," *J. Allergy Clin. Immunol*, 120:827-34, 2007.
Hannon, GJ. "RNA interference" Jul. 11, 2002; vol. 418 No. 6894 pp. 244-51.
Hotson et al, "Acute Vestibular Syndrome" NEJM Sep. 1998, vol. 339 No. 10 pp. 680-685.
Housley et al., "Histamine and related substances influence neurotransmission in the semicircular canal," *Hearing Research*, 35:87-98, 1988.
ISR WO2010/072829 (Apr. 9, 2010).
Jablonowski et al., "The first potent and selective non-imidazole human histamine $H_4$ receptor antagonists," *J. Med. Chem.*, 46(19):3957-3960, 2003.
Jayasena S.D. "Aptamers: an emerging class of molecules that rival antibodies in diagnostics." Clin Chem. Sep. 1999; vol. 45 No. 9 pp. 1628-1650.
Kiss et al. "H4 receptor ligands and their potential therapeutic applications: an update," *Expert Opinion*, 22(3): 205-221 2012.
Kiss et al. "Histamine H4 receptor ligands and their potential therapeutic applications," *Expert Opinion*, 19(2): 119-135. 2009.
Kohler and Milstein "Continuous cultures of fused cells secreting antibody of predefined specificity." Nature Aug. 7, 1975; vol. 256 No. 5517 pp. 495-497.
Lacour et al. "Histamine and Betahistamine in the treatment of vertigo" *CNS Drugs.* 15(11): 853-870. 2001.
Lim et al., "Evaluation of histamine H1-, H2-, and H3-receptor ligands at the human histamine H4 receptor: identification of 4-methylhistamine as the first potent and selective H4 receptor agonist," *The Journal of Pharmacology and Experimental Therapy*, 314(3):1310-1321, 2005.
Ling et al. "Histamine $H_4$ receptor mediates eosinophil chemotaxis with cell shape change and adhesion molecule upregulation" *British Journal of Pharmacology*, 142: 149-163. 2004.
Liu C "Cloning and pharmacological characterization of a fourth histamine receptor (H(4)) expressed in bone marrow" Mol Pharmacol Mar. 2001; vol. 59 No. 3 pp. 420-426.
Liu C "Comparison of human, mouse, rat, and guinea pig histamine H4 receptors reveals substantial pharmacological species variation" J Pharmacol Exp Ther Oct. 2001; vol. 299 No. 1 pp. 121-130.
Liu et al., "cis-4-(Piperazin-1-yl)-5,6,7a,8,9,10,11,11a-octahydrobenzofuro[2,3-h]quinazolin-2-amine (A-987306), a new histamine H4R antagonist that blocks pain responses against carrageenan-induced hyperalgesia," *J. Med Chem.*, 51(22):7094-7098, 2008.
Lovenberg TW "Cloning and functional expression of the human histamine H3 receptor" Mol Pharmacol Jun. 1999; vol. 55 No. 6 pp. 1101-1107.
Marzo "Intratympanic Therapy for Sensorineural Hearing Loss and Vertigo," Audiology Meeting, Chicago, Illinois, Jan. 24, 2002.
Mcmanus and SHARP "Gene silencing in mammals by small interfering RNAs" Nat Rev Genet Oct. 2002; vol. 3 No. 10 pp. 737-747.
Meniere's Syndrome, 2015 (http://my.clevelandclinic.orgiservices/head-neck!diseases-conditions/hic-treating-menieres- syndrome).
Parsons and Ganellin, "Histamine and its receptors," *British Journal of Pharmacology*, 147:S127-S135, 2006.
Piratello and Mattioli, "Thioperamide delays vestibular compensation in goldfish," *Neuroscience Letters*, 415:146-148, 2007.
Soto et al., "Betahistine produces post-synaptic inhibition of the excitability of the primary afferent neurons in the vestibular endorgans," *Acta. Otolargynol.*, Suppl. 545:19-24, 2001.
Stark, "Recent advances in the histamine $H_3/H_4$ receptor ligands," *Expert. Opin. Ther. Patents*, 13(6):851-865, 2003.
Terzioglu N Synthesis and structure-activity relationships of indole and benzimidazole piperazines as histamine H(4) receptor antagonists. Bioorg Med Chem Lett. Nov. 1, 2004;14(21):5251-6.
Thurmond et al., "A potent and selective histamine $H_4$ receptor antagonist with anti-inflammatory properties," *The Journal of Pharmacology and Experimental Therapeutics*, 309(1):404-413, 2004.
Tian et al, "Advances in Ligands of Histamine H4 Receptor" Journal of Anhui Health Vocational & Technical College, 2008 vol. 7 No. 2 pp. 80-81 (Chinese + English version).
Tighilet et al., "Dose- and duration-dependent effects of betahistine dihydrochloride treatment on histamine turnover in the cat," *European Journal of Pharmacology*, 523:54-63, 2005.
Tighilet et al., "Histaminergic ligands improve vestibular compensation in the cat: Behavioural, neurochemical and molecular evidence," *European Journal of Pharmacology*, 568:149-163, 2007.
Tomodoa et al., "Effect of histamine on intracellular $Ca^{2+}$ concentration in guinea pig isolated vestibular hair cells," *Ada. Otolaryngol. (Stockh.)*, Suppl. 528:37-40, 1997.
Tuerk C. and Gold L "Systematic evolution of ligands by exponential enrichment: RNA ligands to bacteriophage T4 DNA polymerase." Science. Aug. 3, 1990; vol. 249 No. 4968 pp. 505-510.
Tuschl, T. et al. "Targeted mRNA degradation by double-stranded RNA in vitro." Genes Dev. Dec. 1999; vol. 13 No. 24 pp. 3191-3197.

(56) References Cited

OTHER PUBLICATIONS

Van Cauwenberge and De Moor, "Physiopathology of $H_3$-receptors and pharmacology of betahistine," *Acta. Aotlaryhgol.* (*Stockh.*), Suppl. 526:43-46, 1997.
Venable JD "Preparation and biological evaluation of indole, benzimidazole, and thienopyrrole piperazine carboxamides: potent human histamine h(4) antagonists." J Med Chem Dec. 2005; vol. 48 No. 26 pp. 8289-8298.
Wells JA "Cassette mutagenesis: an efficient method for generation of multiple mutations at defined sites" Gene 1985; vol. 34 No. 2-3 pp. 315-323.
Yabe et al. "Medial vestibular nucleas in the guinea-pig: histaminergic receptors II. An in vivo study" *Experimental Brain Research*. 93: 249-258. 1993.
Zhang M "The histamine H(4) receptor: a novel modulator of inflammatory and immune disorders" Phamacol Ther Mar. 2007; vol. 113 No. 3 pp. 594-606.
Zoller MJ , Smith M "Oligonucleotide-directed mutagenesis using M13-derived vectors: an efficient and general procedure for the production of point mutations in any fragment of DNA" Nucleic Acids Res. Oct. 1982 vol. 10 No. 20 pp. 6487-6500.

\* cited by examiner

SELECTIVE HISTAMINE H4 RECEPTOR ANTAGONISTS FOR THE TREATMENT OF VESTIBULAR DISORDERS

CROSS-REFERENCE TO RELATED APPLICATIONS

This application is a continuation of U.S. application Ser. No. 13/141,652 filed Sep. 9, 2011, which is a national phase application under 35 U.S.C. § 371 of International Application No. PCT/EP2009/067897 filed 23 Dec. 2009, which claims priority to European Application No. 08306013.7 filed 24 Dec. 2008. The entire text of each of the above-referenced disclosures is specifically incorporated herein by reference without disclaimer.

FIELD OF THE INVENTION

The invention relates to selective Histamine H4 receptor antagonists or inhibitors of Histamine H4 receptor gene expression for the treatment and/or the prevention of vestibular disorders.

BACKGROUND OF THE INVENTION

Vestibular (inner ear) disorders can cause dizziness, vertigo, imbalance, hearing changes, nausea, fatigue, anxiety, difficulty concentrating, and other symptoms, with potentially devastating effects on a person's day-to-day functioning, ability to work, relationships with family and friends, and quality of life.

Anti-histaminergic compounds are widely used as treatments against vestibular disorders, like vertigos. Histaminergic agonists and antagonists act on the vestibular system both peripherally and centrally, and could interfere with the recovery process after peripheral vestibular lesion (Lacour and Sterkers, 2001). Histamine receptor family comprises four subtypes: H1 and H2 receptor discovered in 1966, H3 receptor discovered in 1983 and H4 receptor identified in 2000. The H4 receptor was identified on the basis of its homology with the H3 receptor (31% at protein level and 54% within the transmembrane membrane). Over the four histamine receptors (HR1 to HR4) HR3 appeared to regulate the vestibular inputs (Chavez 2005). In the field of the histaminergic treatment of vertigo, betahistine (BH) is one of the broad range of antivertiginous compound. The facilitator action of BH has been described in central vestibular compensation (Lacour and Sterkers, 2001; Tighilet et al. 2005), but its effects on peripheral vestibular receptors has only been reported in lower vertebrates (Housley et al. 1988; Tomoda et al. 1997; Botta et al. 1998; Soto et al. 2001; Chavez et al. 2005). BH has been reported to present a complex function as an agonist of H1 histaminic receptor, and as an antagonist of the H3 receptor (Arrang et al. 1985). In the peripheral vestibular receptors isolated from axolotl, BH inhibits the afferent discharge with an IC50 of 800 μM and a maximum effect around 10 mM (Chavez 2005). These studies concluded that histamine H3 receptor was the main target of BH (Van Cauwenberge and De Moor 1997; Soto 2001; Chavez 2005). A recent study realized in cultured rat vestibular neurons, maintained 7 days in vitro, reveals that the application of BH induced a reversible depolarisation of the neuron's membrane and inhibited the evoked discharge without affecting the intrinsic properties of the action potentials.

However, no investigation on Histamine H4 receptor has been made on vestibular disorders.

SUMMARY OF THE INVENTION

The present invention relates to selective Histamine H4 receptor antagonists for the treatment and/or the prevention of vestibular disorders. The present invention also relates to selective Histamine H4 receptor antagonists for use in the treatment and/or the prevention of vestibular disorders.

The present invention also relates to inhibitors of Histamine H4 receptor gene expression for the treatment and/or the prevention of vestibular disorders.

DETAILED DESCRIPTION OF THE INVENTION

Definitions:

The term "Histamine H4 receptor" has its general meaning in the art. The term may include naturally occurring Histamine H4 receptors and variants and modified forms thereof. The Histamine H4 receptor can be from any source, but typically is a mammalian (e.g., human and non-human primate) Histamine H4 receptor, particularly a human Histamine H4 receptor. Sequences for Histamine H4 receptor have been published under the references NM_021624 (*Homo sapiens*), NM_153087 (*Mus musculus*) and NM_131909 (*Rattus norvegicus*).

An "inhibitor of gene expression" refers to a natural or synthetic compound that has a biological effect to inhibit or significantly reduce the expression of a gene. Consequently an "inhibitor of Histamine H4 receptor gene expression" refers to a natural or synthetic compound that has a biological effect to inhibit or significantly reduce the expression of the gene encoding for the Histamine H4 receptor.

By "receptor antagonist" is meant a natural or synthetic compound that has a biological effect opposite to that of a receptor agonist. The term is used indifferently to denote a "true" antagonist and an inverse agonist of a receptor. A "true" receptor antagonist is a compound which binds the receptor and blocks the biological activation of the receptor, and thereby the action of the receptor agonist, for example, by competing with the agonist for said receptor. An inverse agonist is a compound which binds to the same receptor as the agonist but exerts the opposite effect. Inverse agonists have the ability to decrease the constitutive level of receptor activation in the absence of an agonist.

The term "Histamine H4 receptor antagonist" includes any chemical entity that, upon administration to a patient, results in inhibition or down-regulation of a biological activity associated with activation of the Histamine H4 receptor in the patient, including any of the downstream biological effects otherwise resulting from the binding to Histamine H4 receptor of its natural ligand. Such Histamine H4 receptor antagonists include any agent that can block Histamine H4 receptor activation or any of the downstream biological effects of Histamine H4 receptor activation. For example, such Histamine H4 receptor antagonists can act by occupying the ligand binding site or a portion thereof of the Histamine H4 receptor, thereby making the receptor inaccessible to its natural ligand so that its normal biological activity is prevented or reduced.

In the context of the present invention, Histamine H4 receptor antagonists are selective for the Histamine H4 receptor as compared with the other histamine receptors, such as histamine H1 receptor, histamine H2 receptor, and histamine H3 receptor. By "selective" it is meant that the affinity of the antagonist for the human Histamine H4 receptor is at least 10-fold, preferably 25-fold, more preferably 100-fold, still preferably 500-fold higher than the affinity for the other human histamine receptor (H1, H2 and H3).

The affinity of an antagonist for Histamine H4 receptor may be quantified by measuring the activity of Histamine H4 receptor in the presence a range of concentrations of said antagonist in order to establish a dose-response curve. From that dose response curve, an $IC_{50}$ value may be deduced which represents the concentration of antagonist necessary to inhibit 50% of the response to an agonist in defined concentration. The $IC_{50}$ value may be readily determined by the one skilled in the art by fitting the dose-response plots with a dose-response equation as described by De Lean et al. (1979). $IC_{50}$ values can be converted into affinity constant (Ki) using the assumptions of Cheng and Prusoff (1973).

Accordingly, a selective Histamine H4 receptor antagonist is a compound for which at least one of the ratios (i) $K_i$ H3:$K_i$ H4, and (ii) $IC_{50}$ H3: $IC_{50}$ H4, is above 10:1, preferably 25:1, more preferably 100:1, still preferably 1000:1.

The antagonistic activity of compounds towards the Histamine H4 receptors may be determined using various methods, such as those described in Thurmond R L et al. (2004) or Venable J D. et al. (2005).

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

As used herein, the term "subject" denotes a mammal, such as a rodent, a feline, a canine, and a primate. Preferably, a subject according to the invention is a human.

The term "vestibular disorders" refers to conditions characterized by dizziness, visual or gaze disturbances and balance impairment. Vestibular disorders could result from diverse damages or dysfunction of the inner ear, among them the acute and chronic syndromes. Examples of vestibular disorders that are contemplated by the invention include but are not limited to vertigo, benign paroxysmal vertigo, vestibular neuritis, spell of Ménière's disease, endolymphatic hydrops, perilymphatic fistula, head trauma with vestibular disorders, labyrinthine haemorrhage, chronic or acute labyrinthine infection, serous labyrinthine, barotraumatism, autoimmune inner ear disease, migraine with vestibular syndromes, vestibular syndromes after chirurgical treatments of middle ear, middle ear, endolymphatic sac or pontocerebellar angle, inner ear channelopathies, chronic Ménière disease, vestibular, schwannomas, presbyvestibulia, familial episodic vertigo and ataxia.

In its broadest meaning, the term "treating" or "treatment" refers to reversing, alleviating, inhibiting the progress of, or preventing the disorder or condition to which such term applies, or one or more symptoms of such disorder or condition.

In particular, "prevention" of vestibular disorders may refer to the administration of the compounds of the present invention prevent the symptoms of vestibular disorders.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Therapeutic Methods and Uses

The present invention provides methods and compositions (such as pharmaceutical compositions) for treating vestibular disorders or for use in treating vestibular disorders.

According to a first aspect, the invention relates to selective Histamine H4 receptor antagonists for treating vestibular disorders or for use in treating vestibular disorders.

In one embodiment, the selective Histamine H4 receptor antagonists may be low molecular weight antagonists, e. g. a small organic molecule.

According to one embodiment of the invention, a selective H4 receptor antagonist refers to a molecule that has an affinity for H4 receptor at least 10 fold, preferably 25 fold, preferably 50 fold, more preferably 100 fold, and even more preferably 500 fold higher than its affinity for any one of H1, H2 or H3 receptor.

According to another embodiment of the invention, a selective H4 receptor antagonist is a molecule for which one of the ratios Ki H3:Ki H4 and (ii) IC50 H3 : IC50 H4 is above 10:1, preferably 25:1, preferably 50:1, more preferably 100:1 and even more preferably between 500:1 to 1000:1.

The affinity for H4 receptor and others (H1, H2 and H3) receptors may be characterized by any conventional technique known in the art. For example, it can be determined by binding assays. Said assays use cells pellets from cells such as SK-N-MC or HEK293 T, cells transfected with human, rat or mouse H4, H3, H2 or H1 receptor (Lovenberg et al. 1999, Liu et al. 2001a,b, Thurmond et al. 2004). Cells can be homogenized in 50 mM Tris pH 7.5 containing 5 mM EDTA, and supernantants from an 800 g spin are collected and recentrifuged at 30 000 g for 30 min. Pellets are then homogenized in 50 mM Tris pH 7.5 containing 5 mM EDTA. For H4 competition binding studies, human, mouse or rat cells are incubated using different concentrations of [$^3$H] histamine (specific for each species, for example 10, 40 and 50 nM respectively), in the presence or absence of the molecule to be tested, for about 45 min at 25° C. The non-specific binding is defined using 100 µM unlabeled histamine or using $10^{-6}$ M of specific or selective H4 receptor antagonist such as JNJ-7777120 or JNJ-10191584. The Kd values for the human, mouse and rat H4 receptor were determined with this method to be 5, 42 and 178 nM respectively, and the Bmax values were determined to be 1.12, 1.7 and 0.68 pmol/mg protein, respectively. Similarly, the ligand used for the H3 receptor binding assays is for example [$^3$H]N-a-methyl histamine, and the non-specific binding is defined using 100 µM unlabeled histamine. The Kd value for human H3 receptor was determined with this method to be 1 nM and the Bmax value 2.13 pmol/mg protein. The ligand used for the H1 receptor binding was [$^3$H]pyrilamine and the non-specific activity is defined using 10 µM unlabeled diphenhydramine. The Kd value for human H1 receptor was determined with this method to be 1 nM and the Bmax value 2.68 pmol/mg protein. In these assays, the cells are typically incubated with different concentration of such as $10^{-11}$ to $10^{-4}$ M of molecule to be tested.

The person skilled in the art willing to verify or determine the antagonist activity of the molecule to be tested may use any method known in the art and for example a cell-based cAMP assay. Said assay use SK-n-MC cell lines transfected with H4, H3, H2 or H1 receptor and a reporter gene construct such as b-galactosidase under the control of cyclic AMP-responsive elements. Cells are plated overnight before the assay. Histamine is used as the agonist molecule. For determination of antagonist activity, molecules to be tested are added 10 min prior to the addition of agonist. Forskolin (5 µM final concentration) is added 10 min after the addition of histamine. Cells are then maintained at 37° C. for 6 hours, and then after washing lysed with about 25 µl of 0.1× assay buffer (10 mM sodium phosphate, pH 8, 0.2 mM MgSO$_4$ and 0.01 mM MnCl$_2$) and incubated at room temperature for 10 min. Cells are then incubated for 10 min with about 100 µl of 1× assay buffer containing 0.5% (v/v) Trition X-100 and 40 mM β-mercaptoethanol. Color can be developed using 25 µl of 1 mg/ml substrate solution such as chlorophenol red b-D-galactopyranoside, and quantified by measuring the absorbance at 570 nm. The data obtained for each concentration-response curve can be fitted to a sigmoidal curve to obtain the maximum response, Hill coefficient and EC$_{50}$.

Exemplary selective Histamine H4 antagonists that are contemplated by the invention include but are not limited to those described in U.S. Pat. No. 6,803,362; US Patent Application Publication Nos. 2004/0105856, 2004/0127395, 2004/0132715, 2004/0048878, 2004/0058934, 2005/0070527, 2005/0070550, 2005/0261309, 2007/0238771, 2008/0269239, 2008/0261946, 2008/0188452, 2009/275748, and International Patent Application Nos WO2005/054239, WO2005/014556, WO2007/031529, WO2007/072163, WO2007/090852, WO2007/117399, WO2007/120690, WO2008/074445, WO2008/008359, WO2008/031556, WO2008/100565, WO2008/003702, WO2009/134726, WO2009/115496, WO2009/114575, WO2009/080721, WO2009/077608, WO2009/071625, WO2009/068512, WO2009/056551, WO2009/038673, WO2009/077608, WO2009/079001 and WO2009/047255, which are incorporated herein by reference.

Other exemplary selective Histamine H4 antagonists that are contemplated by the invention include but are not limited to those described in Jablonowski J A et al. (2003), Venable J D. et al. (2005), Thurmond R L. et al. (2004), Herman D. et al. (2005) Robin L. et al. (2004), Cowart M D. et al. (2008) and Liu H. et al. (2008).

Typically, compounds that may be contemplated by the invention are 2-aminopyrimidine derivatives, such as described in WO2005/054239 or WO2005/014556, or quinazoline derivatives such as described in WO2008/003702.

In one embodiment of the invention, the selective H4 antagonist is selected among bicyclic heteroaryl-substituted imidazole compounds, such as the ones described in WO2009/079001 and WO2007/120690; thieno- and furo-pyrimidine compounds such as the ones described in WO2009/038673; 2-Aminopyrimidine compounds such as the ones described in WO2008/100565, WO2009077608, WO2009/068512, WO2005/054239, WO2008/031556, WO2008122378 and WO2005/014556; benzofuro- and benzothienopyrimidine compounds such as the ones described in WO2008/008359; Furo[3,2-d]pyrimidine derivatives such as the ones described in WO2009/056551 and WO2009/115496; 4-Amino-pyrimidine derivatives such as the ones described in WO2009/080721; amino pyrimidine compounds such as the ones described in WO2007/090852; enantiomers of amino pyrimidine compounds such as the ones described in WO2007/090853; azetidine amino pyrimidine compounds, such. as the ones described in WO2007/090854; pyrimidine compounds such as the ones described in WO2007/039467, WO2006/050965 and WO2007/072163; mequitazine, such as the ones described in WO2009/071625; substituted pyrimidine derivatives, particularly macrocyclic fused substituted pyrimidine derivatives, such as the ones described in WO2009/134726; macrocyclic spiro pyrimidine compounds, particularly tricyclic spiro pyrimidine compounds, such as the ones described in WO2009/114575; macrocyclic benzofused pyrimidine compounds, such as the ones described in WO2008/060767; heteroaryl-fused macrocylciv pyrimidine derivatives, particularly heteroaryl-fused macrocyclic 2,4-diaminopyrimidine compounds, such as the ones described in WO2009137492; 5,6,7,8-tetrahydroquinazolin-2-amine derivatives, such as the ones described in WO2009123967; octahydropyrrolo[3,4-c]pyrrole derivatives, such as the ones described in WO2006056848; tricyclic and heterotricyclic derivatives, such as the ones described in WO2008/074445; heterobicyclic compounds such as the ones described in WO2009047255; quinazolines and related heterocyclic compounds, such as the ones described in WO2008/003702; imidazole derivatives of piperidine, such as the ones described in WO2005/014579; bicyclic pyrimidine compound, such as the ones described in WO2009107767 (all references being incorporated by reference).

In a particular embodiment, the selective Histamine H4 antagonists are selected from those described in the international Patent Application WO2007/120690:(1H-Benzoimidazol-2-yl)-(4-methyl-piperazin-1-yl)-methanone; (1H-Benzoimidazol-2-yl)-(4-ethyl-piperazin-1-yl)-methanone; (1H-Benzoimidazol-2-yl)-(3-methyl-piperazin-1-yl)-methanone; (1H-Benzoimidazol-2-yl)-(4-methyl-[1,4]diazepan-1-yl)-methanone; 1H-Benzoimidazole-2-carboxylic acid (8-methyl-8-aza-bicyclo[3.2.1]oct-3-yl)-amide; (5-Chloro-1H-benzoimidazol-2-yl)-(4-methyl-piperazin-1-yl)-methanone; (5-Chloro-1H-benzoimidazol-2-yl)-piperazin-1-yl-methanone; (5-Chloro-1H-benzoimidazol-2-yl)-(3-methyl-piperazin-1-yl)-methanone; (5,6-Difluoro-1H-benzoimidazol-2-yl)-(4-methyl-piperazin-1-yl)-methanone; (5,6-Difluoro-1H-benzoimidazol-2-yl)-(4-ethyl-piperazin-1-yl)-methanone; (5,6-Difluoro-1H-benzoimidazol-2-yl)-(3-methyl-piperazin-1-yl)-methanone; (5,6-Difluoro-1H-benzoimidazol-2-yl)-(4-methyl-[1,4]diazepan-1-yl)-methanone; 5,6-Difluoro-1H-benzoimidazole-2-carboxylic acid (8-methyl-8-aza-bicyclo[3.2.1]oct-3-yl)-amide; (6-Chloro-5-fluoro-1H-benzoimidazol-2-yl)-(4-methyl-piperazin-1-yl)-methanone; (6-Chloro-5-fluoro-1H-benzoimidazol-2-yl)-(4-methyl-[1,4]diazepan-1-yl)-methanone; 6-Chloro-5-fluoro-1H-benzoimidazole-2-carboxylic acid (8-methyl-8-aza-bicyclo[3.2.1]oct-3-yl)-amide; (5-Chloro-6-methyl-1H-benzoimidazol-2-yl)-(4-methyl-piperazin-1-yl)-methanone; (5-Chloro-6-methyl-1H-benzoimidazol-2-yl)-piperazin-1-yl-methanone; (4-Methyl-1H-benzoimidazol-2-yl)-(3-methyl-piperazin-1-yl)-methanone; (4-Ethyl-piperazin-1-yl)-(4-methyl-1H-benzoimidazol-2-yl)-methanone; (4-Methyl-1H-benzoimidazol-2-yl)-(4-methyl-piperazin-1-yl)-methanone; (4-Methyl-1H-benzoimidazol-2-yl)-piperazin-1-yl-methanone; 4-Methyl-1H-benzoimidazole-2-carboxylic acid (8-methyl-8-aza-bicyclo[3.2.1]oct-3-yl)-amide; 5-Methyl-1H-benzoimidazole-2-carboxylic acid (8-methyl-8-aza-bicyclo[3.2.1]oct-3-yl)-amide; (5-Methyl-1H-benzoimidazol-2-yl)-(4-methyl-piperazin-1-yl)-methanone; (4-Methyl-piperazin-1-yl)-(5-trifluoromethyl-1H-benzoimidazol-2-yl)-methanone; Piperazin-1-yl-(5-trifluoromethyl-1H-benzoimidazol-2-yl)-methanone; (5-Fluoro-1H-benzoimidazol-2-yl)-(4-methyl-piperazin-1-yl)-methanone; (4-Ethyl-piperazin-1-yl)-(5-fluoro-1H-benzoimidazol-2-yl)-methanone; (5-Fluoro-1H-benzoimidazol-2-yl)-piperazin-1-yl-methanone; (5-Fluoro-1H-benzoimidazol-2-yl)-(3-methyl-piperazin-1-yl)- methanone; 5-Fluoro-1H-benzoimidazole-carboxylic acid (8-methyl-8-aza-bicyclo[3.2.1]oct-3-yl)-amide; Benzooxazol-2-yl-(4-methyl-piperazin-1-yl)-methanone; (7-Methyl-benzooxazol-2-yl)-(4-methyl-piperazin-1-yl)-methanone; (5-Methyl-benzooxazol-2-yl)-(4-methyl-piperazin-1-yl)-methanone; (4-Methyl-benzooxazol-2-yl)-(4-methyl-piperazin-1-yl)-methanone; Benzothiazol-2-yl-(4-methyl-piperazin-1-yl)-methanone; (5-Benzoyl-1H-benzoimidazol-2-yl)-(4-methyl-piperazin-1-yl)-methanone; (4-Chloro-1H-benzoimidazol-2-yl)-(4-methyl-piperazin-1-yl)-methanone; (4-Methyl-piperazin-1-yl)-(4-nitro-1H-benzoimidazol-2-yl)-methanone; (4-Amino-1H-benzoimidazol-2-yl)-(4-methyl-piperazin-1-yl)-methanone; (4-Isopropylamino-1H-benzoimidazol-2-yl)-(4-methyl-piperazin-1-yl)-methanone; C-(5-Chloro-1H-benzoimidazol-2-yl)-C-(4-methyl-piperazin-1-yl)-methyleneamine; (4,6-Difluoro-1H-benzoimidazol-2-yl)-(4-methyl-piperazin-1-yl)-methanone; (4-Methyl-piperazin-1-yl)-(5-nitro-1H-benzoimidazol-2-yl)-methanone; (5-Fluoro-4-methyl-1H-benzoimidazol-2-yl)-(4-methyl-piperazin-1-yl)-methanone; (5-Bromo-1H-benzoimidazol-2-yl)-(4-methyl-piperazin-1-yl)-methanone; (5,6-Dichloro-1H-benzoimidazol-2-yl)-(4-methyl-piperazin-1-yl)-methanone; (4,5-Dimethyl-1H-benzoimidazol-2-yl)-(4-methyl-piperazin-1-yl)-methanone; (5,6-Dimethyl-1H-benzoimidazol-2-yl)-(4-methyl-piperazin-1-yl)-methanone; (5-Methoxy-1H-benzoimidazol-2-yl)-(4-methyl-piperazin-1-yl)-methanone; (5-Chloro-benzooxazol-2-yl)-(4-methyl-piperazin-1-yl)-methanone; (5-Fluoro-benzooxazol-2-yl)-(4-methyl-piperazin-1-yl)-methanone; (6-Fluoro-benzooxazol-2-yl)-(4-methyl-piperazin-1-yl)-methanone; (5,7-Difluoro-benzooxazol-2-yl)-(4-methyl-piperazin-1-yl)-methanone; (4-Methyl-piperazin-1-yl)-(5-trifluoromethoxy-benzooxazol-2-yl)-methanone; (5-Chloro-benzothiazol-2-yl)-(4-methyl-piperazin-1-yl)-methanone; (4-Methyl-piperazin-1-yl)-(5-trifluoromethyl-benzothiazol-2-yl)-methanone; (4-Methyl-piperazin-1-yl)-(6H-thieno[2,3-b]pyrrol-5-yl)-methanone; (Hexahydro-pyrrolo[1,2-a]pyrazin-2-yl)-(6H-thieno[2,3-b]pyrrol-5-yl)-methanone; (2-Chloro-6H-thieno[2,3-b]pyrrol-5-yl)-(4-methyl-piperazin-1-yl)-methanone; (2-Chloro-6H-thieno[2,3-b]pyrrol-5-yl)-(hexahydro-pyrrolo[1,2-a]pyrazin-2-yl)-methanone; (2-Chloro-6H-thieno[2,3-b]pyrrol-5-yl)-piperazin-1-yl-methanone; (4H-Furo[3,2-b]pyrrol-5-yl)-(4-methyl-piperazin-1-yl)-methanone; (4-Methyl-piperazin-1-yl)-(4H-thieno[3,2-b]pyrrol-5-yl)-methanone; Piperazin-1-yl-(4H-thieno[3,2-b]pyrrol-5-yl)-methanone; (3-Methyl-piperazin-1-yl)-(4H-thieno[3,2-b]pyrrol-5-yl)-methanone; (2-Chloro-4H-thieno[3,2-b]pyrrol-5-yl)-(4-methyl-piperazin-1-yl)-methanone; (2-Chloro-4H-thieno[3,2-b]pyrrol-5-yl)-(hexahydro-pyrrolo[1,2-a]pyrazin-2-yl)-methanone; (3-Bromo-4H-thieno[3,2-b]pyrrol-5-yl)-(4-methyl-piperazin-1-yl)-methanone; 4-Methyl-piperazin-1-yl)-(3-methyl-4H-thieno[3,2-b]pyrrol-5-yl)-methanone; (2-Methyl-4H-furo[3,2-b]pyrrol-5-yl)-(4-methyl-piperazin-1-yl)-methanone; (2,3-Dimethyl-4H-furo[3,2-b]pyrrol-5-yl)-(4-methyl-piperazin-1-yl)-methanone; (2.3-Dimethyl-4H-thieno[3,2-b]pyrrol-5-yl)-(4-methyl-piperazin-1-yl)-methanone; (2,3-Dichloro-6H-thieno[3,2-b]pyrrol-5-yl)-(4-methyl-piperazin-1-yl)-methanone; (2-Methyl-4H-furo[3,2-b]pyrrol-5-yl)-piperazin-1-yl-methanone; (3-Bromo-4H-thieno[3,2-b]pyrrol-5-yl)-piperazin-1-yl-methanone; (3-Bromo-4H-thieno[3,2-b]pyranyl-5-yl)-(3-methyl-piperazin-1-yl)-methanone; (3-Methyl-4H-thieno[3,2-b]pyrrol-5-yl)-piperazin-1-yl-methanone; (3-Methyl-piperazin-1-yl)-(3-methyl-4H-thieno[3,2-b]pyrrol-5-yl)-methanone; (2-Chloro-3-methyl-4H-thieno[3,2-b]pyrrol-5-yl)-(4-methyl-piperazin-1-yl)-methanone; (2-Chloro-3-methyl-4H-thieno[3,2-b]pyrrol-5-yl)-piperazin-1-yl-methanone; (2,3-Dichloro-4H-thieno[3,2-1b]pyrrol-5-yl)-(4-methyl-piperazin-1-yl)-methanone; (2,3-Dimethyl-6H-thieno[2,3-b]pyrrol-5-yl)-(4-methyl-piperazin-1-yl)-methanone; (2-Chloro-3-methyl-6H-thieno[2,3-b]pyrrol-5-yl)-(4-methyl-piperazin-1-yl)-methanone; (3-Chloro-2-methyl-6H-thieno[2,3-b]pyrrol-5-yl)-(4-methyl-piperazin-1-yl)-methanone; (2-Bromo-6H-thieno[2,3-b]pyranol-5-yl)-(4-methyl-piperazin-1-yl)-methanone; (3-Bromo-6H-thieno[2,3-b]pyrrol-5-yl)-(4-methyl-piperazin-1-yl)-methanone; (4-Methyl-piperazin-1-yl)-(2-phenyl-6H-thieno[2,3-b]pyrrol-5-yl)-methanone; [2-(4-Chloro-phenyl)-6H-thieno[2,3-b]pyrrol-5-yl]-(4-methyl-piperazin-1-yl)-methanone; (3-Bromo-4H-thieno[3,2-b]pyranol-5-yl)-(3,4-dimethyl-piperazin-1-yl)-methanone; (3,4-Dimethyl-piperazin-1-yl)-(3-methyl-4H-thieno[3,2-b]pyrrol-5-yl)-methanone; (2-Bromo-3-methyl-4H-thieno[3,2-b]pyrrol-5-yl)-(4-methyl-piperazin-1-yl)-methanone; (3-Bromo-2-chloro-4H-thieno[3,2-b]pyrrol-5-yl)-(4-methyl-piperazin-1-yl)-methanone; (2,3-Dichloro-4H-thieno[3,2-b]pyrrol-5-yl)-(3-methyl-piperazin-1-yl)-methanone; (4-Methyl-piperazin-1-yl)-(2-phenyl-4H-thieno[3,2-b]pyrrol-5-yl)-methanone; (4-Methyl-piperazin-1-yl)-[2-(4-trifluoromethyl-phenyl)-4H-thieno[3,2-pyrrol-5-yl]-methanone; 8-Methyl-3-(4-methyl-piperazin-1-yl)-1H-quinoxalin-2-one; 8-Methyl-3-piperazin-1-yl-1H-quinoxalin-2-one; 8-Nitro-3-piperazin-1-yl-1H-quinoxalin-2-one; 7,8-Difluoro-3-piperazin-1-yl-1H-quinoxalin-2-one; 8-Methyl-3-(3-methyl-piperazin-1-yl)-1H-quinoxalin-2-one; 3-(3-Methyl-piperazin-1-yl)-1H-quinoxalin-2-one; 3-[4-(2-Hydroxy-ethyl)-piperazin-1-yl]-8-methyl-1H-quinoxalin-2-one; 6-Chloro-3-(4-methyl-piperazin-1-yl)-1H-quinoxalin-2-one; 7-Chloro-3-(4-methyl-piperazin-1-yl)-1H-quinoxalin-2-one; 3-(4-Methyl-piperazin-1-yl)-6-trifluoromethyl-1H-quinoxalin-2-one; 3-(4-Methyl-piperazin-1-yl)-7-trifluoromethyl-1H-quinoxalin-2-one; 6,7-Dichloro-3-(4-methyl-piperazin-1-yl)-1H-quinoxalin-2-one; 6,7-Dichloro-3-piperazin-1-yl-1H-quinoxalin-2-one; 6,7-Dichloro-3-(4-methyl-[1,4]diazepan-1-yl)-1H-quinoxalin-2-one; 6,7-Difluoro-3-(4-methyl-piperazin-1-yl)-1H-quinoxalin-2-one; 7-Chloro-6-methyl-3-(4-methyl-piperazin-1-yl)-1H-quinoxalin-2-one; 6-Chloro-7-methyl-3-(4-methyl-piperazin-1-yl)-1H-quinoxalin-2-one; 6-Fluoro-3-(4-methyl-piperazin-1-yl)-1H-quinoxalin-2-one; 7,8-Difluoro-3-(4-methyl-piperazin-1-yl)-1H-quinoxalin-2-one; 8-Chloro-3-(4-methyl-piperazin-1-yl)-6-trifluoromethyl-1H-quinoxalin-2-one; 3-Piperazin-1-yl-6-trifluoromethyl-1H-quinoxalin-2-one; 3-Piperazin-1-yl-7-trifluoromethyl-1H-quinoxalin-2-one; 6-Chloro-7-fluoro-3-(4-methyl-piperazin-1-yl)-1H-quinoxalin-2-one; 7-Chloro-6-fluoro-3-(4-methyl-piperazin-1-yl)-1H-quinoxalin-2-one; 7-Chloro-3-piperazin-1-yl-1H-quinoxalin-2-one; 6-Chloro-3-piperazin-1-yl-1H-quinoxalin-2-one; 6-Chloro-3-(3-methyl-piperazin-1-yl)-1H-quinoxalin-2-one; 7-Chloro-3-(3-methyl-piperazin-1-yl)-1H-quinoxalin-2-one; 3-(3-Methyl-piperazin-1-yl)-6-trifluoromethyl-1H-quinoxalin-2-one; 3-(3-Methyl-piperazin-1-yl)-7-trifluoromethyl-1H-quinoxalin-2-one; 2-{2-Chloro-4-[3-(4-methyl-piperazin-1-yl)-propoxy]-phenyl}-4,5-dimethyl-1H-benzoimidazole; 2-{2-Chloro-4-[3-(1-methyl-piperidin-4-yl)-propoxy]-phenyl}-4-methyl-1H-benzoimidazole; 2-{2-Chloro-4-[3-(4-methyl-piperazin-1-yl)-propoxy]-phenyl}-5-trifluoromethoxy-1H-benzoimidazole; 5-tert-Butyl-2-{3-chloro-4-[3-(4-methyl-[1,4]diazepan-1-yl)-propoxy]-phenyl}-1H-benzoimidazole; 5-tert-Butyl-2-{3-chloro-4-[3-(4-methyl-piperazin-1yl)-propoxy]-phenyl}-1H-benzoimidazole; 4,5-Dimethyl-2-{3-methyl-4-[3-(4-methyl-piperazin-1-yl)-propoxy]-phenyl}-1H-benzoimidazole; 5-tert-Butyl-2-{3-

[4-(4-methyl-piperazin-1yl)-butoxy]-phenyl}-1H-benzoimidazole; 5-tert-Butyl-2-{3-[4-(4-methyl-[1,4]diazepan-1-yl)-butoxy]-phenyl}-1H-benzoimidazole; (1-{3-[4-(5-tert-Butyl-1H-benzoimidazol-2-yl)-2-chloro-phenoxy]-propyl}-pyrrolidin-3-yl)-dimethylamine; 2-{3-Fluoro-4-[3-(4-methyl-piperazin-1-yl)-propoxy]-phenyl}-4-methyl-1H-benzoimidazole; 5-Methyl-2-{4-[3-(4-methyl-piperazin-1-yl)-propoxy]-naphthalen-1-yl}-1H-benzoimidazole; 4-[3-(5-tert-Butyl-1H-benzoimidazol-2-yl)-phenoxy]-1-(4-methyl-piperazin-1-yl)-butan-1-one; 5-Chloro-2-[3-chloro-4-(3-piperazin-1-yl-propoxy)-phenyl]-6-fluoro-1H-benzoimidazole; 5-tert-Butyl-2-{3-methyl-4-[4-methyl-piperazin-1-yl)-propoxy]-phenyl}-1H-benzoimidazole; 2-{2-Chloro-4-[3-(1-methyl-piperidin-4-yl)-propoxy]-phenyl}-4,6-dimethyl-1H-benzoimidazole; 2-{2-Chloro-4-[2-methyl-3-(4-methyl-piperazin-1-yl)-propoxy]-phenyl}-4-methyl-1H-benzoimidazole; 5-Chloro-2-{3-chloro-4-[3-(4-methyl-piperazin-1-yl)-propoxy]-phenyl}-6-methyl-1H-benzoimidazole; 6-Chloro-2-{2-chloro-4-[3-(4-methyl-piperazin-1-yl)-propoxy]-phenyl}-4-ethyl-1H-benzoimidazole; 5-tert-Butyl-2-{3-chloro-4-[3-(4-methyl-piperazin-1-yl)-propoxy]-phenyl}-1H-benzoimidazole; 5-Chloro-2-{3-fluoro-4-[3-(4-methyl-piperazin-1-yl)-propoxy]-phenyl}-1H-benzoimidazole; 2-{2-Chloro-4-[3-(4-methyl-[1,4]diazepan-1-yl)-propoxy]-phenyl}-4,6-dimethyl-1H-benzoimidazole; 5-Chloro-6-methyl-2-{3-[4-(4-methyl-piperazin-1-yl)-butoxy]-phenyl}-1H-benzoimidazole; 2-{3-Fluoro-4-[4-methyl-piperazin-1-yl)-propoxy]-phenyl}-5-methyl-1H-benzoimidazole; 5,6-Difluoro-2-{3-fluoro-4-[4-methyl-piperazin-1-yl)-propoxy]-phenyl}-1H-benzoimidazole; 2-{3-Fluoro-4-[4-methyl-piperazin-1-yl)-propoxy]-phenyl}-1H-benzoimidazole; 2-{2-Chloro-4-[3-(4-methyl-[1,4]diazepan-1-yl)-propoxy]-phenyl}-4,5-dimethyl-1H-benzoimidazole; 5,6-Dimethyl-2-{3-[4-4-(4-methyl-piperazin-1-yl)-butoxy]-phenyl}-1H-benzoimidazole; 2-{2-Chloro-4-[3-(4-methyl-piperazin-1-yl)-propoxy]-phenyl}-4,6-dimethyl-1H-benzoimidazole; 2-{2-Chloro-4-[3-(4-methyl-[1,4]diazepan-1-yl)-propoxy]-phenyl}-4-methyl-1H-benzoimidazole; 5-tert-Butyl-2-{2-chloro-4-[3-(4-methyl-piperazin-1-yl)-propoxy]-phenyl}-1H-benzoimidazole; 2-{3-Methoxy-4-[3-(4-methyl-piperazin-1-yl)-propoxy3-phenyl}-5-trifluoromethyl-1H-benzoimidazole; 5-Chloro-2-{3-chloro-4-[3-(4-methyl-piperazin-1-yl)-propoxy]-phenyl}-6-fluoro-1H-benzoimidazole; 5,6-Dichloro-2-{2-chloro-4-[3-(4-methyl-piperazin-1-yl)-propoxy]-phenyl}-1H-benzoimidazole; 5-Chloro-2-{2-chloro-4-[3-(4-methyl-piperazin-1-yl)-propoxy]-phenyl}-1H-benzoimidazole; 5-Chloro-2-{2-chloro-4-[3-(4-methyl-piperazin-1-yl)-propoxy]-phenyl}-6-fluoro-1H-benzoimidazole; 5-Chloro-2-{3-methyl-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-methyl-1H-benzoimidazole; 5,6-Dichloro-2-{3-chloro-4-[3-(4-methyl-piperazin-1-yl)-propoxy]-phenyl}-1H-benzoimidazole; 5-Chloro-6-methyl-2-{3-methyl-4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-5-methyl-1H-benzoimidazole; 5-Chloro-2-{3-chloro-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-trifluoromethyl-1H-benzoimidazole; 5-Chloro-6-fluoro-2-{3-methyl-4-[3-(4-methyl-piperazin-1-yl)-propoxy]-phenyl}-1H-benzoimidazole; 5-Methyl-2-{3-methyl-4-[3-(4-methyl-piperazin-1-yl)-propoxy]-1H-benzoimidazole; 2-{3-Chloro-4-[3-(4-methyl-piperazin-1-yl)-propoxy]-phenyl}-1H-benzoimidazole; 2-{3-Methyl-4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-1H-benzoimidazole; 5-Chloro-6-fluoro-2-{3-methoxy-4-[3-(4-methyl-piperazin-1-yl)-propoxy]-phenyl}-1H-benzoimidazole; 2-{3-Chloro-4-[3-(4-methyl-piperazin-1-yl)-propoxy]-phenyl}-5-methoxy-1H-benzoimidazole; 5-tert-Butyl-2-{3,5-dibromo-4-[3-(4-methyl-piperazin-1-yl)-propoxy]-phenyl}-1H-benzoimidazole; 2-{2-Methoxy-4-[3-(4-methyl-piperazin-1-yl)-propoxy]-phenyl}-5-trifluoromethyl-1H-benzoimidazole; 2-{2-Chloro-4-[3-(4-methyl-piperazin-1-yl)-propoxy]-phenyl}-5-trifluoromethyl-1H-benzoimidazole; 2-{3-[3-(4-Methyl-piperazin-1-yl)-propoxy]-phenyl}-1H-benzoimidazole; (2-{3-[4-(4-Methyl-piperazin-1-yl)-butoxy]-phenyl}-1H-benzoimidazol-5-yl)-phenyl-methanone; 6-Chloro-2-{2-chloro-4-[3-(1-methyl-piperidin-4-yl)-propoxy]-phenyl}-4-methyl-1H-benzoimidazole; 5-tert-Butyl-2-{3-chloro-4-[3-(1-methyl-piperidin-4-yl)-propoxy]-phenyl}-1H-benzoimidazole; 2-{2-Chloro-4-[3-(1-methyl-piperidin-4-yl)-propoxy]-phenyl}-4,5-dimethyl-1H-benzoimidazole; 5-Chloro-6-methyl-2-{4-[3-(1-methyl-piperidin-4-yl)-propoxy]-phenyl}-1H-benzoimidazole; 5-Chloro-2-{4-[3-(1-methyl-piperidin-4-yl)-propoxy]-phenyl}-1H-benzoimidazole; 5-Chloro-6-fluoro-2-{4-[3-(1-methyl-piperidin-4-yl)-propoxy]-phenyl}-1H-benzoimidazole; 5-tert-Butyl-2-{4-[3-(1-methyl-piperidin-4-yl)-propoxy]-phenyl}-1H-benzoimidazole; 5-Methyl-2-{4-[3-(1-methyl-piperidin-4-yl)-propoxy]-phenyl}-1H-benzoimidazole; 2-{4-[3-(1-Methyl-piperidin-4-yl)-propoxy]-phenyl}-1H-benzoimidazole; 6-Chloro-2-{2-fluoro-4-[3-(1-methyl-piperidin-4-yl)-propoxy]-phenyl}-4-methyl-1H-benzoimidazole; 5-Fluoro-2-{2-methyl-4-[3-(1-methyl-piperidin-4-yl)-propoxy]-phenyl}-1H-benzoimidazole; 4-Chloro-2-{2-methyl-4-[3-(1-methyl-piperidin-4-yl)-propoxy]-phenyl}-1H-benzoimidazole; 6-Chloro-4-methyl-2-{2-methyl-4-[3-(1-methyl-piperidin-4-yl)-propoxy]-phenyl}-1H-benzoimidazole; 2-{2-Chloro-4-[3-(1-methyl-piperidin-4-yl)-propoxy]-phenyl}-3H-naphtho[1,2-d]imidazole; 4,6-Dimethyl-2-{2-methyl-4-[3-(4-methyl-piperazin-1-yl)-propoxy]-phenyl}-1H-benzoimidazole; 2-{2-Chloro-4-[3-(4-methyl-piperazin-1-yl)-propoxy]-phenyl}-4-methyl-1H-benzoimidazole; 2-{2-Chloro-4-[3-(4-methyl-piperazin-1-yl)-propoxy]-phenyl}-5-fluoro-4-methyl-1H-benzoimidazole; 2-{2-Chloro-4-[3-(4-methyl-piperazin-1-yl)-propoxy]-phenyl}-3H-naphtho[1,2-d]imidazole; 6-Chloro-2-{2-chloro-4-[3-(4-methyl-[1,4]diazepan-1-yl)-propoxy]-phenyl}-4-methyl-1H-benzoimidazole; 2-{3-Chloro-4-[3-(4-methyl-[1,4]diazepan-1-yl)-propoxy]-phenyl}-4-methyl-1H-benzoimidazole; 4,6-Dimethyl-2-{3-[4-(4-methyl-[1,4]diazepan-1-yl)-butoxy]-phenyl}-1H-benzoimidazole; 5-Chloro-2-{4-[3-(4-methyl-piperazin-1-yl)-propoxy]-phenyl}-1H-benzoimidazole; 2-{4-[3-(4-Methyl-piperazin-1-yl)-propoxy]-phenyl}-1H-benzoimidazole; {2-(6-Chloro-4-methyl-1H-benzoimidazol-2-yl)-5-[3-(1-methyl-piperidin-4-yl)-propoxy]-benzyl}-dimethyl-amine; {2-(5-Fluoro-4-methyl-1H-benzoimidazol-2-yl)-5-[3-(1-methyl-piperidin-4-yl)-propoxy]-benzyl}-dimethyl-amine; 4-{3-[4-(6-Chloro-4-methyl-1H-benzoimidazol-2-yl)-3-methyl-phenoxy]-propyl}-[1,4]diazepan-5-one; 4-{3-[4-(5-tert-Butyl-1H-benzoimidazol-2-yl)-3-methyl-phenoxy]-propyl}-1-methyl-[1,4]diazepan-5-one; 5-tert-Butyl-2-{2-methyl-4-[3-(2-methyl-piperazin-1-yl)-propoxy]-phenyl}-1H-benzoimidazole; 5-tert-Butyl-2-{2-methyl-4-[3-(2-methyl-piperazin-1-yl)-propoxy]-phenyl}-1H- benzoimidazole; 6-Chloro-4-methyl-2-[2-methyl-4-(3-piperidin-4-yl-propoxy)-phenyl]-1H-benzoimidazole; 5-Fluoro-4-methyl-2-[2-methyl-4-(3-piperidin-4-yl-propoxy)-phenyl]-1H-benzoimidazole; 6-Chloro-2-{4-[3-(1-ethyl-piperidin-4-yl)-propoxy]-2-methyl-phenyl}-4-methyl-1H-benzoimidazole; {2-[3-Chloro-4-(4-methyl-1H-benzoimidazol-2-yl)-phenoxy]-ethyl}-methyl-(1-methyl-piperidin-4-yl)-amine; 6-Chloro-4-methyl-2-{2-methyl-4-[2-(1-methyl-piperidin-4-yloxy)-ethoxy]-phenyl}-1H-benzoimidazole; 6-Chloro-4-methyl-2-{2-methyl-4-[3-(1-methyl-1,2-6-tetrahydro-pyridin-4-yl)-propoxy]-phenyl}-1H-benzoimidazole; 5-Fluoro-4-methyl-2-{2-methyl-4-[3-(1-methyl-1,2,3,6-tetrahydro-pyridin-4-yl)-propoxy]-phenyl}-1H-benzoimidazole; 6-Fluoro-7-methyl-2-{3-[4-(1-methyl-piperidin-4-yl)-butoxy]-phenyl}-1H-benzoimidazole; 7-Methyl-2-{3-[4-(1-methyl-piperidin-4-yl)-butoxy]-phenyl}-1H-benzoimidazole; 6,7-Dimethyl-2-{3-[4-1-methyl-piperidin-4-yl)-butoxy]-phenyl}-1H-benzoimidazole; (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (1H-Indol-2-yl)-(4-methyl-piperazin-1-yl)-methanone; (5-Benzyloxy-1H-indol-2-yl)-(4-methyl-piperazin-1-yl)-methanone; (5-Methyl-1H-indol-2-yl)-(4-methyl-piperazin-1-yl)-methanone; (5,6-Dimethoxy-1H-indol-2-yl)-(4-methyl-piperazin-1-yl)-methanone; (4-Methyl-piperazin-1-yl)-(7-nitro-1H-indol-2-yl)-methanone; (4-Methyl-piperazin-1-yl)-(5-nitro-3-phenyl-1H-indol-2-yl)-methanone; (4-Methyl-piperazin-1-yl)-(5-trifluoromethoxy-1H-indol-2-yl)-methanone; (6-Chloro-1H-indol-2-yl)-(4-methyl-piperazin-1-yl)-methanone; (5,7-Difluoro-1H-indol-2-yl)-(4-methyl-piperazin-1-yl)-methanone; (6-Fluoro-1H-indol-2-yl)-(4-methyl-piperazin-1-yl)-methanone; (4,6-Dichloro-1H-indol-2-yl)-(4-methyl-piperazin-1-yl)-methanone; (1H-Indol-2-yl)-(4-octyl-piperazin-1-yl)-methanone; (4-Ethyl-piperazin-1-yl)-(1H-indol-2-yl)-methanone; (1H-Indol-2-yl)-(4-isopropyl-piperazin-1-yl)-methanone; [4-(3-Dimethylamino-propyl)-piperazin-1-yl]-(1H-indol-2-yl)-methanone; (4-Butyl-piperazin-1-yl)-(1H-indol-2-yl)-methanone; (4-Cyclopentyl-piperazin-1-yl)-(1H-indol-2-yl)-methanone; (1H-Indol-2-yl)-(4-phenethyl-piperazin-1-yl)-methanone; (1H-Indol-2-yl)-[4-(2-piperidin-1-yl-ethyl)-piperazin-1-yl]-methanone; [4-(2-Ethoxy-ethyl)-piperazin-1-yl]-(1H-indol-2-yl)-methanone; (4-sec-Butyl-piperazin-1-yl)-(1H-indol-2-yl)-methanone; [4-(1-Ethyl-propyl)-piperazin-1-yl]-(1H-indol-2-yl)-methanone; (1H-Indol-2-yl)-[4-(3-phenyl-propyl)-piperazin-1-yl]-methanone; (1H-Indol-2-yl)-[4-(1-methyl-piperidin-4-yl)-piperazin-1-yl]-methanone; [4-(2-Dipropylamino-ethyl)-piperazin-1-yl]-1H-indol-2-yl)-methanone; (1H-Indol-2-yl)-[4-(3-phenyl-allyl)-piperazin-1-yl]-methanone; (1H-Indol-2-yl)-(4-pentyl-piperazin-1-yl]-methanone; (4-Heptyl-piperazin-1-yl)-(1H-indol-2-yl)-methanone; [4-(2-Diethylamino-ethyl)-piperazin-1-yl]-(1H-indol-2-yl)-methanone; (1H-Indol-2-yl)-[4-(4-methoxy-butyl)-pyperazin-1-yl]-methanone; 5-Chloro-7-methyl-2-{3-[4-1-methyl-piperidin-4-yl)-butoxy]-phenyl}-1H-benzoimidazole; 5,7-Dimethyl-2-{2-methyl-3-[4-(1-methyl-piperidin-4-yl)-butoxy]-phenyl}-1H-benzoimidazole; 5-Chloro-7-methyl-2-{2-methyl-3-[4-(1-methyl-piperidin-4-yl)-butoxy]-phenyl}-1H-benzoimidazole; 6-Fluoro-7-methyl-2-{2-methyl-3-[4-(1-methyl-piperidin-4-yl)-butoxy]-phenyl}-1H-benzoimidazole; 6-Fluoro-7-methyl-2-{3-[3-(1-methyl-piperidin-4-yloxy)-propoxy]-phenyl}-1H-benzoimidazole; {2-(5-Fluoro-4-methyl-1H-benzoimidazol-2-yl)-5-[3-(1-methyl-piperidin-4-yl)-propoxy]-phenyl}-methanol; 6-Chloro-4-methyl-2-{6-[3-(4-methyl-piperazin-1-yl)-propoxy]-pyridin-3-yl}-1H-benzoimidazole; 4-Methyl-2-{6-[3-(4-methyl-piperazin-1-yl)-propoxy]-pyridin-3-yl}-1H-benzoimidazole; 5-Fluoro-4-methyl-2-{6-[3-(4-methyl-piperaztn-1-yl)-propoxy]-pyridin-3-yl}-1H-benzoimidazole; 4-Methyl-2-{6-[3-(1-methyl-piperidin-4-yl)-propoxy]-pyridin-3-yl}-1H-benzoimidazole; 4,5-Dimethyl-2-{6-[3-(1-methyl-piperidin-4-yl)-propoxy]-pyridin-3-yl}-1H-benzoimidazole; 4-Chloro-2-{6-[3-(1-methyl-piperidin-4-yl)-propoxy]-pyridin-3-yl}-1H-benzoimidazole; 5-Fluoro-4-methyl-2-{4-methyl-6-[3-(1-methyl-piperidin-4-yl)-propoxy]-pyridin-3-yl}-1H-benzoimidazole; 4,5-Dimethyl-2-{4-methyl-6-[3-(1-methyl-piperidin-4-yl)-propoxy]-pyridin-3-yl}-1H-benzoimidazole; 4,6-Dimethyl-2-{4-methyl-6-[3-(1-methyl-piperidin-4-yl)-propoxy]-pyridin-3-yl}-1H-benzoimidazole; 4-Chloro-2-{4-methyl-6-[3-(1-methyl-piperidin-4-yl)-propoxy]-pyridin-3-yl}-1H-benzoimidazole; 2-{4-Chloro-6-[3-(1-methyl-piperidin-4-yl)-propoxy]-pyridin-3-yl}-5-fluoro-4-methyl-1H-benzoimidazole; 2-{4-Chloro-6-[3-(1-methyl-piperidin-4-yl)-propoxy]-pyridin-3-yl}-4-methyl-1H-benzoimidazole; 6-Chloro-2-{4-chloro-6-[3-(1-methyl-piperidin-4-yl)-propoxy]-pyridin-3-yl}-4-methyl-1H-benzoimidazole; 2-{4-Chloro-6-[3-(1-methyl-piperidin-4-yl)-propoxy]-pyridin-3-yl}-4,6-dimethyl-1H-benzoimidazole; 2-{4-Methoxy-6-[3-(1-methyl-piperidin-4-yl)-propoxy]-pyridin-3-yl}-4-methyl-1H-benzoimidazole; 5-Fluoro-2-{4-methoxy-6-[3-(1-methyl-piperidin-4-yl)-propoxy]-pyridin-3-yl}-4-methyl-1H-benzoimidazole; 5-Fluoro-4-methyl-2-{6-[3-(1-methyl-1,2,3,6-tetrahydro-pyridin-4-yl)-propoxy]-pyridin-3-yl}-1H-benzoimidazole; 4-Methyl-2-{6-[3-(1-methyl-1,2,3,6-tetrahydro-pyridin-4-yl)-propoxy]-pyridin-3-yl}-1H-benzoimidazole; 6-Chloro-4-methyl-2-{6-[3-(1-methyl-1,2,3,6-tetrahydro-pyridin-4-yl)-propoxy]-pyridin-3-yl}-1H-benzoimidazole; 4,5-Dimethyl-2-{6-[3-(1-methyl-1,2,3,6-tetrahydro-pyridin-4-yl)-propoxy]-pyridin-3-yl}-1H-benzoimidazole; 4,6-Dimethyl-2-{6-[3-(1-methyl-1,2,3,6-tetrahydro-pyridin-4-yl)-propoxy]-pyridin-3-yl}-1H-benzoimidazole; 5-Chloro-4-methyl-2-{6-[3-(1-methyl-1,2,3,6-tetrahydro-pyridin-4-yl)-propoxy]-pyridin-3-yl}-1H-benzoimidazole; 5-Fluoro-4-methyl-2-{6-[3-(1-methyl-piperidin-4-yl)-propoxy]-4-pyrrolidin-1-ylmethyl-pyridin-3-yl}-1H-benzoimidazole; 2-{5-Bromo-2-[4-(1-methyl-piperidin-4-yl)-butoxy]-pyridin-4-yl}-4-methyl-1H-benzoimidazole; 2-{5-Bromo-2-[4-(1-methyl-piperidin-4-yl)-butoxy]-pyridin-4-yl}-5-fluoro-4-methyl-1H-benzoimidazole; 2-{5-Bromo-2-[4-(1-methyl-piperidin-4-yl)-butoxy]-pyridin-4-yl}-6-chloro-4-methyl-1H-benzoimidazole; 2-{5-Bromo-2-[4-(1-methyl-piperidin-4-yl)-butoxy]-pyridin-4-yl}-4,6-dimethyl-1H-benzoimidazole; 2-{5-Bromo-2-[4-(1-methyl-piperidin-4-yl)-butoxy]-pyridin-4-yl}-4,5-dimethyl-1H-benzoimidazole; 2-{5-Bromo-2-[4-(1-methyl-piperidin-4-yl)-butoxy]-pyridin-4-yl}-5-chloro-4-methyl-1H-benzoimidazole; 2-{5-Bromo-2-[4-(1-methyl-piperidin-4-yl)-butoxy]-pyridin-4-yl}-5-tert-butyl-1H-benzoimidazole; 5-tert-Butyl-2-{2-[4-(1-methyl-piperidin-4-yl)-butoxy]-pyridin-4-yl}-1H-benzoimidazole; 2-{5-Chloro-2-[4-(1-methyl-piperidin-4-yl)-butoxy]-pyridin-4-yl}-5-fluoro-4-methyl-1H-benzoimidazole; 2-{5-Chloro-2-[4-(1-methyl-piperidin-4-yl)-butoxy]-pyridin-4-yl}-4,5-dimethyl-1H-benzoimidazole; 4,6-Dimethyl-2-{2-[4-(4-methyl-piperazin-1-yl)-butoxy]-pyridin-4-yl}-1H-benzoimidazole; 4-Methyl-2-{2-[4-(4-methyl-piperazin-1-yl)-butoxy]-pyridin-4-yl}-1H-benzoimidazole; 4,5-Dimethyl-2-{2-[4-(4-methyl-piperazin-1-yl)-butoxy]-pyridin-4-yl}-1H-benzoimidazole; 5-Fluoro-4-methyl-2-{2-[4-(4-methyl-piperazin-1-yl)-butoxy]-pyridin-4-yl}-1H-benzoimidazole; 6-Chloro-4-methyl-2-{2-[4-(4-methyl-piperazin-1-yl)-butoxy]-pyridin-4-yl}-1H-benzoimidazole; 5-Fluoro-4-methyl-2-{2-[4-(4-methyl-[1,4]diazepan-1-yl)-butoxy]-pyridin-4-yl}-1H-benzoimidazole; 4,5-Dimethyl-2-{2-[4-(4-methyl-[1,4]diazepan-1-yl)-butoxy]-pyridin-4-yl}-1H-benzoimidazole; 4,6-Dimethyl-2-{2-[4-(1-methyl-piperidin-4-yl)-butoxy]-pyridin-4-yl}-1H-benzoimidazole; 4-Methyl-2-{2-[4-(1-methyl-piperidin-4-yl)-butoxy]-pyridin-4-yl}-1H-benzoimidazole; 5-Fluoro-4-methyl-2-{2-[4-(1-methyl-piperidin-4-yl)-butoxy]-pyridin-4-yl}-1H-benzoimidazole; 4-Chloro-2-{2-[4-(1-methyl-piperidin-4-yl)-butoxy]-pyridin-4-yl}-1H-benzoimidazole; 4,5-Dimethyl-2-{2-[4-(1-methyl-piperidin-4-yl)-butoxy]-pyridin-4-yl}-1H-benzoimidazole; 6-Chloro-4-methyl-2-{2-[4-(1-methyl-piperidin-4-yl)-butoxy]-pyridin-4-yl}-1H-benzoimidazole; 5-tert-Butyl-2-[2-(4-piperidin-4-yl-butoxy)-pyridin-4-yl]-1H-benzoimidazole; 4,6-Dimethyl-2-[2-(4-piperidin-4-yl-butoxy)-pyridin-4-yl]-1H-benzoimidazole; 2-{2-[4-(1-Ethyl-piperidin-4-yl)-butoxy]-pyridin-4-yl}-4,5-dimethyl-1H-benzoimidazole; 4,6-Dimethyl-2-{3-methyl-2-[4-(1-methyl-piperidin-4-yl)-butoxy]-pyridin-4-yl}-1H-benzoimidazole; 4-Methyl-2-{3-methyl-2-[4-(1-methyl-piperidin-4-yl)-butoxy]-pyridin-4-yl}-1H-benzoimidazole; 6-Chloro-4-methyl-2-{3-methyl-2-[4-(1-methyl-piperidin-4-yl)-butoxy]-pyridin-4-yl}-1H-benzoimidazole; 2-{3-Chloro-2-[4-(1-methyl-piperidin-4-yl)-butoxy]-pyridin-4-yl}-4-methyl-1H-benzoimidazole; 2-{3-Chloro-2-[4-(1-methyl-piperidin-4-yl)-butoxy]-pyridin-4-yl}-4,5-dimethyl-1H-benzoimidazole; 4-Chloro-2-{3-chloro-2-[4-(1-methyl-piperidin-4-yl)-butoxy]-pyridin-4-yl}-1H-benzoimidazole; 2-{3-Chloro-2-[4-(1-methyl-piperidin-4-yl)-butoxy]-pyridin-4-yl}-5-fluoro-4-methyl-1H-benzoimidazole; 2-{3-Chloro-2-[4-(1-methyl-piperidin-4-yl)-butoxy]-pyridin-4-yl}-4,6-dimethyl-1H-benzoimidazole; 6-Chloro-2-{3-chloro-2-[4-(1-methyl-piperidin-4-yl)-butoxy]-pyridin-4-yl}-4-methyl-1H-benzoimidazole; 5-Fluoro-4-methyl-2-{5-methyl-2-[4-(1-methyl-piperidin-4-yl)-butoxy]-pyridin-4-yl}-1H-benzoimidazole; 5-Chloro-6-fluoro-2-{5-methyl-2-[4-(1-methyl-piperidin-4-yl)-butoxy]-pyridin-4-yl}-1H-benzoimidazole; 5-tert-Butyl-2-{5-methyl-2-[4-(1-methyl-piperidin-4-yl)-butoxy]-pyridin-4-yl}-1H-benzoimidazole; 4,5-Dimethyl-2-{5-methyl-2-[4-(1-methyl-piperidin-4-yl)-butoxy]-pyridin-4-yl}-1H-benzoimidazole; 2-{5-Chloro-2-[4-(1-methyl-piperidin-4-yl)-butoxy]-pyridin-4-yl}-4,6-dimethyl-1H-benzoimidazole; 5-tert-Butyl-2-{5-chloro-2-[4-(1-methyl-piperidin-4-yl)-butoxy]-pyridin-4-yl}-1H-benzoimidazole; 2-{5-Bromo-2-[4-(1-methyl-piperidin-4-yl)-butoxy]-pyridin-4-yl}-4-chloro-1H-benzoimidazole; 2-{5-Bromo-2-[4-(1-methyl-piperidin-4-yl)-butoxy]-pyridin-4-yl}-5-chloro-6-fluoro-1H-benzoimidazole; 2-{5-Bromo-2-[4-(1-methyl-piperidin-4-yl)-butoxy]-pyridin-4-yl}-5-chloro-1H-benzoimidazole; 1-(3-{4-[4,5-Bis-(4-bromo-phenyl)-1H-imidazol-2-yl]-3-chloro-phenoxy}-propyl)-4-methyl-piperazine; 1-{3-[3-Chloro-4-(4,5-diphenyl-1H-imidazol-2-yl)-phenoxy]-propyl}-4-methyl-piperazine; 1-(3-{4-[4,5-Bis-(4-methoxy-phenyl)-1H-imidazol-2-yl]-3-chloro-phenoxy}-propyl)-4-methyl-piperazine; 1-{3-[3-Chloro-4-(4,5-di-p-tolyl-1H-imidazol-2-yl)-phenoxy]-propyl}-4-methyl-piperazine; 1-(3-{4-[4,5-Bis-(3-methoxy-phenyl)-1H-imidazol-2-yl]-3-chloro-phenoxy}-propyl)-4-methyl-piperazine; 1-(3-{4-[4,5-Bis-(3-methoxy-phenyl)-1H-imidazol-2-yl]-2-fluoro-phenoxy}-propyl)-4-methyl-piperazine; 1-(3-{4-[4,5-Bis-(4-bromo-phenyl)-1H-imidazol-2-yl]-3-chloro-phenoxy}-propyl)-4-methyl-[1,4]diazepane; 1-(3-{4-[4,5-Bis-(3-methoxy-phenyl)-1H-imidazol-2-yl]-3-chloro-phenoxy}-propyl)-4-methyl-[1,4]diazepane; 2-{3-Chloro-4-[3-(4-methyl-[1,4]diazepan-1-yl)-propoxy]-phenyl}-4,5,6,7-tetrahydro-1H-benzoimidazole; 2-{2-Chloro-4-[3-(4-methyl-[1,4]diazepan-1-yl)-propoxy]-phenyl}-4,5,6,7-tetrahydro-1H-benzoimidazole; 1-Methyl-4-{3-[3-methyl-4-(4-phenyl-5-trifluoromethyl-1H-imidazol-2-yl)-phenoxy]-propyl}-piperidine; 4-{3-[3-Chloro-4-(4-phenyl-5-trifluoromethyl-1H-imidazol-2-yl)-phenoxy]-propyl}-1-methyl-piperidine; 4-(3-{3-Chloro-4-[5-methyl-4-(3-trifluoromethyl-phenyl)-1H-imidazol-2-yl]-phenoxy}-propyl)-1-methyl-piperidine; 4-(3-{3-Chloro-4-[4-(3,5-dichloro-phenyl)-5-methyl-1H-imidazol-2-yl]-phenoxy}-propyl)-1-methyl-piperidine; 4-(3-{4-[4-(3,5-Dichloro-phenyl)-5-methyl-1H-imidazol-2-yl]-3-methyl-phenoxy}-propyl)-1-methyl-piperidine; 4-(3-{3-Chloro-4-[4-(4-chloro-phenyl)-5-methyl-1H-imidazol-2-yl]-phenoxy}-propyl)-1-methyl-piperidine; 4-(3-{4-[4,5-Bis-(4-fluoro-phenyl)-1H-imidazol-2-yl]-3-chloro-phenoxy}-propyl)-1-methyl-piperidine; 4-(3-{4-[4,5-Bis-(3-methoxy-phenyl)-1H-imidazol-2-yl]-3-chloro-phenoxy}-propyl)-1-methyl-piperidine; 4-(3-{3-Chloro-4-[4-(4-chloro-phenyl)-5-p-tolyl-1H-imidazol-2-yl]-phenoxy}-propyl)-1-methyl-piperidine; 2-{2-Chloro-4-[3-(1-methyl-piperidin-4-yl)-propoxy]-phenyl}-4,5,6,7-tetrahydro-1H-benzoimidazole; 4-{3-[3-Chloro-4-(4-methyl-5-propyl-1H-imidazol-2-yl)-phenoxy]-propyl}-1-methyl-piperidine; 4-{3-[3-Chloro-4-(5-ethyl-4-methyl-1H-imidazol-2-yl)-phenoxy]-propyl}-1-methylpiperidine; 1-Methyl-4-(2-{3-methyl-4-[5-methyl-4-(3-trifluoromethyl-phenyl)-1H-imidazol-2-yl]-phenoxyl}-ethoxy)-piperidine; 5-[4-(4-Chloro-phenyl)-5-methyl-1H-imidazol-2-yl]-2-[3-(1-methyl-piperidin-4-yl)-propoxy]-pyridine; 2-[3-(1-Methyl-piperidin-4-yl)-propoxy]-5-[5-methyl-4-(3-trifluoromethyl-phenyl)-1H-imidazol-2-yl]-pyridine; 2-[3-(1-Methyl-piperidin-4-yl)-propoxy]-5-[5-methyl-4-(4-trifluoromethyl-phenyl)-1H-imidazol-2-yl]-pyridine; 2-[3-(1-Methyl-piperidin-4-yl)-propoxy]-5-(4-phenyl-5-trifluoromethyl-1H-imidazol-2-yl)-pyridine; 1-Methyl-4-(3-{5-[5-methyl-4-(4-trifluoromethyl-phenyl)-1H-imidazol-2-yl]-pyridin-2-yloxyl}-propyl)-piperazine; 1-Methyl-4-(3-{5-[5-methyl-4-(3-trifluoromethyl-phenyl)-1H-imidazol-2-yl]-pyridin-2-yloxyl}-propyl)-piperazine; 4-(4-{3-[4-(4-Chloro-phenyl)-5-methyl-1H-imidazol-2-yl]-phenoxy}-butyl)-1-methyl-piperidine; 1-Methyl-4-{4-[3-(4-phenyl-5-trifluoromethyl-1H-imidazol-2-yl)-phenoxy-butyl}-piperidine; 2-[4-(1-Methyl-piperidin-4-yl)-butoxy]-4-(4-phenyl-5-trifluoromethyl-1H-imidazol-2-yl)-pyridine; 2-[4-(1-Methyl-piperidin-4-yl)-butoxy]-4-[5-methyl-4-(3-trifluoromethyl-phenyl)-1H-imidazol-2-yl]-pyridine; 4-{3-[4-5-Isobutyl-4-methyl-1H-imidazol-2-yl]-3-methyl-phenoxy]-propyl}-1-methyl-piperidine; 4-[4-(4-Chloro-phenyl)-5-methyl-1H-imidazol-2-yl]-2-[4-(1-methyl-piperidin-4-yl)-butoxy]-pyridine; 4-{3-[3-Chloro-4-(5-isobutyl-4-methyl-1H-imidazol-2-yl)-phenoxy]-propyl}-1-methyl-piperidine; 1-Methyl-4-(4-{3-[5-methyl-4-(4-trifluoromethyl-phenyl)-1H-imidazol-2-yl]-phenoxyl-butyl)-piperidine; 1-{3-[2-Chloro-4-(1H-imidazol-2-yl)-phenoxy]-propyl}-4-methyl-piperazine; 1-{3-[3-Chloro-4-(4,5-dimethyl-1H-imidazol-2-yl)-phenoxy]-propyl}-4-methyl-piperazine; 1-{3-[3-Chloro-4-(4-phenyl-5-trifluoromethyl-1H-imidazol-2-yl)-phenoxy]-propyl}-4-methyl-piperazine; 1-{3-[2-Chloro-4-(4-phenyl-5-trifluoromethyl-1H-imidazol-2-yl)-phenoxy]-propyl}-4-methyl-[1,4]diazepane; 1-Methyl-4-(3-{3-methyl-4-[5-methyl-4-(3-trifluoromethyl-phenyl)-1H-imidazol-2-yl]-phenoxy}-propyl)-piperidine; 4-(3-{4-[4-(4-Chloro-phenyl)-5-methyl-1H-imidazol-2-yl]-3-methyl-phenoxy}- propyl)-1-methyl-piperidine; 4-(2-{4-[4-(4-Chloro-phenyl)-5-methyl-1H-imidazol-2-yl]-3-methyl-phenoxy}-ethoxy)-1-methyl-piperidine; 1-(3-{4-[4-(4-Chloro-phenyl)-5-methyl-1H-imidazol-2-yl]-3-methyl-phenoxy}-2-methyl-propyl)-4-methyl-piperazine; 2-[4-(4-Chloro-phenyl)-5-methyl-1H-imidazol-2-yl]-6-[4-(1-methyl-piperidin-4-yl)-butoxy]-pyridine; 4-Methyl-2-[3-(1-methyl-piperidin-4-yl)-propoxy]-5-[5-methyl-4-(3-trifluoromethyl-phenyl)-1H-imidazol-2-yl]-pyridine; 5-Bromo-4-[4-(4-chloro-phenyl)-5-methyl-1H-imidazol-2-yl]-2-[4-(1-methyl-piperidin-4-yl)-butoxy]-pyridine; 2,4-Dimethyl-1-{3-[4-4-phenyl-5-trifluoromethyl-1H-imidazol-2-yl]-phenoxy]-propyl}-piperazine; 1,2-Dimethyl-4-{3-[4-(4-phenyl-5-trifluoromethyt-1H-imidazol-2-yl)-phenoxy]-propyl}-piperazine; 3-Chloro-2-[4-(1-methyl-piperidin-4-yl)-butoxy]-4-(4-phenyl-5-trifluoromethyl-1H-imidazol-2-yl)-pyridine; 1-Methyl-4-(4-{4-[5-methyl-4-(3-trifluoromethyl-phenyl)-1H-imidazol-2-yl]-pyridin-2-yloxyl}-butyl)-[1,4]diazepane; 5-Bromo-2-[4-(1-methyl-piperidin-4-yl)-butoxy]-4-[5-methyl-4-(3-trifluoromethyl-phenyl)-1H-imidazol-2-yl]-pyridine; 4-[4-(4-Chloro-phenyl)-5-trifluoromethyl-1H-imidazol-2-yl]-2-[4-(1-methyl-piperidin-4-yl)-butoxy]-pyrimidine; 4-(3-{4-[5-Cyclopropylmethyl-4-(3-trifluoromethyl-phenyl)-1H-imidazol-2-yl]-3-methyl-phenoxy}~propyl)-1-methyl-piperidine; 1-{4-[4-(4-Chtoro-phenyl)-5-methyl-1H-imidazol-2-yl]-3-methyl-phenoxy}-3-(4-methyl-piperazin-1-yl)-propan-2-ol; 4-(3-{3-Chloro-4-[4-(4-chloro-phenyl)-5-methyl-1H-imidazol-2-yl]-phenoxyl}-propyl)-piperidine; 4-(3-{3-Chloro-4-[4-(4-chloro-phenyl)-5-methyl-1H-imidazol-2-yl]-phenoxyl}-propyl)-1-ethyl-piperidine; 4-(3-{3-Chloro-4-[4-(4-chloro-phenyl)-5-methyl-1H-imidazol-2-yl]-phenoxyl}-propyl)-1-isopropyl-piperidine; 1-Methyl-4-{3-[4-4-phenyl-5-trifluoromethyl-1H-imidazol-2-yl)-naphthalen-1-yloxy]-propyl}-piperidine; 1-(4-Methyl-piperazin-1-yl)-3-{5-[5-methyl-4-(4-trifluoromethyl-phenyl)-1H-imidazol-2-yl]-pyridin-2-yloxy}-propan-1-one; 6-[4-(4-Chloro-phenyl)-5-methyl-1H-imidazol-2-yl]-3-fluoro-2-[4-(1-methyl-piperidin-4-yl)-butoxy]-pyridine; 1-Methyl-4-(4-{3-methyl-6-[5-methyl-4-(3-trifluoromethyl-phenyl)-1H-imidazol-2-yl]-pyridin-2-yloxyl}-butyl)-piperazine; 1-Methyl-4-{3-[4-5-methyl-4-thiophen-2-yl-1H-imidazol-2-yl)-phenoxy]-propyl}-piperidine; 2-{3-[4-1-Methyl-piperidin-4-yl)-butoxy]-phenyl}-3H-imidazo[4,5-b]pyridine; (5-Chloro-1H-indol-2-yl)-(4-methyl-piperazin-1-yl)-methanone; (5-Fluoro-1H-indol-2-yl)-(4-methyl-piperazin-1-yl)-methanone; (5-Bromo-1H-indol-2-yl)-(4-methyl-piperazin-1-yl)-methanone; (5-Methyl-1H-indol-2-yl)-(4-methyl-piperazin-1-yl)-methanone; (5,7-Difluoro-1H-indol-2-yl)-(4-methyl-piperazin-1-yl)-methanone; (7-Chloro-1H-indol-2-yl)-(4-methyl-piperazin-1-yl)-methanone; (5,7-Dichloro-1H-indol-2-yl)-(4-methyl-piperazin-1-yl)-methanone; (3,5-Dichloro-1H-indol-2-yl)-(4-methyl-piperazin-1-yl)-methanone; (6-Chloro-1H-indol-2-yl)-(4-methyl-piperazin-1-yl)-methanone; (1H-Indol-2-yl)-(3-methyl-piperazin-1-yl)-methanone; (7-Bromo-1H-indol-2-yl)-(4-methyl-piperazin-1-yl)-methanone; (5-Bromo-benzofuran-2-yl)-(4-methyl-piperazin-1-yl)-methanone; (1H-Indol-2-yl)-(4-methyl-piperazin-1-yl)-methanethione; [5-(5-Fluoro-4-methyl-1H-benzoimidazol-2-yl)-4-methyl-pyrimidin-2-yl]-[3-(1-methyl-piperidin-4-yl)-propyl]-amine; and [5-(4,6-Dimethyl-1H-benzoimidazol-2-yl)-4-methyl-pyrimidin-2-yl]-[3-(1-methyl-piperidin-4-yl)-propyl]-amine and pharmaceutically acceptable salts thereof.

In another embodiment, selective Histamine H4 antagonists are selected from those described in the international Patent Application WO2009/079001: 5-Fluoro-4-methyl-2-{4-methyl-1-[3-(1-methyl-piperidin-4-yl)-propyl]-2,3-dihydro-1H-indol-5-yl}-1H-benzoimidazole; 4,5-Dimethyl-2-{4-methyl-1-[3-(1-methyl-piperidin-4-yl)-propyl]-2,3-dihydro-1H-indol-5-yl}-1H-benzoimidazole; 2-{5-Chloro-1-[3-(1-methyl-piperidin-4-yl)-propyl]-2,3-dihydro-1H-indol-5-yl}-4,6-dimethyl-1H-benzoimidazole; 2-{4-Chloro-1-[3-(1-methyl-piperidin-4-yl)-propyl]-2,3-dihydro-1H-indol-5-yl}-5-fluoro-4-methyl-1H-benzoimidazole; 2-{4-Chloro-1-[3-(1-methyl-piperidin-4-yl)-propyl]-2,3-dihydro-1H-indol-5-yl}-1H-benzoimidazole-5-carboxylic acid methyl ester; 5-Fluoro-2-{4-fluoro-1-[3-(1-methyl-piperidin-4-yl)-propyl]-2,3-dihydro-1H-indol-5-yl}-4-methyl-1H-benzoimidazole; 5-Fluoro-4-methyl-2-{4-methyl-1-[3-(1-methyl-piperidin-4-yl)-propyl]-1H-indol-5-yl}-1H-benzoimidazole; 2-{4-Chloro-1-[3-(1-methyl-piperidin-4-yl)-propyl]-1H-indol-5-yl}-5-fluoro-4-methyl-1H-benzoimidazole; 2-{4-Chloro-1-[3-(1-methyl-pipehdin-4-yl)-propyl]-1H-indol-5-yl}-4,6-dimethyl-1H-benzoimidazole; 5-Chloro-2-{4-methyl-1-[3-(1-methyl-piperidin-4-yl)-propyl]-1H-indol-5-yl}-1H-benzoimidazole; 5-Fluoro-4-methyl-2-{1-[3-(1-methyl-piperidin-4-yl)-propyl]-1H-indol-5-yl}-1H-benzoimidazole; 4-Methyl-2-{1-[3-(1-methyl-piperidin-4-yl)-propyl]-1H-indol-5-yl}-1H-benzoimidazole; 5-Fluoro-4-methyl-2-{1-[3-(4-methyl-piperazin-1-yl)-propyl]-1H-indol-5-yl}-1H-benzoimidazole; 2-{2,3-Dimethyl-1-[3-(1-methyl-piperidin-4-yl)-propyl]-1H-indol-5-yl}-4,6-dimethyl-1H-benzoimidazole; 2-{2,3-Dimethyl-1-[3-(1-methyl-piperidin-4-yl)-propyl]-1H-indol-5-yl}-5-fluoro-4-methyl-1H-benzoimidazole; 5-Fluoro-4-methyl-2-{1-[4-(1-methyl-piperidin-4-yl)-butyl]-1H-indol-4-yl}-1H-benzoimidazole; 4-Chloro-2-{1-[4-(1-methyl-piperidin-4-yl)-butyl]-1H-indol-4-yl}-1H-benzoimidazole; 2-{1-[4-(1-Methyl-piperidin-4-yl)-butyl]-1H-indol-4-yl}-5-trifluoromethyl-1H-benzoimidazole; 6-{1-[4-(1-Methyl-piperidin-4-yl)-butyl]-1H-indol-4-yl}-5H-[1,3]dioxolo[4',5:4,5]benzo[1,2-d]imidazole; (2-{1-[4-(1-Methyl-piperidin-4-yl)-butyl]-1H-indol-4-yl}-1H-benzoimidazol-5-yl)-phenyl-methanone; 2-{1-[4-(1-Methyl-piperidin-4-yl)-butyl]-1H-indol-4-yl}-1H-naphtho[2,3-d]imidazole; 6-Chloro-4-methyl-2-{1-[4-4-(1-methyl-piperidin-4-yl)-butyl]-1H-indol-4-yl}-1H-benzoimidazole; 4-Methyl-2-{1-[4-(1-methyl-piperidin-4-yl)-butyl]-1H-indol-4-yl}-1H-benzoimidazole; 5-tert-Butyl-2-{1-[4-(1-methyl-piperidin-4-yl)-butyl]-1H-indol-4-yl}-1H-benzoimidazole; 4,6-Dimethyl-2-{1-[4-(1-methyl-piperidin-4-yl)-butyl]-1H-indol-6-yl}-1H-benzoimidazole; 5-Fluoro-4-methyl-2-{1-[4(1-methyl-piperidin-4-yl)-butyl]-1H-indol-6-yl}-1H-benzoimidazole; 4-Methyl-2-{1-[4-(1-methyl-piperidin-4-yl)-butyl]-1H-indol-6-yl}-1H-benzoimidazole; 5-tert-Butyl-2-{3-chloro-1-[3(1-methyl-piperidin-4-yl)-propyl]-1H-indol-5-yl}-1H-benzoimidazole; 6-Chloro-2-{3-chloro-1-[3-(1-methyl-piperidin-4-yl)-propyl]-1H-indol-5-yl}-4-methyl-1H-benzoimidazole; 2-{3-Chloro-1-[4-(1-methyl-piperidin-4-yl)-butyl]-1H-indol-4-yl}-5-trifluoromethyl-1H-benzoimidazole; 2-{3-Chloro-1-[4-(1-methyl-piperidin-4-yl)-butyl]-1H-indol-4-yl}-5-fluoro-4-methyl-1H-benzoimidazole; 2-{3-Chloro-1-[4-(1-methyl-piperidin-4-yl)-butyl]-1H-indol-4-yl}-5,6-difluoro-1H-benzoimidazole; 5-Fluoro-4-methyl-2-[1-(3-piperazin-1-yl-propyl)-1H-indol-5-yl]-1H-benzoimidazole; 5-tert-Butyl-2-[3-chloro-1-(3-piperidin-4-yl-propyl)-1H-indol-5-yl]-1H-benzoimidazole; 5-Fluoro-4-methyl-2-[1-(4-piperidin-4-yl-butyl)-1H-indol-4-yl]-1H-benzoimidazole; 4-Chloro-2-[1-(4-piperidin-4-yl-butyl)-1H-indol-4-yl]-1H-benzoimidazole; 4,6-Dimethyl-2-[1-(4-piperidin-4-yl-butyl)-1H-indol-6-yl]-

1H-benzoimidazole; 5-Fluoro-4-methyl-2-[1-(4-piperidin-4-yl-butyl)-1H-indol-6-yl]-1H-benzoimidazole; [5-(5-tert-Butyl-1H-benzoimidazol-2-yl)-1-(4-piperidin-4-yl-butyl)-1H-indol-3-ylmethyl]-dimethyl-amine; 5-Fluoro-4-methyl-1'-[3-(1-methyl-piperidin-4-yl)-propyl]-1H,1'H-[2,5']bibenzoimidazolyl; 5-Fluoro-4-methyl-3'-[3-(1-methyl-piperidin-4-yl)-propyl]-1H,3'H-[2,5']bibenzoimidazolyl; 4-Methyl-1'-[4-(1-methyl-piperidin-4-yl)-butyl]-1H,1'H-[2,5']bibenzoimidazolyl; 4-Methyl-3I-[4-(1-methyl-piperidin-4-yl)-butyl]-1H,3'H-[2,5']bibenzoimidazolyl; 5-Fluoro-4-methyl-1'-[4-(1-methyl-piperidin-4-yl)-butyl]-1H,1'H-[2,5']bibenzoimidazolyl; 5-Fluoro-4-methyl-3'-[4-(1-methyl-piperidin-4-yl)-butyl]-1H,3'H-[2,5']bibenzoimidazolyl; 5-Fluoro-4-methyl-2-{1-[3-(1-methyl-piperidin-4-yl)-propyl]-1H-pyrrolo[2,3-b]pyridin-5-yl}-1H-benzoimidazole; 4,5-Dimethyl-2-{1-[3-(1-methyl-piperidin-4-yl)-propyl]-1H-pyrrolo[2,3-b]pyridin-5-yl}-1H-benzoimidazole; 2-{6-Chloro-1-[3(1-methyl-piperidin-4-yl)-propyl]-1H-indol-5-yl}-4,6-difluoro-1H-benzoimidazole; 2-[6-Chloro-1-(3-piperidin-4-yl-propyl)-1H-indol-5-yl]-5-fluoro-4-methyl-1H-benzoimidazole; 2-{6-Chloro-1-[3-(1-methyl-piperidin-4-yl)-propyl]-1H-indol-5-yl}-5-fluoro-4-methyl-1H-benzoimidazole; 5-Fluoro-4,4'-dimethyl-1'-[3-(1-methyl-piperidin-4-yl)-propyl]-1H,1'H-[2,5']bibenzoimidazolyl; 5,4'-Trimethyl-1'[3-(1-methyl-piperidin-4-yl)-propyl]-1H,1'H-[2,5']bibenzoimidazolyl; 4,4'-Dimethyl-1'-[3-(1-methyl-piperidin-4-yl)-propyl]-1H,1'H-[2,5]bibenzoimidazolyl; 5-Chloro-4,4'-dimethyl-1'-[3-(1-methyl-piperidin-4-yl)-propyl]-1H,1'H-[2,5']bibenzoimidazolyl; 6-Fluoro-4,4'-dimethyl-1'-[3-(1-methyl-piperidin-4-yl)-propyl]-1H,1'H-[2,5]bibenzoimidazolyl; 4,5-Dimethyl-2-[1-(3-piperidin-4-yl-propyl)-2,3-dihydro-1H-indol-5-yl]-1H-benzoimidazole; 4,6-Dimethyl-2-{4-methyl-1-[3-(1-methyl-piperidin-4-yl)-propyl]-2,3-dihydro-1H-indol-5-yl}-1H-benzoimidazole; 5-Chloro-2-{4-methyl-1-[3-(1-methyl-piperidin-4-yl)-propyl]-2,3-dihydro-1H-indol-5-yl}-1H-benzoimidazole; 6-Fluoro-4-methyl-2-{4-methyl-1-[3-(1-methyl-piperidin-4-yl)-propyl]-2,3-dihydro-1H-indol-5-yl}-1H-benzoimidazole; 2-Methyl-7-{4-methyl-1-[3(1methyl-piperidin-4-yl)-propyl]-2,3-dihydro-1H-indol-5-yl}-6H-imidazo{4',5'3,4]benzo[2,1-d]thiazole; 4,6-Dimethyl-2-{4-methyl-1-[3-(1-methyl-piperidin-4-yl)-propyl]-1H-indol-5-yl}-1H-benzoimidazole; 4,5-Dimethyl-2-[1-(3-piperazin-1-yl-propyl)-1H-indol-5-yl]-1H-benzoimidazole; 5-tert-Butyl-2-[1-(3-piperazin-1-yl-propyl)-1H-indol-5-yl]-1H-benzoimidazole; 5-Chloro-2-[1-(3-piperazin-1-yl-propyl)-1H-indol-5-yl]-1H-benzoimidazole; 5-Chloro-2-{1-[3-(4-methyl-piperazin-1-yl)-propyl]-1H-indol-5-yl}-1H-benzoimidazole; 4-Methyl-2-[1-(4-piperidin-4-yl-butyl)-1H-indol-4-yl]-1H-benzoimidazole; 5,6-Difluoro-2-{1-[4-(1-methyl-piperidin-4-yl)-butyl]-1H-indol-4-yl}-1H-benzoimidazole; 5-Chloro-2-{1-[4-(1-methyl-piperidin-4-yl)-butyl]-1H-indol-4-yl}-1H-benzoimidazole; 5-Fluoro-2-{1-[4-(1-methyl-piperidin-4-yl)-butyl]-1H-indol-4-yl}-1H-benzoimidazole; 4,6-Difluoro-2-{1-[4-(1-methyl-piperidin-4-yl)-butyl]-1H-indol-4-yl}-1H-benzoimidazole; 2-{1-[4-(1-Methyl-piperidin-4-yl)-butyl]-1H-indol-4-yl}-1H-naphtho[1,2-d]imidazole; (2-{3-Chloro-1-[4-(1-methyl-piperidin-4-yl)-butyl]-1H-indol-4-yl}-3H-benzoimidazol-4-yl)-phenyl-methanone; 2-[3-Chloro-1-(4-piperidin-4-yl-butyl)-1H-indol-4-yl]-4,5-dimethyl-1H-benzoimidazole; 2-{3-Chloro-1-[4-(1-methyl-piperidin-4-yl)-butyl]-1H-indol-4-yl}-4,5-dimethyl-1H-benzoimidazole; 2-{3-Chloro-1-[4-(1-methyl-piperidin-4-yl)-butyl]-1H-indol-4-yl}-4,5-difluoro-1H-benzoimidazole; 6-[1-(4-Piperidin-4-yl-butyl)-1H-indol-4-yl]-5H-[1.3dioxolo[4',5':4,5]-benzo[1,2-d]imidazole; Phenyl-{2-[1-(4-piperidin-4-yl-butyl)-1H-indol-4-yl]-1H-benzoimidazol-5-yl}-methanone; 4,5-Dimethyl-2-{1-4-(1-methyl-piperidin-4-yl)-butyl]-1H-indol-4-yl}-1H-benzoimidazole; 1-[3-(4-Methyl-piperazin-1-yl)-propyl]-5-[5-methyl-4-(3-trifluoromethyl-phenyl)-1H-imidazol-2-yl]-1H-indole; 5-[4-(4-Chloro-phenyl)-5-methyl-1H-imidazol-2-yl]-1-[3-(4-methyl-piperazin-1-yl)-propyl]-1H-indole; 4-Methyl-1-[3-(1-methyl-piperidin-4-yl)-propyl]-5-(4-methyl-5-propyl-1H-imidazol-2-yl)-1H-benzoimidazole; 4-Methyl-1-[3-(1-methyl-piperidin-4-yl)-propyl]-5-[4-methyl-5-(4-trifluoromethyl-phenyl)-1H-imidazol-2-yl]-1H-benzoimidazole; 5-[5(3,5-Dichloro-phenyl)-4-methyl-1H-imidazol-2-yl]-4-methyl-1-[3-(1-methyl-piperidin-4-yl)-propyl]-1H-benzoimidazole; 4-Methyl-1-[3-(1-methyl-piperidin-4-yl)-propyl]-5-(5-phenyl-4-trifluoromethyl-1H-imidazol-2-yl)-1H-benzoimidazole; 5-[5-(4-Chloro-phenyl)-4-p-tolyl-1H-imidazol-2-yl]-4-methyl-1-[3-(1-methyl-piperidin-4-yl)-propyl]-1H-benzoimidazole; {5-(5-Fluoro-4-methyl-1H-benzoimidazol-2-yl)-1-[3-(1-methyl-piperidin-4-yl)-propyl]-1H-indol-3-ylmethyl}-dimethyl-amine; 2-[3-Chloro-1-(3-piperidin-4-yl-propyl)-1H-indol-5-yl]-5-fluoro-4-methyl-1H-benzoimidazole; 2-{3-Chloro-1-[3-(1-methyl-piperidin-4-yl)-propyl]-1H-indol-5-y1}-5-fluoro-4-methyl-1H-benzoimidazole; 2-[2,3-Dimethyl-1-(3-piperidin-4-yl-propyl)-1H-indol-5-yl]-4,6-dimethyl-1H-benzoimidazole; 2-[2,3-Dimethyl-1-(3-piperidin-4-yl-propyl)-1H-indol-5-yl]-5-fluoro-4-methyl-1H-benzoimidazole; 5-Fluoro-4-methyl-2-[1-(3-piperidin-4-yl-propyl)-1H-pyrrolo[2,3-b]pyridin-5-yl]-1H-benzoimidazole; 5-tert-Butyl-2-{1-[3-(1-methyl-piperidin-4-yl)-propyl]-1H-pyrrolo[2,3-b]pyridin-5-yl]-1H-benzoimidazole; 5-Fluoro-4-methyl-2-[1-(3-piperidin-4-yl-propyl)-2,3-dihydro-1H-indol-5-yl]-1H-benzoimidazole; 5-Chloro-2-[1-(3-piperidin-4-yl-propyl)-2,3-dihydro-1H-indol-5-yl]-1H-benzoimidazole; 4-Methyl-2-[1-(3-piperidin-4-yl-propyl)-2,3-dihydro-1H-indol-5-yl]-1H-benzoimidazole; 5-Fluoro-4-methyl-2-{1-[3-(1-methyl-piperidin-4-yl)-propyl]-2,3-dihydro-1H-indol-5-yl}-1H-benzoimidazole; 5-Chloro-2-{1-[3-(1-methyl-piperidin-4-yl)-propyl]-2,3-dihydro-1H-indol-5-yl]-1H-benzoimidazole; 4-Methyl-2-{1-[3-(1-methyl-piperidin-4-yl)-propyl]-2,3-dihydro-1H-indol-5-yl]-1H-benzoimidazole; 2-[6-Chloro-1-(3-piperidin-4-yl-propyl)-1H-indol-5-yl]-4,6-difluoro-1H-benzoimidazole; 2-[6-Chloro-1-(3-piperidin-4-yl-propyl)-1H-indol-5-yl]-4,5-dimethyl-1H-benzoimidazole; 5-Chloro-2-[6-chloro-1-(3-piperidin-4-yl-propyl)-1H-indol-5-yl]-1H-benzoimidazole; 5-Chloro-2-{6-chloro-1-[3-(1-methyl-piperidin-4-yl)-propyl]-1H-indol-5-yl}-1H-benzoimidazole; 2-{6-Chloro-1-[3-(1-methyl-piperidin-4-yl)-propyl]-1H-indol-5-yl}-4,5-dimethyl-1H-benzoimidazole; 6-Chloro-4-methyl-2-[1-(4-piperidin-4-yl-butyl)-1H-indol-4-yl]-1H-benzoimidazole; 5-tert-Butyl-2-[1-(4-piperidin-4-yl-butyl)-1H-indol-4-yl]-1H-benzoimidazole; 6,7-Dimethyl-2-[1-(4-piperidin-4-yl-butyl)-1H-indol-4-yl]-1H-benzoimidazole; 4-Methyl-2-[1-(4-pipehdin-4-yl-butyl)-1H-indol-6-yl]-1H-benzoimidazole; 6-Chloro-4-methyl-2-[1-(4-piperidin-4-yl-butyl)-1H-indol-6-yl]-1H-benzoimidazole; 5-tert-Butyl-2-[1-(4-piperidin-4-yl-butyl)-1H-indol-6-yl]-1H-benzoimidazole; 4,5-Difluoro-2-[1-(4-piperidin-4-yl-butyl)-1H-indol-4-yl]-1H-benzoimidazole; 4,4'-Dimethyl-1'-(3-piperidin-4-yl-propyl)-1H,1'H-[2,5I]bibenzoimidazolyl; 6-Fluoro-4,4'-dimethyl-1'-(3-piperidin-4-yl-propyl)-1H,1'H-[2,5']bibenzoimidazolyl; 5-Chloro-4,4'-dimethyl-1'-(3-piperidin-4-yl-propyl)-1H,1'H-[2,5']bibenzoimidazolyl; 5-Fluoro-4,4'-dimethyl-1'-(3-piperidin-4-yl-propyl)-1H,1'H-[2,5']bibenzoimidazolyl; 5-Fluoro-2-[1-(4-piperidin-4-yl-butyl)-1H-indol-4-yl]-1H-benzoimidazole; 4,6-Difluoro-2-[1-(4-piperidin-4-yl-butyl)-1H-indol-4-yl]-1H- benzoimidazole; 4-Methyl-1'-(4-piperidin-4-yl-butyl)-1H,1'H-[2,5']bibenzoimidazolyl; 4,5-Dimethyl-1'-(4-piperidin-4-yl-butyl)-1H,1'H-[2,5']bibenzoimidazolyl; 5-Fluoro-1'-(4-piperidin-4-yl-butyl)-1H,1'H-[2,4']bibenzoimidazolyl; 5-Fluoro-1'-[4-(1-methyl-piperidin-4-yl)-butyl]-1H,1'H-[2,4']bibenzoimidazolyl; 4,5-Dimethyl-1'-[4-(1-methyl-piperidin-4-yl)-butyl]-1H,1'H-[2,5']bibenzoimidazolyl; 4-Methyl-3'-(4-piperidin-4-yl-butyl)-1H,3H-[2,5']bibenzoimidazolyl; 4,5-Dimethyl-3'-(4-piperidin-4-yl-butyl)-1H,3H-[2,5']bibenzoimidazolyl; 5-Fluoro-3'-(4-piperidin-4-yl-butyl)-1H,3H-[2,5']bibenzoimidazolyl; 4,5-Dimethyl-3'-[4-(1-methyl-piperidin-4-yl)-butyl]-1H,3H-[2,5']bibenzoimidazolyl; 5-Fluoro-3'-[4-(1-methyl-piperidin-4-yl)-butyl]-1H,3'H [2,5']bibenzoimidazolyl; 2-[1-(4-Piperidin-4-yl-butyl)-1H-indol-4-yl]-1H-naphtho[2,3-d]imidazole; 2-[1-(4-Piperidin-4-yl-butyl)-1H-indol-4-yl]-1H-naphtho[1,2-d]imidazole; {2-[3-Chloro-1-(4-piperidin-4-yl-butyl)-1H-indol-4-yl]-1H-benzoimidazol-5-yl}-phenyl-methanone; 2-[3-Chloro-1-(4-piperidin-4-yl-butyl)-1H-indol-4-yl]-5-trifluoromethyl-1H-benzoimidazole; 2-[3-Chloro-1-(4-piperidin-4-yl-butyl)-1H-indol-4-yl]-5,6-difluoro-1H-benzoimidazole; 2-[3-Chloro-1-(4-piperidin-4-yl-butyl)-1H-indol-4-yl]-4,5-difluoro-1H-benzoimidazole; 2-[3-Chloro-1-(4-piperidin-4-yl-butyl)-1H-indol-4-yl]-5-fluoro-4-methyl-1H-benzoimidazole; 7-[3-Chloro-1-(4-piperidin-4-yl-butyl)-1H-indol-4-yl]-2-methyl-8H-2-[3-Chloro-1-(4-piperidin-4-yl-butyl)-1H-indol-4-yl]-3H-benzoimidazole-5-carboxylic acid methyl ester; 2-{3-Chloro-1-[4-(1-methyl-piperidin-4-yl)-butyl]-1H-indol-4-yl}-3H-benzoimidazole-5-carboxylic acid methyl ester; 4,5,4'-Trimethyl-1'-(3-piperidin-4-yl-propyl)-1'H,1H-[2,5']bibenzoimidazolyl; 4,6-Dimethyl-2-[1-(4-piperidin-4-yl-butyl)-1H-indol-4-yl]-1H-benzoimidazole; 6-Chloro-2-[1-(4-piperidin-4-yl-butyl)-1H-indol-4-yl]-1H-benzoimidazole; 2-[1-(4-Piperidin-4-yl-butyl)-1H-indol-4-yl]-6-trifluoromethyl-1H-benzoimidazole; 4-Methyl-1-[3-(1-methyl-piperidin-4-yl)-propyl]-5-[4-methyl-5-(4-trifluoromethyl-phenyl)-1H-imidazol-2-yl]-1H-benzoimidazole; 5-[5-(4-Methoxy-phenyl)-4-methyl-1H-imidazol-2-yl]-4-methyl-1-[3-(1-methyl-piperidin-4-yl)-propyl]-1H-benzoimidazole; and pharmaceutically acceptable salts, prodrugs, and active metabolites thereof.

In another particular embodiment, selective Histamine H4 antagonists are selected from those described in the international Patent Application WO2009/038673: 4-(4-Methyl-piperazin-1-yl)-thieno[3,2-d]pyrimidin-2-ylamine; 4-(4-Methyl-piperazin-1-yl)-6,7,8,9-tetrahydro-benzo[4,5]thieno[3,2-d]pyrimidin-2-ylamine; 4-Piperazin-1-yl-6,7,8,9-tetrahydro-benzo[4,5]thieno[3,2-d]pyrimidin-2-ylamine; 4-[(3aR,6aR)-Hexahydropyrrolo[3,4-b]pyrrol-5(1H)-yl]-6,7,8,9-tetrahydro[1]benzothieno[3,2-d]pyrimidin-2-amine; 4-(4-Methyl-piperazin-1-yl)-6,7,8,9-tetrahydro-benzo[4,5]furo[3,2-d]pyrimidin-2-ylamine; 4-Piperazin-1-yl-6,7,8,9-tetrahydro-benzo[4,5]furo[3,2-d]pyrimidin-2-ylamine; 4-[(3aR,6aR)-Hexahydropyrrolo[3,4-b]pyrrol-5(1H)-yl]-6,7,8,9-tetrahydro[1]benzofuro[3,2-d]pyrimidin-2-amine; 4-(4-Methyl-piperazin-1-yl)-6,7,8,9-tetrahydro-benzo[4,5]furo[3,2-d]pyrimidine; 4-Piperazin-1-yl-6,7,8,9-tetrahydro-benzo[4,5]furo[3,2-d]pyrimidine; 4-(4-Methyl-piperazin-1-yl)-6,7,8,9-tetrahydro-benzo[4,5]thieno[3,2-d]pyrimidine; 4-Piperazin-1-yl-6,7,8,9-tetrahydro-benzo[4,5]thieno[3,2-d]pyrimidine; 7-Methyl-4-[(3R)-3-(methylamino)pyrrolidin-1-yl]thieno[3,2-d]pyrimidin-2-amine; 7-Methyl-4-(4-methylpiperazin-1-yl)thieno[3,2-d]pyrimidin-2-amine; 7-Bromo-4-[(3R)-3-(methylamino)pyrrolidin-1-yl]thieno[3,2-d]pyrimidin-2-amine; 6-tert-Butyl-4-(4-methylpiperazin-1-yl)thieno[3,2-d]pyrimidin-2-amine; 6-tert-Butyl-4-[(3R)-3-(methylamino)pyrrolidin-1-yl]thieno[3,2-d]pyrimidin-2-amine; 6-tert-Butyl-4-piperazin-1-ylthieno[3,2-d]pyrimidin-2-amine; 4-[(3R)-3-Aminopyrrolidin-1-yl]-6-tert-butylthieno[3,2-d]pyrimidin-2-amine; 6-tert-Butyl-4-(octahydro-6H-pyrrolo[3,4-b]pyridin-6-yl)thieno[3,2-d]pyrimidin-2-amine; 4-[(4aR,7aR)-Octahydro-6H-pyrrolo[3,4-b]pyridin-6-yl]-6,7,8,9-tetrahydro[1]benzofuro[3,2-d]pyrimidin-2-amine; 4-[(3R)-3-(Methylamino)pyrrolidin-1-yl]-6,7,8,9-tetrahydro[1]benzofuro[3,2-d]pyrimidin-2-amine; 4-(1,4-Diazepan-1-yl)-6,7,8,9-tetrahydro[1]benzofuro[3,2-d]pyrimidin-2-amine; 4-(3-Aminoazetidin-1-yl)-6,7,8,9-tetrahydro[1]benzofuro[3,2-d]pyrimidin-2-amine; 4-[(3R)-3-Aminopyrrolidin-1-yl]-6,7,8,9-tetrahydro[1]benzofuro[3,2-d]pyrimidin-2-amine; N4-(2-Aminoethyl)-6,7,8,9-tetrahydro[1]benzofuro[3,2-d]pyrimidine-2,4-diamine; 4-(3,8-Diazabicyclo[3.2.1]oct-3-yl)6,7,8,9-tetrahydro[1]benzofuro[3,2d]pyrimidin-2-amine; N-(6,7,8,9-Tetrahydro[1]benzofuro[3,2d]pyrimidin-4-yl)ethane-1,2-diamine; (3R)—N-Methyl-1-(6,7,8,9-tetrahydro[1]benzofuro[3,2-d]pyrimidin-4-yl)pyrrolidin-3-amine; N-(6,7,8,9-Tetrahydro[1]benzothieno[3,2-d]pyrimidin-4-yl)ethane-1,2-diamine; (3R)≥N-Methyl-1-(6,7,8,9-tetrahydro-tilbenzothieno[3,2d]pyrimidin-4-yl)pyrrolidin-3-amine; 4-[(3R)-3-(Methylamino)pyrrolidin-1-yl]-6,7,8,9-tetrahydro[1]benzothieno[3,2-d]pyrimidin-2-amine; 4-[(4aR,7aR)-Octahydro-6H-pyrrolo[3,4-b]pyridin-6-yl]-6,7,8,9-tetrahydro[1]benzothieno[3,2-d]pyrimidin-2-amine; 4-Hexahydropyrrolo[3,4-c]pyrrol-2(1H)-yl]-6,7,8,9-tetrahydro[1]benzothieno[3,2-d]pyrimidin-2-amine; 4-[(3S)-3-Aminopiperidin-1-yl]-6,7,8,9-tetrahydro[1]benzothieno[3,2-d]pyrimidin-2-amine; 4-[(1S,4S)-2,5-Diazabicyclo[2.2.1]hept-2-yl]-6,7,8,9-tetrahydro[1]benzothieno[3,2-d]pyrimidin-2-amine; 4-[(1R,4R)-2,5-Diazabicyclo[2.2.1]hept-2-yl]-6,7,8,9-tetrahydro[1]benzothieno[3,2-d]pyrimidin-2-amine; 4-(1,4-Diazepan-1-yl)-6,7,8,9-tetrahydro[1]benzothieno[3,2-d]pyrimidin-2-amine; (3S,4S)-1-(2-Amino-6,7,8,9-tetrahydro[1]benzothieno[3,2-d]pyrimidin-4-yl)-4-(methylamino)pyrrolidin-3-ol; 4-[(3R)-3-(Dimethylamino)pyrrolidin-1-yl]-6,7,8,9-tetrahydro[1]benzothieno[3,2-d]pyrimidin-2-amine; 4-[(3R)-3-(Ethylamino)pyrrolidin-1-yl]-6,7,8,9-tetrahydro[1]benzothieno[3,2-d]pyrimidin-2-amine; 4-[(3R)-3-(Aminomethyl)pyrrolidin-1-yl]-6,7,8,9-tetrahydro[1]benzothieno[3,2-d]pyrimidin-2-amine; 4-(3-Aminoazetidin-1-yl)-6,7,8,9-tetrahydro[1]benzothieno[3,2-d]pyrimidin-2-amine; 8-Methyl-4-(4-methylpiperazin-1-yl)-6,7,8,9-tetrahydro[1]benzothieno[3,2-d]pyrimidin-2-amine; 8-Methyl-4-[(3R)-3-(methylamino)pyrrolidin-1-yl]-6,7,8,9-tetrahydro[1]benzothieno[3,2-d]pyrimidin-2-amine; 8-Methyl-4-[(4aR,7aR)-octahydro-6H-pyrrolo[3,4-b]pyridin-6-yl]-6,7,8,9-tetrahydro[1]benzothieno[3,2-d]pyrimidin-2-amine; 4-(4-Methylpiperazin-1-yl)-7,8,9,10-tetrahydro-6H-cyclohepta[4,5]thieno[3,2-d]pyrimidin-2-amine; 4-[(3R)-3-(Methylamino)pyrrolidin-1-yl]-7,8,9,10-tetrahydro-6H-cyclohepta[4,5]thieno[3,2-d]pyrimidin-2-amine; 4-[(4aR,7aR)-Octahydro-6H-pyrrolo[3,4-b]pyridin-6-yl]-7,8,9,10-tetrahydro-6H-cyclohepta[4,5]thieno[3,2-d]pyrimidin-2-amine; 4-[4-(2-Aminoethyl)piperazin-1-yl]-6,7,8,9-tetrahydro[1]benzothieno[3,2-d]pyrimidin-2-amine; 4-[4-(1-Methylethyl)piperazin-1-yl]-6,7,8,9-tetrahydro[1]benzothieno[3,2-d]pyrimidin-2-amine; 4-(4-Ethylpiperazin-1-yl)-6,7,8,9-tetrahydro[1]benzothieno[3,2-d]pyrimidin-2-amine; 4-(Hexahydropyrrolo[1,2-a]pyrazin-2(1H)-yl)-6,7,8,9-tetrahydro[1]benzothieno[3,2-d]pyrimidin-2-amine; 4-(Octahydro-2H-pyrido[1,2-a]pyrazin-2-yl)-6,7,8,9-tetrahydro[1]benzothieno[3,2-d]pyrimidin-2-amine; 4-(5,6-Dihydro[1,2,4]triazolo[4,3-a]pyrazin-7(8H)-yl)-6,7,8,9-tetrahydro[1]benzothieno[3,2-d]pyrimidin-2-amine; 4-[(3S)-3-(Methylamino)pyrrolidin-1-yl]-6,7,8,9-tetrahydro[1]benzothieno[3,2-d]pyrimidin-2-amine; 4-[(3R)-3-Aminopyrrolidin-1-yl]-6,7,8,9-tetrahydro[1]benzothieno[3,2-d]pyrimidin-2-amine; 8,8-Difluoro-4-(4-methylpiperazin-1-yl)-6,7,8,9-tetrahydro[1]benzothieno[3,2-d]pyrimidin-2-amine; 8,8-Difluoro-4-piperazin-1-yl-6,7,8,9-tetrahydrotilbenzothieno[3,2d]pyrimidin-2-amine; 8,8-Difluoro-4-[(3R)-3-(methylamino)pyrrolidin-1-yl]-6,7,8,9-tetrahydro[1]benzothieno[3,2-d]pyrimidin-2-amine; 4-(3,8-Diaza-bicyclo[3.2.1]oct-3-yl)-8-methoxy-6,7,8,9-tetrahydro-benzo[4,5]thieno[3,2-d]pyrimidin-2-ylamine; 8-tert-Butyl-4-(4-methyl-piperazin-1-yl)-6,7,8,9-tetrahydro-benzo[4,5]thieno[3,2-d]pyrimidin-2-ylamine; 4-[1,4]Diazepan-1-yl-8-trifluoromethyl-6,7,8,9-tetrahydro-benzo[4,5]thieno[3,2-d]pyrimidin-2-ylamine; 4-(3(S)-Aminopyrrolidin-1-yl)-8-tert-butyl-6,7,8,9-tetrahydro-benzo[4,5]thieno[3,2-d]pyrimidin-2-ylamine; 4-(3,8-Diazabicyclo[3.2.1]oct-3-yl)-8-methyl-6,7,8,9-tetrahydro[1]benzofuro[3,2-d]pyrimidin-2-amine; 8-tert-Butyl-4-(3,8-diazabicyclo[3.2.1]oct-3-yl)-6,7,8,9-tetrahydro[1]benzothieno[3,2-d]pyrimidin-2-amine; 8-Methoxy-4-(4-methylpiperazin-1-yl)-6,7,8,9-tetrahydro[1]benzothieno[3,2-d]pyrimidin-2-amine; 4-[3-(Aminomethyl)azetidin-1-yl]-8-tert-butyl-6,7,8,9-tetrahydro[1]benzothieno[3,2-d]pyrimidin-2-amine; 4-(3,4-Diazabicyclo[3.2.1]oct-3-yl)-8-methyl-6,7,8,9-tetrahydro[1]benzothieno[3,2-d]pyrimidin-2-amine; 4-[(3R)-3-Aminopyrrolidin-1-yl]-8-methoxy-6,7,8,9-tetrahydro[1]benzothieno[3,2-d]pyrimidin-2-amine; 4-Piperazin-1-yl-8-(trifluoromethyl)-6,7,8,9-tetrahydro[1]benzofuro[3,2-d]pyrimidin-2-amine; 4-(4-Methylpiperazin-1-yl)-8-(trifluoromethyl)-6,7,8,9-tetrahydro[1]benzofuro[3,2-d]pyrimidin-2-amine; 8-tert-Butyl-4-(4-methylpiperazin-1-yl)-6,7,8,9-tetrahydro[1]benzofuro[3,2-d]pyrimidin-2-amine; 8-Methyl-4-piperazin-1-yl-6,7,8,9-tetrahydro[1]benzofuro[3,2-d]pyrimidin-2-amine; 8-Methyl-4-(4-methylpiperazin-1-yl)-6,7,8,9-tetrahydro[1]benzofuro[3,2-d]pyrimidin-2-amine; 6,6-Dimethyl-4-(4-methylpiperazin-1-yl)-6,7,8,9-tetrahydro[1]benzothieno[3,2-d]pyrimidin-2-amine; 4-(1,4-Diazepan-1-yl)-8-methoxy-6,7,8,9-tetrahydro[1]benzothieno[3,2-d]pyrimidin-2-amine; 8-tert-Butyl-4-[(3R)-3-(methylamino)pyrrolidin-1-yl]-6,7,8,9-tetrahydro[1]benzofuro[3,2-d]pyrimidin-2-amine; 4-[(3R)-3-(Methylamino)pyrrolidin-1-yl]-8-(trifluoromethyl)-6,7,8,9-tetrahydro[1]benzofuro[3,2-d]pyrimidin-2-amine; 4-[(3S)-3-Aminopyrrolidin-1-yl]-8-methoxy-6,7,8,9-tetrahydro[1]benzothieno[3,2-d]pyrimidin-2-amine; 8-Methoxy-4-[(3R)-3-(methylamino)pyrrolidin-1-yl]-6,7,8,9-tetrahydro[1]benzothieno[3,2-d]pyrimidin-2-amine; 4-[(3R)-3-Aminopyrrolidin-1-yl]-8-(trifluoromethyl)-6,7,8,9-tetrahydro[1]benzothieno[3,2-d]pyrimidin-2-amine; 4-[(3R)-3-Aminopyrrolidin-1-yl]-8-(trifluoromethyl)-6,7,8,9-tetrahydro[1]benzofuro[3,2-d]pyrimidin-2-amine; 4-[(3S)-3-Aminopyrrolidin-1-yl]-8-(trifluoromethyl)-6,7,8,9-tetrahydro[1]benzofuro[3,2-d]pyrimidin-2-amine; 4-[(3R)-3-Aminopyrrolidin-1-yl]-8-methyl-6,7,8,9-tetrahydro[1]benzothieno[3,2-d]pyrimidin-2-amine; 4-[(3S)-3-Aminopyrrolidin-1-yl]-8-methyl-6,7,8,9-tetrahydro[1]benzothieno[3,2-d]pyrimidin-2-amine; 4-[3-(Aminomethyl)azetidin-1-yl]-8-methoxy-6,7,8,9-tetrahydro[1]benzothieno[3,2-d]pyrimidin-2-amine; 4-[(3S)-3-Aminopyrrolidin-1-yl]-6,6-dimethyl-6,7,8,9-tetrahydro[1]benzofuro[3,2-d]pyrimidin-2-amine; 4-[(3R)-3-Aminopyrrolidin-1-yl]-6,6-dimethyl-6,7,8,9-tetrahydro[1]benzofuro[3,2-d]pyrimidin-2-amine; 6,6-Dimethyl-4-[(3R)-3-(methylamino)pyrrolidin-1-yl]-6,7,8,9-tetrahydro[1]benzofuro[3,2-d]pyrimidin-2-amine; 4-[3-(Aminomethyl)azetidin-1-yl]-6,6-dimethyl-6,7,8,9-tetrahydro[1]benzofuro[3,2-d]pyrimidin-2-amine; 6,6-Dimethyl-4-[(3aR,6aS)-5-methylhexahydropyrrolo[3,4-c]pyrrol-2(1H)-yl]-6,7,8,9-tetrahydrorribenzothieno[3,2-d]pyrimidin-2-amine; 8-tert-Butyl-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine; 4-[(3aR,6aS)-5-Methylhexahydropyrrolo[3,4-c]pyrrol-2(1H)-yl]-8-(trifluoromethyl)-6,7,8,9-tetrahydro[1]benzothieno[3,2-d]pyrimidin-2-amine; tetrahydro[1]benzothieno[3,2-d]pyrimidin-2-amine; tetrahydro[1]benzofuro[3,2-d]pyrimidin-2-amine; 8-Methoxy-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine; 4-[(3aR,6aS)-5-Methylhexahydropyrrolo[3,4-c]pyrrol-2(1H)-yl]-8-(trifluoromethyl)-6,7,8,9-tetrahydro[1]benzofuro[3,2-d]pyrimidin-2-amine; 8-Methyl-4-[(3ar,6aS)-5-methylhexahydropyrrol[3,4-c]pyrrol-2(1H)-yl]-6,7,8,9-tetrahydro[1]benzofuro[3,2-d]pyrimidin-2-amine; 4-(1,4-Diazepan-1-yl)-6,6-dimethyl-6,7,8,9-tetrahydro[1]benzofuro[3,2-d]pyrimidin-2-amine; 6,6-Dimethyl-4-piperazin-1-yl-6,7,8,9-tetrahydro[1]benzofuro[3,2-d]pyrimidin-2-amine; 6,6-Dimethyl-4-(4-methylpiperazin-1-yl)-6,7,8,9-tetrahydro[1]benzofuro[3,2-d]pyrimidin-2-amine; N4-(2-Aminoethyl)-N4,6,6-trimethyl-6,7,8,9-tetrahydro[1]benzothieno[3,2-d]pyrimidine-2,4-diamine; N4-(2-Aminoethyl)-N4,6,6-trimethyl-6,7,8,9-tetrahydro[1]benzofuro[3,2-d]pyrimidine-2,4-diamine; N4-(2-Aminoethyl)-8-methoxy-N4-methyl-6,7,8,9-tetrahydro[1]benzothieno[3,2-d]pyrimidine-2,4-diamine; N4-(2-Aminoethyl)-8-methoxy-N4-methyl-6,7,8,9-tetrahydro[1]benzofuro[3,2-d]pyrimidine-2,4-diamine; N4-(2-Aminoethyl)-8-tert-butyl-N4-methyl-6,7,8,9-tetrahydro[1]benzothieno[3,2-d]pyrimidine-2,4-diamine; N4-(2-Aminoethyl)-8-tert-butyl-N4-methyl-6,7,8,9-tetrahydro[1]benzofuro[3,2-]pyrimidine-2,4-diamine; N4-(2-Aminoethyl)-N4-methyl-8-(trifluoromethyl)-6,7,8,9-tetrahydro[1]benzothieno[3,2-d]pyrimidine-2,4-diamine; N4-(2-Aminoethyl)-N4-methyl-8-(trifluoromethyl)-6,7,8,9-tetrahydro[1]benzofuro[3,2-d]pyrimidine-2,4-diamine; N4-(2-Aminoethyl)-N4,8-dimethyl-6,7,8,9-tetrahydro[1]benzothieno[3,2-d]pyrimidine-2,4-diamine; N4-(2-Aminoethyl)-N4,8-dimethyl-6,7,8,9-tetrahydro[1]benzofuro[3,2-d]pyrimidine-2,4-diamine; 8,8-Difluoro-4-[(3S)-3-(methylamino)pyrrolidin-1-yl]-6,7,8,9-tetrahydro[1]benzothieno[3,2-d]pyrimidin-2-amine; 4-[(3R)-3-Aminopyrrolidin-1-yl]-8,8-difluoro-6,7,8,9-tetrahydro[1]benzothieno[3,2-d]pyrimidin-2-amine; 4-(1,4-Diazepan-1-yl)-8,8-difluoro-6,7,8,9-tetrahydro[1]benzothieno[3,2-d]pyrimidin-2-amine; N4-(2-Aminoethyl)-8,8-difluoro-N4-methyl-6,7,8,9-tetrahydro[1]benzothieno[3,2-d]pyrimidine-2,4-diamine; 8,8-Difluoro-4-[(3R)-3-(methylamino)pyrrolidin-1-yl]-6,7,8,9-tetrahydro[1]benzofuro[3,2-d]pyrimidin-2-amine; 4-[(3R)-3-Aminopyrrolidin-1-yl]-8,8-difluoro-6,7,8,9-tetrahydro[1]benzofuro[3,2-d]pyrimidin-2-amine; 8,8-Difluoro-4-piperazin-1-yl-6,7,8,9-tetrahydro[1]benzofuro[3,2-d]pyrimidin-2-amine; 4-[(3S)-3-Aminopyrrolidin-1-yl]-8,8-difluoro-6,7,8,9-tetrahydro[1]benzothieno[3,2-d]pyrimidin-2-amine; 4-(3-Aminoazetidin-1-yl)-8,8-difluoro-6,7,8,9-tetrahydro[1]benzofuro[3,2-d]pyrimidin-2-amine; 8,8-Difluoro-4-[(3S)-3-(methylamino)pyrrolidin-1-yl]-6,7,8,9-tetrahydro[1]benzofuro[3,2-d]pyrimidin-2-amine; 8,8-Difluoro-4-(4-methylpiperazin-1-yl)-6,7,8,9-tetrahydro[1]benzofuro[3,2-d]pyrimidin-2-amine; 4-((R,R)-octahydropyrrolo[3,4-b]pyridin-6-yl)-8,8-difluoro-6,7,8,9-tetrahydro[1]benzofuro[3,2-d]pyrimidin-2-amine; N4-(2-Aminoethyl)-8,8-difluoro-N4-methyl-6,7,8,9-tetrahydro[1]benzofuro[3,2-d]pyrimidine-2,4-diamine; 4-[(3S)-3-

Aminopyrrolidin-1-yl]-8,8-difluoro-6,7,8,9-tetrahydro[1]
benzofuro[3,2-d]pyrimidin-2-amine; 4-(3-Aminoazetidin-1-
yl)-8,8-difluoro-6,7,8,9-tetrahydro[1]benzofuro[3,2-d]
pyrimidin-2-amine; N4-(2-Aminoethyl)-8,8-difluoro-6,7,8,
9-tetrahydro[1]benzothieno[3,2-d]pyrimidine-2,4-diamine;
8,8-Difluoro-4-[(3aR,6aS)-hexahydropyrrolo[3,4-c]pyrrol-
2(1H)-yl]-6,7,8,9-tetrahydro[1]benzothieno[3,2-d]pyrimi-
din-2-amine; 4-(1,4-Diazepan-1-yl)-8,8-difluoro-6,7,8,9-
tetrahydro[1]benzofuro[3,2-d]pyrimidin-2-amine; 8,8-
Dimethyl-4-(4-methylpiperazin-1-yl)-6,7,8,9-tetrahydro[1]
benzothieno[3,2-d]pyrimidin-2-amine; 4-(1,4-Diazepan-1-
yl)-8,8-dimethyl-6,7,8,9-tetrahydro[1]benzothieno[3,2-d]
pyrimidin-2-amine; N4-(2-Aminoethyl)-N4,8,8-trimethyl-6,
7,8,9-tetrahydro[1]benzothieno[3,2-d]pyrimidine-2,4-
diamine; 8,8-Dimethyl-4-[(3R)-3-(methylamino)pyrrolidin-
1-yl]-6,7,8,9-tetrahydro[1]benzothieno[3,2-d]pyrimidin-2-
amine; 8,8-Dimethyl-4-[(3S)-3-(methylamino)pyrrolidin-1-
yl]-6,7,8,9-tetrahydro[1]benzothieno[3,2-d]pyrimidin-2-
amine; 4-[(3R)-3-Aminopyrrolidin-1-yl]-8,8-dimethyl-6,7,
8,9-tetrahydro[1]benzothieno[3,2-d]pyrimidin-2-amine;
8,8-Dimethyl-4-[(3R)-3-(methylamino)pyrrolidin-1-yl]-6,7,
8,9-tetrahydro[1]benzofuro[3,2-d]pyrimidin-2-amine; 4-(4-
Methylpiperazin-1-yl)-8-(trifluoromethyl)-6,7,8,9-tetra-
hydro[1]benzothieno[3,2-d]pyrimidin-2-amine; 4-[(3R)-3-
Aminopyrrolidin-1-yl]-8-tert-butyl-6,7,8,9-tetrahydro[1]
benzothieno[3,2-d]pyrimidin-2-amine; 8-Methyl-4-[(3R)-3-
(methylamino)pyrrolidin-1-yl]-6,7,8,9-tetrahydro[1]
benzofuro[3,2-d]pyrimidin-2-amine; 4-[(3R)-3-
(Methylamino)pyrrolidin-1-yl]-8-(trifluoromethyl)-6,7,8,9-
tetrahydro[1]benzothieno[3,2-d]pyrimidin-2-amine; 8-tert-
Butyl-4-[(3R)-3-(methylamino)pyrrolidin-1-yl]-6,7,8,9-
tetrahydro[1]benzothieno[3,2-d]pyrimidin-2-amine; 4-[3-
(Aminomethyl)azetidin-1-yl]-8-methyl-6,7,8,9-tetrahydro
[1]benzothieno[3,2-d]pyrimidin-2-amine; 4-[(3R)-3-
Aminopyrrolidin-1-yl]-8-methyl-6,7,8,9-tetrahydro[1]
benzofuro[3,2-d]pyrimidin-2-amine; 4-(1,4-Diazepan-1-yl)-
8-methyl-6,7,8,9-tetrahydro[1]benzofuro[3,2-d]pyrimidin-
2-amine; 8-Methyl-4-piperazin-1-yl-6,7,8,9-tetrahydro[1]
benzothieno[3,2-d]pyrimidin-2-amine; 4-(3,8-Diazabicyclo
[3.2.1]oct-3-yl)-8-(trifluoromethyl)-6,7,8,9-tetrahydro[1]
benzothieno[3,2-d]pyrimidin-2-amine; 4-Piperazin-1-yl-8-
(trifluoromethyl)-6,7,8,9-tetrahydro[1]benzothieno[3,2-d]
pyrimidin-2-amine; 4-(1,4-Diazepan-1-yl)-8-methyl-6,7,8,
9-tetrahydro[1]benzothieno[3,2-d]pyrimidin-2-amine;
8-Methoxy-4-piperazin-1-yl-6,7,8,9-tetrahydro[1]benzoth-
ieno[3,2-d]pyrimidin-2-amine; 4-(3,8-Diazabicyclo[3.2.1]
oct-3-yl)-6,6-dimethyl-6,7,8,9-tetrahydro[1]benzofuro[3,2-
d]pyrimidin-2-amine; and pharmaceutically acceptable
salts, prodrugs, and active metabolites thereof.

In another embodiment, selective Histamine H4 antago-
nists are selected from those described in the international
Patent Application WO2008/100565: 4-Cyclopentyl-6-(4-
methyl-piperazin-1-yl)-pyrimidin-2-ylamine; 4-Cyclopen-
tyl-6-(4-methyl-piperazin-1-yl)-pyrimidin-2-ylamine; (R)-
4-(3-Amino-piperidin-1-yl)-6-cyclopentyl-pyrimidin-2-
ylamine; (R)-4-Cyclopentyl-6-(3-methylamino-pyrrolidin-
1-yl)-pyrimidin-2-ylamine; trans-1-(2-Amino-6-
cyclopentyl-pyrimidin-4-yl)-4-methylamino-pyrrolidin-3-
ol; 4-Cyclopentyl-6-(cis-hexahydro-pyrrolo[3,4-b]pyrrol-5-
yl)-pyrimidin-2-ylamine; 4-Cyclopentyl-6-(cis-octahydro-
pyrrolo[3,4-b]pyridin-6-yl)-pyrimidin-2-ylamine;
4-Isopropyl-6-piperazin-1-yl-pyrimidin-2-ylamine; (R)-4-
(3-Amino-piperidin-1-yl)-6-isopropyl-pyrimidin-2-ylam-
ine; (S)-4-(3-Amino-piperidin-1-yl)-6-isopropyl-pyrimidin-
2-ylamine; (R)-4-Isopropyl-6-(3-methylamino-pyrrolidin-1-
yl)-pyrimidin-2-ylamine; (R)-4-(3-Amino-pyrrolidin-1-yl)-
6-isopropyl-pyrimidin-2-ylamine; trans-1-(2-Amino-6-
isopropyl-pyrimidin-4-yl)-4-methylamino-pyrrolidin-3-ol.;
(S,S)-4-(2,5-Diaza-bicyclo[2.2.1]hept-2-yl)-6-isopropyl-py-
rimidin-2-ylamine; (R; R)-4-(2,5-Diaza-bicyclo[2.2.1]hept-
2-yl)-6-isopropyl-pyrimidin-2-ylamine; 4-(cis-Hexahydro-
pyrrolo[3,4-b]pyrrol-5-yl)-6-isopropyl-pyrimidin-2-
ylamine; (R, R)-4-(Hexahydro-pyrrolo[3,4-b]pyrrol-5-yl)-6-
isopropyl-pyrimidin-2-ylamine; 4-Isopropyl-6-(cis-5-
methyl-hexahydro-pyrrolo[3,4-c]pyrrol-2-yl)-pyrimidin-2-
ylamine; 4-Isopropyl-6-(cis-octahydro-pyrrolo[3,4-b]
pyridin-6-yl)-pyrimidin-2-ylamine; (R, R)-4-Isopropyl-6-
(cis-octahydro-pyrrolo[3,4-b]pyridin-6-yl)-pyrimidin-2-
ylamine; (R)-4-Methyl-6-(3-methylamino-pyrrolidin-1-yl)-
pyrimidin-2-ylamine; 4-Methyl-6-(cis-octahydro-pyrrolo[3,
4-b]pyridin-6-yl)-pyrimidin-2-ylamine; 4,5-Dimethyl-6-
piperazin-1-yl-pyrimidin-2-ylamine; 4,5-Dimethyl-6-(4-
methyl-piperazin-1-yl)-pyrimidin-2-ylamine; (R)-4-(3-
Amino-pyrrolidin-1-yl)-5,6-dimethyl-pyrimidin-2-ylamine;
(R)-4,5-Dimethyl-6-(3-methylamino-pyrrolidin-1-yl)-py-
rimidin-2-ylamine; 4-(cis-Hexahydro-pyrrolo[3,4-b]pyrrol-
5-yl)-5,6-dimethyl-pyrimidin-2-ylamine; 4,5-Dimethyl-6-
(cis-5-methyl-hexahydro-pyrrolo[3,4-c]pyrrol-2-yl)-
pyrimidin-2-ylamine; 4, 5-Dimethyl-6-(cis-octahydro-
pyrrolo[3,4-b]pyridin-6-yl)-pyrimidin-2-ylamine; (S,S)-4-
(2,5-Diaza-bicyclo[2.2.1]hept-2-yl)-5,6-dimethyl-
pyrimidin-2-ylamine; (R)-4-(3-Amino-pyrrolidin-1-yl)-6-
ethyl-pyrimidin-2-ylamine; (R)-4-Ethyl-6-(3-methylamino-
pyrrolidin-1-yl)-pyrimidin-2-ylamine; (R,R)-(4-Ethyl-6-
hexahydro-pyrrolo[3,4-b]pyrrol-5-yl)-pyrimid in-2-
ylamine; 4-Ethyl-6-(c/s-hexahydro-pyrrolo[3,4-c]pyrrol-2-
yl)-pyrimidin-2-ylamine; (R, R)-(4-Ethyl-6-octahydro-
pyrrolo[3,4-b]pyridin-6-yl)-pyrimidin-2-ylamine;
4-Cyclopropyl-6-(4-methyl-piperazin-1-yl)-pyrimidin-2-
ylamine; (R)-4-Cyclopropyl-6-3-methylamino-pyrrolidin-1-
yl)-pyrimidin-2-ylamine; 4-Cyclopropyl-6-(cis-octahydro-
pyrrolo[3,4-b]pyridin-6-yl)-pyrimidin-2-ylamine;
4-Cyclobutyl-6-piperazin-1-yl-pyrimidin-2-ylamine; 4-Cy-
clobutyl-6-(4-methyl-piperazin-1-yl)-pyrimidin-2-ylamine;
(R)-4-(3-Amino-piperidin-1-yl)-6-cyclobutyl-pyrimidin-2-
ylamine; (R)-4-Cyclobutyl-6-(3-methylamino-pyrrolidin-1-
yl)-pyrimidin-2-ylamine; 4-Cyclobutyl-6-(cis-hexahydro-
pyrrolo[3,4-b]pyrrol-5-yl)-pyrimidin-2-ylamine;
4-Cyclobutyl-6-(cis-hexahydro-pyrrolo[3,4-c]pyrrol-2-yl)-
pyrimidin-2-ylamine; 4-Cyclobutyl-6-(cis-5-methyl-hexa-
hydro-pyrrolo[3,4-c]pyrrol-2-yl)-pyrimidin-2-ylamine;
4-Cyclobutyl-6-(cis-octahydro-pyrrolo[3,4-b]pyridin-6-yl)-
pyrimidin-2-ylamine; (R, R)-(4-Cyclobutyl-6-cis-octa-
hydro-pyrrolo[3,4-b]pyridin-6-yl)-pyrimidin-2-ylamine;
4-Cyclohexyl-6-(4-methyl-piperazin-1-yl)-pyrimidin-2-
ylamine; (R)-(4-Cyclohexyl-6-3-methylamino-pyrrolidin-1-
yl)-pyrimidin-2-ylamine; 4-Cyclohexyl-6-(cis-hexahydro-
pyrrolo[3,4-b]pyrrol-5-yl)-pyrimidin-2-ylamine; (R, R)-4-
Cyclohexyl-6-(octahydro-pyrrolo[3,4-b]pyridin-6-yl)-
pyrimidin-2-ylamine; 4-Piperazin-1-yl-6-(tetrahydro-furan-
3-yl)-pyrimidin-2-ylamine; 4-(4-Methyl-piperazin-1-yl)-6-
(tetrahydro-furan-3-yl)-pyrimidin-2-ylamine; 4-Piperazin-
1-yl-6-(tetrahydro-pyran-4-yl)-pyrimidin-2-ylamine; 4-(4-
Methyl-piperazin-1-yl)-6-(tetrahydro-pyran-4-yl)-
pyrimidin-2-ylamine; (R)-4-(3-Methylamino-pyrrolidin-1-
yl)-6-(tetrahydro-pyran-4-yl)-pyrimidin-2-ylamine; (R,R)-
4-(Octahydro-pyrrolo[3,4-b]pyridin-6-yl)-6-(tetrahydro-
pyran-4-yl)-pyrimidin-2-ylamine; 4-Benzyl-6-piperazin-1-
yl-pyrimidin-2-ylamine; 4-Benzyl-6-(4-methyl-piperazin-1-
yl)-pyrimidin-2-ylamine; (R)-Benzyl-6-(3-methylamino-
pyrrolidin-1-yl)-pyrimidin-2-ylamine; (R,R)-4-Benzyl-6-
(octahydro-pyrrolo[3,4-b]pyridin-6-yl)-pyrimidin-2-
ylamine; 4-(4-Methyl-piperazin-1-yl)-5,6,7,8-tetrahydro-
quinazolin-2-ylamine; 4-(4-Piperazin-1-yl)-5,6,7,8- tetrahydro-quinazolin-2-ylamine; (R)-4-(3-Amino-pyrrolidin-1-yl)-5,6,7,8-tetrahydro-quinazolin-2-ylamine; (R)-4-(3-Methylamino-pyrrolidin-1-yl)-5,6,7,8-tetrahydro-quinazolin-2-ylamine; (R,R)-4-(Hexahydro-pyrrolo[3,4-b]pyrrol-5-yl)-5A7,8-tetrahydro-quinazolin-2-ylamine; 4-(cis-Octahydro-pyrrolo[3,4-b]pyridin-6-yl)-5,6,7,8-tetrahydro-quinazolin-2-ylamine; (R, R)-4-(Octahydro-pyrrolo[3,4-b]pyridin-6-yl)-5,6,7,8-tetrahydro-quinazolin-2-ylamine; (S,S)-4-(2,5-Diaza-bicyclo[2.2.1]hept-2-yl)-5,6,7,8-tetrahydro-quinazolin-2-ylamine; 4-(4-Methyl-piperazin-1-yl)-6,7-dihydro-5H-cyclopentapyrimidin-2-ylamine; (R,R)-4-(4-Methylamino-pyrrolidin-1-yl-6,7-dihydro -5H-cyclopentapyrimidin-2-ylamine; 4-tert-Butyl-6-piperazin-1-yl-pyrimidin-2-ylamine; 4-tert-Butyl-6-(4-methyl-piperazin-1-yl)-pyrimidin-2-ylamine; (R)-4-tert-Butyl-6-(3-methylamino-pyrrolidin-1-yl)-pyrimidin-2-ylannine; (R, R)-4-tert-Butyl-6-(octahydro-pyrrolo[3,4-b]pyridin-6-yl)-pyrimidin-2-ylamine; (R)-4-(3-Amino-pyrrolidin-1-yl)-6-cyclopentyl-pyrimidin-2-ylamine; (R,R)-4-Cyclopentyl-6-(octahydro-pyrrolo[3,4-b]pyridin-6-yl)-pyrimidin-2-ylamine; 4-Cyclopentyl-6-(cis-5-methyl-hexahydro-pyrrolo[3,4-c]pyrrol-2-yl)-pyrimidin-2-ylamine; (R,R)-4-Cyclopentyl-6-(hexahydro-pyrrolo[3,4-b]pyrrol-5-yl)-pyrimidin-2-ylamine; 4-Cyclopentyl-6-(cis-1,7-diaza-spiro[4.4]non-7-yl)-pyrimidin-2-ylamine; 4-(3-Amino-azetidin-1-yl)-6-cyclopentyl-pyrimidin-2-ylamine; 4-Cyclopentyl-6-(trans-hexahydro-pyrrolo[3,4-b][1,4]oxazin-6-yl)-pyrimidin-2-ylamine; 4-Cyclopentyl-6-(hexahydro-pyrrolo[3,4-c]pyrrol-2-yl)-pyrimidin-2-ylamine; 4-Cyclopentyl-6-(cis-hexahydro-pyrrolo[3,4-b][1,4]oxazin-6-yl)-pyrimidin-2-ylamine; (2-Amino-ethyl)-6-isopropyl-pyrimidine-2,4-diamine; 4-(3-Amino-azetidin-1-yl)-6-isopropyl-pyrimidin-2-ylamine; 4-(1,7-Diaza-spiro[4.4]non-7-yl)-6-isopropyl-pyrimidin-2-ylamine; N4-(2-Amino-ethyl)-6-isopropyl-N4-methyl-pyrimidine-2,4-diamine; 4-(cis-Hexahydro-pyrrolo[3,4-b][1,4]oxazin-6-yl)-6-isopropyl-pyrimidin-2-ylamine; 4-(trans-Hexahydro-pyrrolo[3,4-b][1,4]oxazin-6-yl)-6-isopropyl-pyrimidin-2-ylamine; 4-Isopropyl-6-(4-methyl-piperazin-1-yl)-pyrimidin-2-ylamine; 4-(4-Methyl-piperazin-1-yl)-7,8-dihydro-5H-pyrano[4,3-d]pyrimidin-2-ylamine; (R,R)-4-(Octahydro-pyrrolo[3,4-b]pyridin-6-yl)-7,8-dihydro-5H-pyrano[4,3-d]pyrimidin-2-ylamine; (R)-4-(3-Amino-pyrrolidin-1-yl)-7,8-dihydro-5H-pyrano[4,3-d]pyrimidin-2-ylamine; (R)-4-(3-Methylamino-pyrrolidin-1-yl)-7,8-dihydro-5H-pyrano[4,3-d]pyrimidin-2-ylamine; 4-Piperazin-1-yl-7,8-dihydro-5H-pyrano[4,3-d]pyrimidin-2-ylamine; 4-Butyl-5-methoxy-6-piperazin-1-yl-pyrimidin-2-ylamine; 4-Butyl-6-[1,4]diazepan-1-yl-5-methoxy-pyrimidin-2-ylamine; 4-(3-Amino-azetidin-1-yl)-6-butyl-5-methoxy-pyrimidin-2-ylamine; (R)-4-(3-Amino-pyrrolidin-1-yl)-6-butyl-5-methoxy-pyrimidin-2-ylamine; (S)-4-(3-Amino-pyrrolidin-1-yl)-6-butyl-5-methoxy-pyrimidin-2-ylamine; (R)-4-Butyl-5-methoxy-6-(3-methylamino-pyrrolidin-1-yl)-pyrimidin-2-ylamine; (S)-4-Butyl-5-methoxy-6-(3-methylamino-pyrrolidin-1-yl)-pyrimidin-2-ylamine; 4-Butyl-5-methoxy-6-(4-methyl-piperazin-1-yl)-pyrimidin-2-ylamine; $N^4$-(2-Amino-ethyl)-6-butyl-5-methoxy-N4-methyl-pyrimidine-2,4-diamine; $N^4$-(2-Amino-ethyl)-6-butyl-5-methoxy-pyrimidine-2,4-diamine; 4-(3-Amino-azetidin-1-yl)-6-cyclopentyl-5-methoxy-pyrimidin-2-ylamine; 4-Cyclopentyl-6-[1,4]diazepan-1-yl-5-methoxy-pyrimidin-2-ylamine; (R)-4-(3-Amino-pyrrolidin-1-yl)-6-cyclopentyl-5-methoxy-pyrimid in-2-ylamine; (S)-4-Cyclopentyl-5-methoxy-6-(3-methylamino-pyrrolidin-1-yl)-pyrimidin-2-ylamine; $N^4$-(2-Amino-ethyl)-6-cyclopentyl-5-methoxy-$N^4$-methyl-pyrimidine-2,4-diamine; N4-(2-Amino-ethyl)-6-cyclopentyl-5-methoxy-pyrimidine-2I4-diamine; 4-[1,4]Diazepan-1-yl-6-methoxymethyl-pyrimidin-2-ylamine; (S)-4-(3-Amino-pyrrolidin-1-yl)-6-methoxymethyl-pyrimidin-2-ylamine; (S)-4-Methoxymethyl-6-(3-methylamino-pyrrolidin-1-yl)-pyrimidin-2-ylamine; 4-Cyclopropyl-6-(cis-5-methyl-hexahydro-pyrrolo[3,4-c]pyrrol-2-yl)-pyrimidin-2-ylamine; 4-Cyclopropyl-6-piperazin-1-yl-pyrimidin-2-ylamine; 4-(3-Amino-azetidin-1-yl)-6-cyclopropyl-pyrimidin-2-ylamine; (R)-4-(3-Amino-pyrrolidin-1-yl)-6-cyclopropyl-pyrimidin-2-ylamine; 4-Cyclopropyl-6-(cis-hexahydro-pyrrolo[3,4-c]pyrrol-2-yl)-pyrimidin-2-ylamine; (S)-4-Isopropyl-6-(3-methylamino-pyrrolidin-1-yl)-pyrimidin-2-ylamine; (S)-4-(3-Amino-pyrrolidin-1-yl)-6-isopropyl-pyrimidin-2-ylamine; (R)-4-(3-Amino-pyrrolidin-1-yl)-6-tert-butyl-pyrimidin-2-ylamine; 4-tert-Butyl-6-(cis-5-methyl-hexahydro-pyrrolo[3,4-c]pyrrol-2-yl)-pyrimidin-2-ylamine; (S)-4-(3-Amino-pyrrolidin-1-yl)-6-tert-butyl-pyrimidin-2-ylamine; (S)-4-tert-Butyl-6-(3-methylamino-pyrrolidin-1-yl)-pyrimidin-2-ylamine; N4-(2-Amino-ethyl)-6-tert-butyl-N4-methyl-pyrimidine-2,4-diamine; 4-tert-Butyl-6-(cis-hexahydro-pyrrolo[3,4-c]pyrrol-2-yl)-pyrimidin-2-ylamine; 4-(3-Amino-azetidin-1-yl)-6-tert-butyl-pyrimidin-2-ylamine; 4-tert-Butyl-6-(3,8-diaza-bicyclo[3.2.1]oct-3-yl)-pyrimidin-2-ylamine; (R)-4-(3-Amino-pyrrolidin-1-yl)-6-butyl-pyrimidin-2-ylamine; 4-Butyl-6-(4-methyl-piperazin-1-yl)-pyrimidin-2-ylamine; (R)-4-Butyl-6-(3-methylamino-pyrrolidin-1-yl)-pyrimidin-2-ylamine; N4-(2-Amino-ethyl)-6-butyl-$N^4$-methyl-pyrimidine-2,4-diamine; 4-Butyl-6-(cis-5-methyl-hexahydro-pyrrolo[3,4-c]pyrrol-2-yl)-pyrimidin-2-ylamine; Butyl-6-(cis-hexahydro-pyrrolo[3,4-c]pyrrol-2-yl)-pyrimidin-2-ylamine; 4-B utyl-6-(cis-octahydro-pyrrolo[3,4-b]pyridin-6-yl)-pyrimidin-2-ylamine; 4-Butyl-6-piperazin-1-yl-pyrimidin-2-ylamine; 4-Butyl-6-(3,8-diaza-bicyclo[3.2.1]oct-3-yl)-pyrimidin-2-ylamine; 4-(4-Methyl-piperazin-1-yl)-6-propyl-pyrimidin-2-ylamine; 4-(cis-5-Methyl-hexahydro-pyrrolo[3,4-c]pyrrol-2-yl)-6-propyl-pyrimidin-2-ylamine; 4-Isobutyl-6-(4-methyl-piperazin-1-yl)-pyrimidin-2-ylamine; 4-Isobutyl-6-piperazin-1-yl-pyrimidin-2-ylamine; (R)-4-Isobutyl-6-(3-methylamino-pyrrolidin-1-yl)-pyrimidin-2-ylamine; (R)-4-(3-Amino-pyrrolidin-1-yl)-6-isobutyl-pyrimidin-2-ylamine; (S)-4-Ethyl-6-(3-methylamino-pyrrolidin-1-yl)-pyrimidin-2-ylamine; (R)-4-Adamantan-1-yl-6-(3-methylamino-pyrrolidin-1-yl)-pyrimidin-2-ylamine; 4-Adamantan-1-yl-6-(4-methyl-piperazin-1-yl)-pyrimidin-2-ylamine; 4-(4-Methyl-tetrahydro-pyran-4-yl)-6-piperazin-1-yl-pyrimidin-2-ylamine; 4-(4-Methyl-piperazin-1-yl)-6-(4-methyl-tetrahydro-pyran-4-yl)-pyrimidin-2-ylamine; (R)-4-(3-Methylamino-pyrrolidin-1-yl)-6-(4-methyl-tetrahydro-pyran-4-yl)-pyrimidin-2-ylamine; 4-(trans-2-Phenyl-cyclopropyl)-6-piperazin-1-yl-pyrimidin-2-ylamine; (R)-4-(3-Amino-pyrrolidin-1-yl)-6-(trans-2-phenyl-cyclopropyl)-pyrimidin-2-ylamine; 4-(4-Methyl-piperazin-1-yl)-6-(trans-2-phenyl-cyclopropyl)-pyrimidin-2-ylamine; N4-(2-Amino-ethyl)-6-(trans-2-phenyl-cyclopropyl)-pyrimidine-2,4-diamine; (R)-4-(3-Methylamino-pyrrolidin-1-yl)-6-(trans-2-phenyl-cyclopropyl)-pyrimid in-2-ylamine; 4-(3-Amino-azetidin-1-yl)-6-indan-2-yl-pyrimidin-2-ylamine; (R)-4-(3-Amino-pyrrolidin-1-yl)-6-indan-2-yl-pyrimidin-2-ylamine; 4-Indan-2-yl-6-(4-methyl-piperazin-1-yl)-pyrimidin-2-ylamine; (R)-4-Indan-2-yl-6-(3-methylamino-pyrrolidin-1-yl)-pyrimidin-2-ylamine; 4-Indan-2-yl-6-piperazin-1-yl-pyrimidin-2-ylamine; 4-(3-Amino-azetidin-1-yl)-6-benzyl-pyrimidin-2-ylannine; (R)-4-(3-Amino-pyrrolidin-1-yl)-6-benzyl-pyrimidin-2-ylamine; N4-(2-Amino-ethyl)-6-indan-2-yl-pyrimidine-2,4-diamine; (R)-4-(2,3-Dihydro-benzofuran-2-yl)-6-(3-methylamino-pyrrolidin-1-yl)- pyrimidin-2-ylamine; 4-(cis-Hexahydro-pyrrolo[3,4-c]pyrrol-2-yl)-6-(4-methyl-tetrahydro-pyran-4-yl)-pyrimidin-2-ylamine; 4-(2,3-Dihydro-benzofuran-2-yl)-6-piperazin-1-yl-pyrimidin-2-ylamine; 4-(3-Amino-azetidin-1-yl)-6-(2,3-dihydro-benzofuran-2-yl)-pyrimidin-2-ylamine; 4-(cis-Hexahydro-pyrrolo[3,4-c]pyrrol-2-yl)-6-indan-2-yl-pyrimidin-2-ylamine; (R)-4-(3-Amino-pyrrolidin-1-yl)-6-(4-methyl-tetrahydro-pyran-4-yl)-pyrimidin-2-ylamine; (R)-4-(3-Amino-pyrrolidin-1-yl)-6-(tetrahydro-pyran-4-yl)-pyrimidin-2-ylamine; N4-(2-Amino-ethyl)-6-(tetrahydro-pyran-4-yl)-pyrimidine-2, 4-diamine; N4-(2-Amino-ethyl)-N4-methyl-6-(tetrahydro-pyran-4-yl)-pyrimidine-2,4-diamine; (R)-4-(3-Amino-pyrrolidin-1-yl)-6-phenethyl-pyrimidin-2-ylamine; 4-(4-Methyl-piperazin-1-yl)-6-phenethyl-pyrimidin-2-ylamine; (R)-4-(3-Methylamino-pyrrolidin-1-yl)-6-phenethyl-pyrimidin-2-ylamine; 4-(4-Methyl-piperazin-1-yl)-6-(3,3,3-trifluoro-propyl)-pyrimidin-2-ylamine; 4-Piperazin-1-yl-6-(3,3,3-trifluoro-propyl)-pyrimidin-2-ylamine; (R)-4-(3-Methylamino-pyrrolidin-1-yl)-6-(3,3,3-trifluoro-propyl)-pyrimidin-2-ylamine; (R)-4-(3-Amino-pyrrolidin-1-yl)-6-(3,3,3-trifluoro-propyl)-pyrimidin-2-ylamine; 4-Cyclopentyl-5-methoxy-6-(4-methyl-piperazin-1-yl)-pyrimidin-2-ylamine; 4-Cyclopentyl-5-methoxy-6-piperazin-1-yl-pyrimidin-2-ylamine; (R)-4-Cyclopentyl-5-methoxy-6-(3-methylamino-pyrrolidin-1-yl)-pyrimidin-2-ylamine; (R,R)-4-Cyclopentyl-5-methoxy-6-(octahydro-pyrrolo[3,4-b]pyridin-6-yl)-pyrimidin-2-ylamine; N4-(2-Amino-ethyl)-N4-methyl-6-(tetrahydro-furan-3-yl)-pyrimidine-2,4-diamine; 4-(cis-Octahydro-pyrrolo[3,4-b]pyridin-6-yl)-6-(tetrahydro-furan-3-yl)-pyrimidin-2-ylamine; (R)-4-(3-Methylamino-pyrrolidin-1-yl)-6-(tetrahydro-furan-3-yl)-pyrimidin-2-ylamine; 4-[1,4]Diazepan-1-yl-6-(tetrahydro-furan-3-yl)-pyrimidin-2-ylamine; (−)-4-Piperazin-1-yl-6-(tetrahydro-furan-3-yl)-pyrimidin-2-ylamine; (+)-4-Piperazin-1-yl-6-(tetrahydro-furan-3-yl)-pyrimidin-2-ylamine; N4-(2-Amino-ethyl)-6-(tetrahydro-furan-3-yl)-pyrimidine-2,4-diamine; N4-(3-Amino-propyl)-6-(tetrahydro-furan-3-yl)-pyrimidine-2,4-diamine; N4-Methyl-N4-(2-methylamino-ethyl)-6-(tetrahydro-furan-3-yl)-pyrimidine-2,4-diamine; N4-(2-Methylamino-ethyl)-6-(tetrahydro-furan-3-yl)-pyrimidine-2,4-diamine; 5-Fluoro-4-methyl-6-(4-methyl-piperazin-1-yl)-pyrimidin-2-ylamine; 5-Fluoro-4-methyl-6-(octahydro-pyrrolo[3,4-b]pyridin-6-yl)-pyrimidin-2-ylamine; 5-Fluoro-4-methyl-6-piperazin-1-yl-pyrimidin-2-ylamine; (R)-5-Fluoro-4-methyl-6-(3-methylarnino-pyrrolidin-1-yl)-pyrimidin-2-ylamine; N4-(2-Amino-ethyl)-5-fluoro-6,N4-dimethyl-pyrimidine-2,4-diamine; 4-Piperazin-1-yl-6-pyridin-4-ylmethyl-pyrimidin-2-ylamine; (R)-4-(3-Methylamino-pyrrolidin-1-yl)-6-pyridin-4-ylmethyl-pyrimidin-2-ylamine; 4-(4-Methyl-piperazin-1-yl)-6-pyridin-4-ylmethyl-pyrimidin-2-ylamine; 4-(4-Methyl-piperazin-1-yl)-6-thiophen-3-ylmethyl-pyrimidin-2-ylamine; (R)-4-(3-Methylamino-pyrrolidin-1-yl)-6-thiophen-3-ylmethyl-pyrimidin-2-ylamine; 4-Piperazin-1-yl-6-thiophen-3-ylmethyl-pyrimidin-2-ylamine; (R)-4-(3-Amino-pyrrolidin-1-yl)-6-thiophen-3-ylmethyl-pyrimidin-2-ylamine; 4-(cis-Octahydro-pyrrolo[3,4-b]pyridin-6-yl)-6-thiophen-3-ylmethyl-pyrimidin-2-ylamine; $N^4$-(2-Amino-ethyl)-6-thiophen-3-ylmethyl-pyrimidine-2,4-diamine; 4-(4-Methyl-piperazin-1-yl)-6-thiophen-2-ylmethyl-pyrimidin-2-ylamine; (R)-4-(3-Methylamino-pyrrolidin-1-yl)-6-thiophen-2-ylmethyl-pyrimidin-2-ylamine; 4-Piperazin-1-yl-6-thiophen-2-ylmethyl-pyrimidin-2-ylamine; (R)-4-(3-Amino-pyrrolidin-1-yl)-6-thiophen-2-ylmethyl-pyrimidin-2-ylamine; 4-(cis-Octahydro-pyrrolo[3,4-b]pyridin-6-yl)-6-thiophen-2-ylmethyl-pyrimidin-2-ylamine; $N^4$-(2-Amino-ethyl)-6-thiophen-2-ylmethyl-pyrimidine-2,4-diamine; $N^4$-(2-Amino-ethyl)-6-methoxymethyl-pyrimidine-2,4-diamine; 4-(3-Amino-azetidin-1-yl)-6-methoxymethyl-pyrimidin-2-ylamine; (R)-4-Methoxymethyl-6-(3-methylamino-pyrrolidin-1-yl)-pyrimidin-2-ylamine; (R)-4-(3-Amino-pyrrolidin-1yl)-6-methoxymethyl-pyrimidin-2-ylamine; 4-Methoxymethyl-6-(4-methyl-piperazin-1-yl)-pyrimidin-2-ylamine; 4-Methoxymethyl-6-piperazin-1-yl-pyrimidin-2-ylamine; (R)-4-(3-Amino-piperidin-1-yl)-6-methoxymethyl-pyrimidin-2-ylamine; (R,R)-4-Methoxymethyl-6-(octahydro-pyrrolo[3,4-b]pyridin-6-yl)-pyrimidin-2-ylamine; 4-(4-Methyl-piperazin-1-yl)-6-(tetrahydro-furan-2-ylmethyl)-pyrimidin-2-ylamine; (R)-4-(3-Methylamino-pyrrolidin-1-yl)-6-(tetrahydro-furan-2-ylmethyl)-pyrimidin-2-ylamine; 4-(cis-5-Methyl-hexahydro-pyrrolo[3,4-c]pyrrol-2-yl)-6-(tetrahydro-furan-2-ylmethyl)-pyrimidin-2-ylamine; 4-Piperazin-1-yl-6-(tetrahydro-furan-2-ylmethyl)-pyrimidin-2-ylamine; 4-(cis-Octahydro-pyrrolo[3,4-b]pyridin-6-yl)-6-(tetrahydro-furan-2-ylmethyl)-pyrimidin-2-ylamine; 4-(4-Chloro-benzyl)-6-(4-methyl-piperazin-1-yl)-pyrimidin-2-ylamine; 4-(4-Chloro-benzyl)-6-piperazin-1-yl-pyrimidin-2-ylamine; (R)-4-(4-Chloro-benzyl)-6-(3-methylamino-pyrrolidin-1-yl)-pyrimidin-2-ylamine; (R)-4-(3-Amino-pyrrolidin-1-yl)-6-(4-chloro-benzyl)-pyrimidin-2-ylamine; 4-(4-Chloro-benzyl)-6-(cis-5-methyl-hexahydro-pyrrolo[3,4-c]pyrrol-2-yl)-pyrimidin-2-ylamine; 4-(4-Chloro-benzyl)-6-(cis-hexahydro-pyrrolo[3,4-c]pyrrol-2-yl)-pyrimidin-2-ylamine; N4-(2-Amino-ethyl)-6-(4-chloro-benzyl)-N4-methyl-pyrimidine-2,4-diamine; 4-Ethyoxymethyl-6-(4-methyl-piperazin-1-yl)-pyrimidin-2-ylamine; 4-Ethoxymethyl-6-piperazin-1-yl-pyrimidin-2-ylamine; (R)-Ethoxymethyl-6-(3-methylamino-pyrrolidin-1-yl)-pyrimidin-2-ylamine; (R)-Ethoxymethyl-6-(3-amino-pyrrolidin-1-yl)-pyrimidin-2-ylamine; Isopropoxymethyl-6-((R)-3-methylamino-pyrrolidin-1-yl)-pyrimidin-2-ylarnine; 4-Isopropoxymethyl-6-piperazin-1-yl-pyrimidin-2-ylamine; (R)-Isopropoxymethyl-6-(3-amino-pyrrolidin-1-yl)-pyrimidin-2-ylamine; 4-Isopropoxymethyl-6-(4-methyl-piperazin-1-yl)-pyrimidin-2-ylamine; 4-Phenethyl-6-piperazin-1-yl-pyrimidin-2-ylamine; 4-(3-Amino-azetidin-1-yl)-6-phenethyl-pyrimidin-2-ylamine; (R)-4-(3-Amino-pyrrolidin-1-yl)-6-(tetrahydro-pyran-4-yl)-pyrimidin-2-ylamine; $N^4$-(2-Amino-ethyl)-6-benzyl-N4-methyl-pyrimidine-2,4-diamine; 4-Indan-2-yl-6-(octahydro-pyrrolo[3,4-b]pyridin-6-yl)-pyrimidin-2-ylamine; 4-(3-Amino-azetidin-1-yl)-7,8-dihydro-5H-pyrano[4,3-d]pyrimidin-2-ylamine; 4-(3-Amino-azetidin-1-yl)-5,6,7,8-tetrahydro-quinazolin-2-ylamine; 4-(cis-5-Methyl-hexahydro-pyrrolo[3,4-c]pyrrol-2-yl)-7,8-dihydro-5H-pyrano[4,3-d]pyrimidin-2-ylamine; (R)-4-(3-Methylamino-pyrrolidin-1-yl)-6-phenyl-cyclopropyl)-pyrimidin-2-ylamine (diastereomer 1); (R)-4-(3-Methylamino-pyrrolidin-1-yl)-6-(2-phenyl-cyclopropyl)-pyrimidin-2-ylamine (diastereomer 2); 4-Cyclopentyl-6-(cis-1,7-diaza-spiro[4.4]non-7-yl)-pyrimidin-2-ylamine (enantiomer 1); 4-Cyclopentyl-6-(cis-1,7-diaza-spiro[4.4]non-7-yl)-pyrimidin-2-ylamine (enantiomer 2); (R)-4-Isopropoxymethyl-6-(3-methyl-amino-pyrrolidin-1-yl)-pyrimidin-2-ylamine; (R)-4-(3-Amino-pyrrolidin-1-yl)-6-isopropoxymethyl-pyrimidin-2-ylamine; 4-Isopropoxymethyl-6-piperazin-1-yl-pyrimidin-2-ylamine; 4-Isopropoxymethyl-6-(4-methyl-piperazin-1-yl)-pyrimidin-2-ylamine; 4-(3-Amino-azetidin-1-yl)-6-isopropoxymethyl-pyrimidin-2-ylamine; 4-Isopropoxymethyl-6-(8-methyl-3,8-diaza-bicyclo[3.2.1]oct-3-yl)-pyrimidin-2-ylamine; (R)-4-Cyclopropoxymethyl-6-(3-methylamino-pyrrolidin-1-yl)-pyrimidin-2-ylamine;

(R)-(4-Amino-pyrrolidin-1-yl)-6-cyclopropoxymethyl-pyrimidin-2-ylamine; 4-Cyclopropoxymethyl-6-piperazin-1-yl-pyrimidin-2-ylamine; 4-Cyclopropoxymethyl-6-(4-methyl-piperazin-1-yl)-pyhmidin-2-ylamine; 4-(3-Amino-azetidin-1-yl)-6-cyclopropoxymethyl-pyrimidin-2-ylamine; 4-Cyclopropoxymethyl-6-(8-methyl-3,8-diaza-bicyclo[3.2.1]oct-3-yl)-pyrimidin-2-ylamine; (R)-4-tert-Butoxymethyl-6-(3-methylamino-pyrrolidin-1-yl)-pyrimidin-2-ylamine; (R)-4-(3-Amino-pyrrolidin-1-yl)-6-tert-butoxymethyl-pyhmidin-2-ylamine; 4-tert-Butoxymethyl-6-piperazin-1-yl-pyrimidin-2-ylamine; 4-tert-Butoxymethyl-6-(4-methyl-piperazin-1-yl)-pyrimidin-2-ylamine; 4-(3-Amino-azetidin-1-yl)-6-tert-butoxymethyl-pyrimidin-2-ylamine; 4-tert-Butoxymethyl-6-(8-methyl-3,8-diaza-bicyclo[3.2.1]oct-3-yl)-pyrimidin-2-ylamine; 4-Ethyl-6-(8-methyl-3,8-diaza-bicyclo[3.2.1]oct-3-yl)-pyrimidin-2-ylamine; 4-(8-Methyl-3,8-diaza-bicyclo[3.2.1]oct-3-yl)-6-propyl-pyrimidin-2-ylamine; 4-Isopropyl-6-(8-methyl-3,8-diaza-bicyclo[3.2.1]oct-3-yl)-pyrimidin-2-ylamine; 4-Cyclopentyl-6-(8-methyl-3,8-diaza-bicyclo[3.2.1]oct-3-yl)-pyrimidin-2-ylamine; and pharmaceutically acceptable salts thereof.

In another embodiment, selective Histamine H4 antagonists are selected from those described in the international Patent Application WO2008/008359: 8-Chloro-4-(4-methyl-piperazin-1-yl)-benzo[4,5]furo[3,2-d]pyrimidin-2-ylamine; 6,8-Dichloro-4-(octahydro-pyrrolo[3,4-b]pyridin-6-yl)-benzo[4,5]furo[3,2-d]pyrimidin-2-ylamine; 8-Chloro-4-(4-isopropyl-[1,4]diazepan-1-yl)-benzo[4,5]furo[3,2-d]pyrimidin-2-ylamine; 4-(3-Amino-pyrrolidin-1-yl)-6,8-dichloro-benzo[4,5]furo[3,2-d]pyrimidin-2-ylamine; (R)-6,8-Dichloro-4-(3-methylamino-pyrrolidin-1-yl)-benzo[4,5]furo[3,2-d]pyrimidin-2-ylamine; (R)-4-(3-Methylamino-pyrrolidin-1-yl)-benzo[4,5]furo[3,2-d]pyrimidin-2-ylamine; 8-Chloro-4-[1,4]diazepan-1-yl-benzo[4,5]furo[3,2-d]pyrimidin-2-ylamine; 8-Chloro-4-(octahydro-pyrido[1,2-a]pyrazin-2-yl)-benzo[4,5]furo[3,2-d]pyrimidin-2-ylamine; 8-Chloro-8-(otahydro-pyrrolo[3,4-b]pyridin-6-yl)-benzo[4,5]furo[3,2-d]pyrimidin-2-ylamine; 8-Chloro-4-(4-methyl-[1,4]diazepan-1-yl)-benzo[4,5]furo[3,2-d]pyrimidin-2-ylamine; (S,S)-8-Chloro-4-(2,5-diaza-bicyclo[2.2.1]hept-2-yl)-benzo[4,5]furo[3,2-d]pyrimidin-2-ylamine; 8-Chloro-4-(3-methylamino-pyrrolidin-1-yl)-benzo[4,5]furo[3,2-d]pyrimidin-2-ylamine; (S)-4-(3-Amino-piperidin-1-yl)-8-chloro-benzo[4,5]furo[3,2-d]pyrimidin-2-ylamine; 8-Chloro-4-piperazin-1-yl-benzo[4,5]furo[3,2-d]pyrimidin-2-ylamine; 8-Chloro-4-(3-dimethylamino-pyrrolidin-1-yl)-benzo[4,5]furo[3,2-d]pyrimidin-2-ylamine; 4-(3-Amino-pyrrolidin-1-yl)-8-chloro-benzo[4,5]furo[3,2-d]pyrimidin-2-ylamine; (S)-8-Chloro-4-(3-methylamino-pyrrolidin-1-yl)-benzo[4,5]furo[3,2-d]pyrimidin-2-ylamine; (R)-8-Chloro-4-(3-methylamino-pyrrolidin-1-yl)-benzo[4,5]furo[3,2-d]pyrimidin-2-ylamine; (R)-8-Bromo-4-(3-methylamino-pyrrolidin-1-yl)-benzo[4,5]furo[3,2-d]pyrimidin-2-ylamine; 8-Bromo-4-(hexahydro-pyrrolo[1,2-a]pyrazin-2-yl)-benzo[4,5]furo[3,2-d]pyrimidin-2-ylamine; 4-(3-Amino-pyrrolidin-1-yl)-benzo[4,5]furo[3,2-d]pyrimidin-2-ylamine; (R)-4-(3-Dimethylamino-pyrrolidin-1-yl)-benzo[4,5]furo[3,2-d]pyrimidin-2-ylamine; 4-Piperazin-1-yl-benzo[4,5]furo[3,2-d]pyrimidin-2-ylamine; (R)-8-Chloro-4-(3-dimethylamino-pyrrolidin-1-yl)-benzo[4,5]furo[3,2-d]pyrimidin-2-ylamine; (R)-4-(3-Amino-pyrrolidin-1-yl)-8-chloro-benzo[4,5]furo[3,2-d]pyrimidin-2-ylamine; (S)-4-(3-Aminomethyl-pyrrolidin-1-yl)-8-chloro-benzo[4,5]furo[3,2-d]pyrimidin-2-ylamine; 8-Chloro-4-(hexahydro-pyrrolo[3,4-c]pyrrol-2-yl)-benzo[4,5]furo[3,2-d]pyrimidin-2-ylamine; (R)-4-(3-Amino-piperidin-1-yl)-8-chloro-benzo[4,5]furo[3,2-d]pyrimidin-2-ylamine; 4-(3-Aminomethyl-pyrrolidin-1-yl)-8-chloro-benzo[4,5]furo[3,2-d]pyrimidin-2-ylamine; (R)-4-(3-Aminomethyl-pyrrolidin-1-yl)-8-chloro-benzo[4,5]furo[3,2-d]pyrimidin-2-ylamine; 6,8-Dichloro-4-piperazin-1-yl-benzo[4,5]furo[3,2-d]pyrimidin-2-ylamine; 6,8-Dichloro-4-[1,4]diazepan-1-yl-benzo[4,5]furo[3,2-d]pyrimidin-2-ylamine; (S,S)-4-(2,5-Diaza-bicyclo[2.2.1]hept-2-yl)-benzo[415]furo[3,2-d]pyrimidin-2-ylamine; 8-Chloro-4-(4-isopropyl-piperazin-1-yl)-benzo[4,5]furo[3,2-d]pyrimidin-2-ylamine; 6,8-Dichloro-4-(3-dimethylamino-pyrrolidin-1-yl)-benzo[4,5]furo[3,2-d]pyrimidin-2-ylamine; 4-(Octahydro-pyrido[1,2-a]pyrazin-2-yl)-benzo[4,5]furo[3,2-d]pyrimidin-2-ylamine; 6,8-Dichloro-4-(octahydro-pyrido[1,2-a]pyrazin-2-yl)-benzo[4,5]furo[3,2-d]pyrimidin-2-ylamine; (S,S)-6,8-Dichloro-4-(2,5-diaza-bicyclo[2.2.1]hept-2-yl)-benzo[4,5]furo[3,2-d]pyrimidin-2-ylamine; (R)-8-Fluoro-4-(3-methylamino-pyrrolidin-1-yl)-benzo[4,5]furo[3,2-d]pyrimidin-2-ylamine; 8-Fluoro-4-(hexahydro-pyrrolo[1,2-a]pyrazin-2-yl)-benzo[4,5]furo[3,2-d]pyrimidin-2-ylamine; 8-Fluoro-$N^4$-methyl-$N^4$-(1-methyl-pyrrolidin-3-yl)-benzo[4,5]furo[3,2-d]pyrimidine-2,4-diamine; (R)-8-(3-Methylamino-pyrrolidin-1-yl)-9-oxa-1,5,7-triaza-fluoren-6-ylamine; 8-(Octahydro-pyrrolo[3,4-b]pyridin-6-yl)-9-oxa-1,5,7-triaza-fluoren-6-ylamine; 4-(4-Methyl-piperazin-1-yl)-benzo[4,5]thieno[3,2-d]pyrimidin-2-ylamine; 8-Bromo-4-(octahydro-pyrrolo[3,4-b]pyridin-6-yl)-benzo[4,5]thieno[3,2-d]pyrimidin-2-ylamine; 7-Bromo-4-(octahydro-pyrrolo[3,4-b]pyridin-6-yl)-benzo[4,5]thieno[3,2-d]pyrimidin-2-ylamine; (S)-8-Bromo-4-(3-methylamino-pyrrolidin-1-yl)-benzo[4,5]thieno[3,2-d]pyrimidin-2-ylamine; (R)-8-Bromo-4-(3-methylamino-pyrrolidin-1-yl)-benzo[4,5]thieno[3,2-d]pyrimidin-2-ylamine; (S,S)-8-Bromo-4-(2,5-diaza-bicyclo[2.2.1]hept-2-yl)-benzo[4,5]thieno[3,2-d]pyrimidin-2-ylamine; 8-Bromo-4-(4-methyl-piperazin-1-yl)-benzo[4,5]thieno[3,2-d]pyrimidin-2-ylamine; (S)-4-(3-Methylamino-pyrrolidin-1-yl)-7-trifluoromethyl-benzo[4,5]thieno[3,2-d]pyrimidin-2-ylamine; (R)-4-(3-Methylamino-pyrrolidin-1-yl)-7-trifluoromethyl-benzo[4,5]thieno[3,2-d]pyrimidin-2-ylamine; (S,S)-4-(2,5-Diaza-bicyclo[2.2.1]hept-2-yl)-7-trifluoromethyl-benzo[4,5]thieno[3,2-d]pyrimidin-2-ylamine; 4-(4-Methyl-piperazin-1-yl)-7-trifluoromethyl-benzo[4,5]thieno[3,2-d]pyrimidin-2-ylamine; 7-Bromo-4-(4-methyl-piperazin-1-yl)-benzo[4,5]thieno[3,2-d]pyrimidin-2-ylamine; (R)-7-Bromo4-(3-methylamino-pyrrolidin-1-yl)-benzo[4,5]thieno[3,2-d]pyrimidin-2-ylamine; (S)-7-Bromo-4-(3-methylamino-pyrrolidin-1-yl)-benzo[4,5]thieno[3,2-d]pyrimidin-2-ylamine; 4-(Octahydro-pyrrolo[3,4-b]pyridin-6-yl)-7-trifluoromethyl-benzo[4,5]thieno[3,2-d]pyrimidin-2-ylamine; 7-Chloro-4-(octahydro-pyrrolo[3,4-b]pyridin-6-yl)-benzo[4,5]thieno[3,2-d]pyrimidin-2-ylamine; (R)-7-Chloro-4-(3-methylamino-pyrrolidin-1-yl)-benzo[4,5]thieno[3,2-d]pyrimidin-2-ylamine; (S)-7-Chloro-4-(3-methylamino-pyrrolidin-1-yl)-benzo[4,5]thieno[3,2-d]pyrimidin-2-ylamine; (S,S)-7-Chloro-4-(2,5-diaza-bicyclo[2.2.1]hept-2-yl)-benzo[415]thieno[3,2-d]pyrimidin-2-ylamine; 7-Chloro-4-(4-methyl-piperazin-1-yl)-benzo[4,5]thieno[3,2-d]pyrimidin-2-ylamine; 8-Chloro-4-(octahydro-pyrrolo[3,4-b]pyridin-6-yl)-benzo[4,5]thieno[3,2-d]pyrimidin-2-ylamine; (S)-8-Chloro-4-(3-methylamino-pyrrolidin-1-yl)-benzo[4,5]thieno[3,2-d]pyrimidin-2-ylamine; (R)-8-Chloro-4-(3-methylamino-pyrrolidin-1-yl)-benzo[4,5]thieno[3,2-d]pyrimidin-2-ylamine; 8-Chloro-4-(4-methyl-piperazin-1-yl)-benzo[4,5]thieno[3,2-d]pyrimidin-2-ylamine; (S,S)-8-Chloro-4-(2,5-diaza-bicyclo[2.2.1]hept-2-yl)-benzo[4,5]thieno[3,2-d]pyrimidin-2-ylamine; 8-Chloro-4-(hexahydro-pyrrolo[1,2-a]pyrazin-2-yl)-benzo[4,5]furo[3,2-d]

pyrimidin-2-ylamine; 8-Fluoro-4-(4-methyl-piperazin-1-yl)-benzo[4,5]thieno[3,2-d]pyrimidin-2-ylamine; 8-Fluoro-4-(hexahydro-pyrrolo[3,4-b]pyrrol-5-yl)-benzo[4,5]furo[3,2-d]pyrimidin-2-ylamine; (S)-8-Chloro-4-(3-ethylamino-piperidin-1-yl)-benzo[4,5]furo[3,2-d]pyrimidin-2-ylamine; (R)-8-Chloro-4-(3-ethylamino-pyrrolidin-1-yl)-benzo[4,5]furo[3,2-d]pyrimidin-2-ylamine; (S)-8-Chloro-4-(3-methylamino-piperidin-1-yl)-benzo[4,5]furo[3,2-d]pyrimidin-2-ylamine; (S)-8-Chloro-4-(3-dimethylamino-piperidin-1-yl)-benzo[4,5]furo[3,2-d]pyrimidin-2-ylamine; (R)-8-Fluoro-4-(3-methylamino-pyrrolidin-1-yl)-benzo[4,5]thieno[3,2-d]pyrimidin-2-ylamine; (S,S)-7-Bromo-4-(2,5-diaza-bicyclop[2.2.1]hept-2-yl)-benzo[4,5]thieno[3,2-d]pyrimidin-2-ylamine; 4-(6-Amino-3-aza-bicyclo[3.1.0]hex-3-yl)-8-chloro-benzo[4,5]furo[3,2-d]pyrimidin-2-ylamine; (R)-4-(2-Aminomethyl-pyrrolidin-1-yl)-8-chloro-benzo[4,5]furo[3,2-d]pyrimidin-2-ylamine; 8-Chloro-4-(hexahydro-pyrrolo[3,4-b]pyrrol-5-yl)-benzo[4,5]furo[3,2-d]pyrimidin-2-ylamine; (R,R)-8-Chloro-4-(2,6-diaza-bicyclo[2.2.1]hept-2-yl)-benzo[4,5]furo[3,2-d]pyrimidin-2-ylamine; (R,R)-8-Chloro-4-(octahydro-pyrrolo[3,4-b]pyridin-6-yl)-benzo[4,5]furo[3,2-d]pyrimidin-2-ylamine; 8-Chloro-4-(octahydro-pyrrolo[3,4-b]pyridin-6-yl)-benzo[4,5]furo[3,2-d]pyrimidin-2-ylamine; (R)-4-(3-Methylamino-pyrrolidin-1-yl)-9-trifluoromethyl-benzo[4,5]furo[3,2-d]pyrimidin-2-ylamine; (S,S)-4-(2,5-Diaza-bicyclo[2.2.1]hept-2-yl)-9-methoxy-benzo[4,5]furo[3,2-d]pyrimidin-2-ylamine; 9-Methoxy-4-piperazin-1-yl-benzo[4,5]furo[3,2-d]pyrimidin-2-ylamine; (S)-4-(3-Amino-piperidin-1-yl)-9-methoxy-benzo[4,5]furo[3,2-d]pyrimidin-2-ylamine; 9-Methoxy-4-(4-methyl-piperazin-1-yl)-benzo[4,5]furo[3,2-d]pyrimidin-2-ylamine; 8-Methoxy-4-(4-methyl-piperazin-1-yl)-benzo[4,5]furo[3,2-d]pyrimidin-2-ylamine; 4-Piperazin-1-yl-9-trifluoromethyl-benzo[4,5]furo[3,2-d]pyrimidin-2-ylamine; 4-(4-Methyl-piperazin-1-yl)-9-trifluoromethyl-benzo[4,5]furo[3,2-d]pyrimidin-2-ylamine; (S)-4-(3-Amino-piperidin-1-yl)-9-trifluoromethyl-benzo[4,5]furo[3,2-d]pyrimidin-2-ylamine; (S)-4-(3-Amino-piperidin-1-yl)-8,9-dichloro-benzo[4,5]furo[3,2-d]pyrimidin-2-ylamine; (S,S)-4-(2,5-Diaza-bicyclo[2.2.1]hept-2-yl)-9-trifluoromethyl-benzo[4,5]furo[3,2-d]pyrimidin-2-ylamine; (cis)-8-Chloro-4-(hexahydro-pyrrolo[3,4-b]pyrrol-1-yl)-benzo[4,5]furo[3,2-d]pyrimidin-2-ylamine; N4-(2-Amino-ethyl)-8-chloro-N4-methyl-benzo[4,5]furo[3,2-d]pyrimidine-2,4-diamine; 8-Chloro-4-(3,8-diaza-bicyclo[3.2.1]oct-3-yl)-benzo[4,5]furo[3,2-d]pyrimidin-2-ylamine; (S,S)-8,9-Dichloro-4-(2,5-diaza-bicyclo[2.2.1]hept-2-yl)-benzo[4,5]furo[3,2-d]pyrimidin-2-ylamine; (R)-8,9-Dichloro-4(3-methylamino-pyrrolidin-1-yl)-benzo[4,5]furo[3,2-d]pyrimidin-2-ylamine; (R)-9-Methoxy-4-(3-methylamino-pyrrolidin-1-yl)-benzo[4,5]furo[3,2-d]pyrimidin-2-ylamine; 8,9-Dichloro-4-(4-methyl-piperazin-1-yl)-benzo[4,5]furo[3,2-d]pyrimidin-2-ylamine; (R)-8-Methoxy-4-(3-methylamino-pyrrolidin-1-yl)-benzo[4,5]furo[3,2-d]pyrimidin-2-ylamine; 4-(3-Aminomethyl-azetidin-1-yl)-8-chloro-benzo[4,5]furo[3,2-d]pyrimidin-2-ylamine; 8,9-Dichloro-4-piperazin-1-yl-benzo[4,5]furo[3,2-d]pyrimidin-2-ylamine; (cis)-8-Methoxy-4-(octahydro-pyrrolo[3,4-b]pyridin-6-yl-benzo[4,5]furo[3,2-d]pyrimidin-2-ylamine; (S,S)-8-Chloro-4-(5-methyl-2,5-diaza-bicyclo[2.2.1]hept-2-yl)-benzo[4,5]furo[3,2-d]pyrimidin-2-ylamine; (S)-4-(3-Amino-piperidin-1-yl)-8-methoxy-benzo[4,5]furo[3,2-d]pyrimidin-2-ylamine; (R)-4-(3-Amino-pyrrolidin-1-yl)-benzo[4,5]furo[3,2-d]pyrimidin-2-ylamine; (R)-3-Chloro-8-(3-methylamino-pyrrolidin-1-yl)-9-oxa-1,5,7-triaza-fluoren-6-ylamine; $N^4$-Azetidin-3-ylmethyl-8-chloro-benzo[4,5]furo[3,2-d]pyrimidine-2,4-diamine; $N^4$-Azetidin-3-yl-8-chloro-benzo[4,5]furo[3,2-d]pyrimidine-2,4-diamine; $N^4$-(2-Amino-ethyl)-8-chloro-benzo[4,5]furo[3,2-d]pyrimidine-2,4-diamine; (S,S)-4-(2,5-Diaza-bicyclo[2.2.1]hept-2-yl)-8-methoxy-benzo[4,5]furo[3,2-d]pyrimidin-2-ylamine; (cis)-4-(Hexahydro-pyrrolo[3,4-b]pyrrol-5-yl)-8-methoxy-benzo[4,5]furo[3,2-d]pyrimidin-2-ylamine; 2-[8-Chloro-4-(4-methyl-piperazin-1-yl)-benzo[4,5]furo[3,2-d]pyrimidin-2-ylamino]-ethanol; 2-[4-(4-Methyl-piperazin-1-yl)-benzo[4,5]furo[3,2-d]pyrimidin-2-ylamino]-ethanol; (cis)-2-[8-Chloro-4-octahydro-pyrrol[3,4-b]pyridin-6-yl)-benzo[4,5]furo[3,2-d]pyrimidin-2-ylamino]-ethanol; 2-[8-Methoxy-4-(4-methyl-piperazin-1-yl)-benzo[4,5]furo[3,2-d]pyrimidin-2-ylamino]-ethanol; [8-Chloro-4-(4-methyl-piperazin-1-yl)-benzo[4,5]furo[3,2-d]pyrimidin-2-yl]-cyclopropyl-amine; [8-Chloro-4-(4-methyl-piperazin-1-yl)-benzo[4,5]furo[3,2-d]pyrimidin-2-yl]-isobutyl-amine; Allyl-[8-chloro-4-(4-methyl-piperazin-1-yl)-benzo[4,5]furo[3,2-d]pyrimidin-2-yl]-amine; $N^1$-[8-Chloro-4-(4-methyl-piperazin-1-yl)-benzo[4,5]furo[3,2-d]pyrimidin-2-yl]-propane-1,3-diamine; [8-Chloro-4-(4-methyl-piperazin-1-yl)-benzo[4,5]furo[3,2-d]pyrimidin-2-yl]-(2-methylsulfanyl-ethyl)-amine; [8-Chloro-4-(4-methyl-piperazin-1-yl)-benzo[4,5]furo[3,2-d]pyrimidin-2-yl]-methyl-amine; (S,S)-2-[8-Chloro-4-(2,5-diaza-bicyclo[2.2.1]hept-2-yl)-benzo[4,5]furo[3,2-d]pyrimidin-2-ylamino]-ethanol; 2-[8-Chloro-4-(3-methylamino-pyrrolidin-1-yl)-benzo[4,5]furo[3,2-d]pyrimidin-2-ylamino]-ethanol; 2-[8-Chloro-4-(4-methyl-[1,4]diazepan-1-yl)-benzo[4,5]furo[3,2-d]pyrimidin-2-ylamino]-ethanol; 8-Chloro-4-(3,5-dimethyl-piperazin-1-yl)-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; (2S,5R)-8-Chloro-4-(2,5-dimethyl-piperazin-1-yl)-benzo[4,5]furo[3,2-d]pyrimidin-2-ylamine; (S)-8-Chloro-4-(2-methyl-piperazin-1-yl)-benzo[4,5]furo[3,2-d3pyrimidin-2-ylamine; (R)-8-Chloro-4-(2-methyl-piperazin-1-yl)-benzo[4,5]furo[3,2-d]pyrimidin-2-ylamine; (S)-8-Chloro-4-(5-methyl-piperazin-1-yl)-benzo[4,5]furo[3,2-d]pyrimidin-2-ylamine; (R)-8-Chloro-4-(5-methyl-piperazin-1-yl)-benzo[4,5]furo[3,2-d]pyrimidin-2-ylamine; 9-Fluoro-4-(4-methyl-piperazin-1-yl)-benzo[4,5]furo[3,2-d]pyrimidin-2-ylamine; (R)-9-Fluoro-4-(3-methylamino-pyrrolidin-1-yl)-benzo[4,5]furo[3,2-d]pyrimidin-2-ylamine; 9-Fluoro-4-piperazin-1-yl-benzo[4,5]furo[3,2-d]pyrimidin-2-ylamine; 4-(3-Amino-azetidin-1-yl)-9-fluoro-benzo[4,5]furo[3,2-d]pyrimidin-2-ylamine; 4-(4-Methyl-piperazin-1-yl)-8-trifluoromethyl-benzo[4,5]furo[3,2-d]pyrimidin-2-ylamine; (R)-4-(3-Methylamino-pyrrolidin-1-yl)-8-trifluoromethyl-benzo[4,5]furo[3,2-d]pyrimidin-2-ylamine; (S)-4-(3-Amino-piperidin-1-yl)-8-trifluoromethyl-benzo[4,5]furo[3,2-d]pyrimidin-2-ylamine; 4-Piperazin-1-yl-8-trifluoromethyl-benzo[4,5]furo[3,2-d]pyrimidin-2-ylamine; (S,S)-4,2,5-Diaza-bicyclo[2.2.1]hept-2-yl)-8-trifluoromethyl-benzo[4,5]furo[3,2-d]pyrimidin-2-ylamine; 4-(3-Amino-azetidin-1-yl)-8-trifluoromethyl-benzo[4,5]furo[3,2-d]pyrimidin-2-ylamine; 8,9-Difluoro-4-(4-methyl-piperazin-1-yl)-benzo[4,5]furo[3,2-d]pyrimidin-2-ylamine; 8,9-Difluoro-4-piperazin-1-yl-benzo[4,5]furo[3,2-d]pyrimidin-2-ylamine; (S)-4-(3-Amino-piperidin-1-yl)-8,9-difluoro-benzo[4,5]furo[3,2-d]pyrimidin-2-ylamine; (R)-8,9-Difluoro-4-(3-methylamino-pyrrolidin-1-yl)-benzo[4,5]furo[3,2-d]pyrimidin-2-ylamine; (S,S)-4-(2,5-Diaza-bicyclo[2.2.1]hept-2-yl)-8,9-difluoro-benzo[4,5]furo[3,2-d]pyrimidin-2-ylamine; 4-(3-Amino-azetidin-1-yl)-8,9-difluoro-benzo[4,5]furo[3,2-d]pyrimidin-2-ylamine; 9-Chloro-4-(4-methyl-piperazin-1-yl)-benzo[4,5]furo[3,2-d]pyrimidin-2-ylamine; (R)-9-Chloro-4-(3-methylamino-pyrrolidin-1-yl)-benzo[4,5]furo[3,2-d]pyrimidin-2-ylamine; 9-Chloro-4-piperazin-1-yl-benzo[4,5]

furo[3,2-d]pyrimidin-2-ylamine; (S)-4-(3-Amino-piperidin-1-yl)-9-chloro-benzo[4,5]furo[3,2-d]pyrimidin-2-ylamine; (S,S)-9-Chloro-4-(2I5-diaza-bicyclo[2.2.1]hept-2-yl)-benzo[4,5]furo[3,2-d]pyrimidin-2-ylamine; 4-(3-Amino-azetidin-1-yl)-9-chloro-benzo[4,5]furo[3,2-d]pyrimidin-2-ylamine; (R)-7-Methoxy-4-(3-methylamino-pyrrolidin-1-yl)-benzo[4,5]furo[3,2-d]pyrimidin-2-ylamine; (S)-7-Methoxy-4-(3-methylamino-pyrrolidin-1-yl)-benzo[4,5]thieno[3,2-d]pyrimidin-2-ylamine; 7-Methoxy--(4-methyl-piperazin-1-yl)-benzo[4,5]thieno[3,2-d]pyrimidin-2-ylamine; (S)-2-[4-(3-Amino-piperidin-1-yl)-8-chloro-benzo[4,5]furo[3,2-d]pyrimidin-2-ylamino]-ethanol; 2-(8-Chloro-4-piperazin-1-yl-benzo[4,5]furo[3,2-d]pyrimidin-2-ylamino)-ethanol; 2-[4-(3-Amino-azetidin-1-yl)-8-chloro-benzo[4,5]furo[3,2-d]pyrimidin-2-ylamino]-ethanol; [8-Chloro-4-(4-methyl-piperazin-1-yl)-benzo[4,5]furo[3,2-d]pyrimidin-2-yl]-dimethyl-amine; and pharmaceutically acceptable salts thereof.

In another embodiment, selective Histamine H4 antagonists are selected from those described in the international Patent Application WO2009077608: 4-Cyclohexyloxymethyl-6-(3-(methylamino)azetidin-1-yl)pyrimidin-2-amine; 4-Cyclohexyloxymethyl-6-((3R)-3-(methylamino)pyrrolidin-1-yl)pyrimidin-2-amine; 4-(Cyclopropylmethoxymethyl)-6-(3-(methylamino)azetidin-1-yl)pyrimidin-2-amine; 4-(Cyclopropylmethoxymethyl)-6-((3R)-3-(methylamino)pyrrolidin-1-yl)pyrimidin-2-amine; 4-Cyclobutoxymethyl-6-(3-(methylamino)azetidin-1-yl)pyrimidin-2-amine; 4-Cyclobutoxymethyl-6-((3R)-3-(methylamino)pyrrolidin-1-yl)pyrimidin-2-amine; 4-Cyclopentoxymethyl-6-(3-(methylamino)azetidin-1-yl)pyrimidin-2-annine; 4-Cyclopentoxymethyl-6-((3R)-3-(methylamino)pyrrolidin-1-yl)pyrimidin-2-amine; 4-Isopropoxymethyl-6-(3-(methylamino)azetidin-1-yl)pyrimidin-2-amine; 4-Isopropoxymethyl-6-((3R)-3-(methylamino)pyrrolidin-1-yl)pyrimidin-2-amine; 4-Isobutoxymethyl-6-(3-(methylannino)azetidin-1-yl)pyrimidin-2-amine; 4-Isobutoxymethyl-6-((3R)-3-(methylamino)pyrrolidin-1-yl)pyrimidin-2-amine; 4-(2,2-Dimethylpropoxymethyl)-6-(3-(methylamino)azetidin-1-yl)pyrimidin-2-amine; 4-(2,2-Dimethylpropoxynnethyl)-6-((3R)-3-(methylannino)pyrrolidin-1-yl)pyrimidin-2-amine; 4-tert-Butoxymethyl-6-((3R)-3-(methylamino)pyrrolidin-1-yl)pyrimidin-2-amine; 4-(Cyclopentylmethoxymethyl)-6-(3-(methylamino)azetidin-1-yl)pyrimidin-2-amine; 4-(Cyclopentylmethoxymethyl)-6-((3R)-3-(methylamino)pyrrolidin-1-yl)pyrimidin-2-amine; 4-(((1S,2R,4R)-Bicyclo[2.2.1]heptan-2-yloxy)methyl)-6-(3-(methylamino)azetidin-1-yl) pyrimidin-2-amine; 4-(((1S,2R,4R)-Bicyclo[2.2.1]heptan-2-yloxy)methyl)-6-((3R)-3-(methylamino)pyrrolidin-1-yl)pyrimidine-2-amine; 4-Benzyloxymethyl-6-(3-(methylamino)azetidin-1-yl)pyrimidin-2-amine; 4-Benzyloxymethyl-6-((3R)-3-(methylamino)pyrrolidin-1-yl)pyrimidin-2-amine; 6-Methoxymethyl-4-((3R)-3-(methylamino)pyrrolidin-1-yl)pyrimidin-2-amine; 6-Methoxymethyl-4-(3-(methylamino)azetidin-1-yl)pyrimidin-2-amine; 4-(3-(Methylamino)azetidin-1-yl)-6-phenoxymethylpyrimidin-2-amine; 6-(2-Methoxyethyl)4-(3-(methylamino)azetidin-1-yl)pyrimidin-2-amine; 4-(4-Fluorophenoxymethyl)-6-(3-(methylamino)azetidin-1-yl)pyrimidin-2-amine; 4-(2,4-Difluorophenoxymethyl)-6-(3-(methylamino)azetidin-1-yl)pyrimidin-2-amine; 4-(3,4-Difluorophenoxymethyl)-6-(3-(methylamino)azetidin-1-yl)pyrimidin-2-amine; 4-(2,4-Difluorophenoxymethyl)-6-((3R)-3-(methylamino)pyrrolidin-1-yl)pyrimidin-2-amine; 4-(3,4-Difluorophenoxymethyl)-6-((3R)-3-(methylamino)pyrrolidin-1-yl)pyrimidin-2-amine; 4-(3-Aminoazetidin-1-yl)-6-isopropoxymethylpyrimidin-2-amine; 4-((3R)-3-Aminopyrrolidin-1-yl)-6-isopropoxynnethylpyrimidin-2-amine; 4-(3-(Methylamino)azetidin-1-yl)-6-(tetrahydropyran-4-yl)pyrimidin-2-amine; 4-(3-(Methylamino)azetidin-1-yl)-6-((S)-tetrahydrofuran-2-yl)pyrimidin-2-amine; 4-((3R)-3-(Methylamino)pyrrolidin-1-yl)-6-((S)-tetrahydrofuran-2-yl)pyrimidin-2-amine; 4-(3-(Methylamino)azetidin-1-yl)-6-((R)-tetrahydrofuran-2-yl)pyrimidin-2-amine; 4-((3R)-3-(Methylamino)pyrrolidin-1-yl)-6-((R)-tetrahydrofuran-2-yl)pyrimidin-2-amine; 4-(2-(4-Chlorophenoxy)propan-2-yl)-6-(3-(methylamino)azetidin-1-yl)pyrimidin-2-amine; 4-(2-(4-Chlorophenoxy)propan-2-yl)-6-((3R)-3-(methylamino)pyrrolidin-1-yl)pyrimidin-2-amine; 6-((R)-1-Methoxyethyl)-4-(3-(methylamino)azetidin-1-yl)pyrimidin-2-amine; 4-(3-(Methylamino)azetidin-1-yl)-6-((R)-phenyl(methoxy)methyl)pyrimidin-2-amine; 4-((3R)-3-(Methylamino)pyrrolidin-1-yl)-6-((R)-phenyl(methoxy)methyl)pyrimidin-2-amine; 4-(3-(Methylamino)azetidin-1-yl)-6-((S)-phenyl(methoxy)methyl)pyrimidin-2-amine; 4-Cyclohexyloxymethyl-6-[3-methyl-3-(methylamino)azetidin-1-yl]pyrimidin-2-amine; 4-Isobutoxymethyl-6-[3-methyl-3-(methylamino)azetidin-1-yl]pyrimidin-2-amine; 4-Isopropoxymethyl-6-[3-methyl-3-(methylamino)azetidin-1-yl]pyrimidin-2-amine; 4-(1,1-Dimethyl-2-methoxyethyl)-6-(3-(methylamino)azetidin-1-yl)pyrimidin-2-amine; 4-(2-Isopropoxyethyl)-6-(3-(methylamino)azetidin-1-yl)pyrimidin-2-amine; 4-(1-(Methoxymethyl)cyclopentyl)-6-((3R)-3-(methylamino)pyrrolidin-1-yl)pyrimidin-2-amine; 4-[3-Methyl-3-(methylamino)azetidin-1-yl]-6-[(2S)-tetrahydrofuran-2-yl]pyrimidin-2-amine; 4-[(Dicyclopropylmethoxy)methyl]-6-(3-(methylamino)azetidin-1-yl)pyrimidin-2-amine; 4-(1-(Methoxymethyl)cyclopentyl)-6-(3-(methylamino)azetidin-1-yl)pyrimidin-2-amine; Methyl 3-(((2-amino-6-(3-(methylamino)azetidin-1-yl)pyrimidin-4-yl)methoxy)nnethyl)benzoate; Methyl-4-(((2-amino-6-(3-(methylamino)azetidin-1-yl)pyrimidin-4-yl)methoxy)methyl)benzoate; Methyl-2-(((2-amino-6-(3-(methylamino)azetidin-1-yl) pyrimidin-4-yl)methoxy)nnethyl)benzoate; 4-(3-(Methylamino)azetidin-1-yl)-6-((4-(methylsulfonyl)benzyloxy)methyl)pyrimidin-2-amine; 4-(3-(Methylamino)azetidin-1-yl)-6-((3-(methylsulfonyl)benzyloxy)methyl)pyrimidin-2-amine; 2-[3-(((2-Amino-6-(3-(methylamino)azetidin-1-yl)pyrimidin-4-yl)methoxy)methyl)phenyl]propan-2-ol; [3-(((2-Amino-6-(3-(methylamino)azetidin-1-yl)pyrimidin-4-yl)methoxy)methyl)phenyl]methanol; [4-(((2-Amino-6-(3-(methylamino)azetidin-1-yl)pyrimidin-4-yl)methoxy)methyl)phenyl]methanol; [2-(((2-Amino-6-(3-(methylamino)azetidin-1-yl)pyrimidin-4-yl)methoxy)methyl)phenyl]methanol; 3-[((2-Amino-6-(3-(methylamino)azetidin-1-yl)pyrimidin-4-yl)methoxy)methyl]benzoic acid; 3-[((2-Amino-6-(3-(methylamino)azetidin-1-yl)pyrimidin-4-yl)methoxy)methyl]benzamide; and 3-R(2-Amino-6-(3-(methylamino)azetidin-1-yl)pyrimidin-4-yl)methoxy)methyl]-N-butylbenzamide, or a salt thereof.

In another embodiment, selective Histamine H4 antagonists are selected from those described in the international Patent Application WO2009/056551: 4-[(3R)-3-(Methylamino)pyrrolidin-1-yl]-6,7,8,9-tetrahydrobenzofuro[3,2-d]pyrimidin-2-amine; 4-[3-(Methylamino)azetidin-1-yl]-6,7,8,9-tetrahydrobenzofuro[3,2-d]pyrimidin-2-amine; 4-[(3R)-3-Aminopyrrolidin-1-yl]-6,7,8,9-tetrahydrobenzofuro[3,2-d]pyrimidin-2-amine; 4-(3-Aminoazetidin-1-yl)-6,7,8,9-tetrahydrobenzofuro[3,2-d]pyrimidin-2-amine; 4-[(4aR,7aR)-Octahydro-6H-pyrrolo[3,4-b]pyrimidin-6-yl]-6,7,8,9-tetrahydrobenzofuro[3,2-d]pyrimidin-2-amine; 4-[3-Methyl-3-(Methylamino)azetidin-1-yl]-6,7,8,9-tetrahydrobenzofuro[3,2-d]pyrimidin-2-amine; 4-Piperazin- 1-yl-6,7,8,9-tetrahydrobenzofuro[3,2-d]pyrimidin-2-amine; 4-(1,4-Diazepan-1-yl)-6,7,8,9-tetrahydrobenzofuro[3,2-d]pyrimidin-2-amine; 4-[(3R)-3-(Methylamino)pyrrolidin-1-yl]-6,7,8,9-tetrahydrobenzofuro[3,2-d]pyrimidine; 4-[3-(Methylamino)azetidin-1-yl]-6,7,8,9-tetrahydrobenzofuro[3,2-d]pyrimidine; 4-(1,4-Diazepan-1-yl)-6,7,8,9-tetrahydrobenzofuro[3,2-d]pyrinnidine; 4-[(3R)-3-(Methylamino)pyrrolidin-1-yl]-7,8,9,10-tetrahydro-6H-cyclohepta[4,5]furo[3,2-d]pyrimidin-2-amine; 4-[3-(Methylamino)azetidin-1-yl]-7,8,9,10-tetrahydro-6H-cyclohepta[4,5]furo[3,2-d]pyrimidin-2-amine; 4-[(3R)-3-Aminopyrrolidin-1-yl]-7,8,9,10-tetrahydro-6H-cyclohepta[4,5]furo[3,2-d]pyrimidin-2-amine; 4-[3-Methyl-3-(methylamino)azetidin-1-yl]-7,8,9,10-tetrahydro-6H-cyclohepta[4,5]furo[3,2-d]pyrimidin-2-amine; 4-[3-(Methylamino)azetidin-1-yl]-7,8-dihydro-6H-cyclopenta[4,5]furo[3,2-d]pyrimidin-2-amine; 4-[(3R)-3-(Methylamino)pyrrolidin-1-yl]-7,8-dihydro-6H-cyclopenta[4,5]furo[3,2-d]pyrimidin-2-amine; $N^4$-[(3R)-1-(Methylpyrrolidin-3-yl]amino-6,7,8,9-tetrahydrobenzofuro[3,2-d]pyrimidine-2,4-diamine; 4-(4-Methylpiperazin-1-yl)-6,7,8,9-tetrahydrobenzofuro[3,2-d]pyrimidin-2-amine; (S)-4-(3-Methylpiperazin-1-yl)-6,7,8,9-tetrahydrobenzofuro[3,2-d]pyrimidin-2-amine; and 4-(4-Methylpiperazin-1-yl)-6,7,8,9-tetrahydrobenzofuro[3,2-d]pyrimidin and salts thereof.

In another embodiment, selective Histamine H4 antagonists are selected from those described in the international Patent Application WO2009/068512: 4-(Cyclopropylmethyl)-6-((3R)-3-(methylamino)pyrrolidin-1-yl)pyrimidin-2-amine; 4-Cyclopropylmethyl-6-(3-(methylamino)azetidin-1-yl)pyrimidin-2-amine; 4-Cyclopropylmethyl-6-((3R)-3-aminopyrrolidin-1-yl)pyrimidin-2-amine; 4-Cyclopropylmethyl-6-(piperazin-1-yl)pyrimidin-2-amine; 4-Cyclopropylmethyl-6-(3-methyl-3-(methylamino)azetidin-1-yl)pyrimidin-2-amine; 4-(3-Aminoazetidin-1-yl)-6-cyclopropylmethyl-pyrimidin-2-amine; 4-Cyclopropylmethyl-6-(1,4-diazepan-1-yl) pyrimidin-2-amine; 4-(4-Aminopiperidin-1-yl)-6-cyclopropylmethyl-pyrimidin-2-amine; 4-Cyclopropylmethyl-6-((4aR,7aR)-octahydropyrrolo[3,4-b]pyridine-6-yl)pyrimidin-2-amine; 4-Cyclopropylmethyl-6-((3S)-3-(methylamino)pyrrolidin-1-yl)pyrimidin-2-amine; (R)-4-Cyclopropylmethyl-6-[(N-methylpyrrolidin-3-yl)amine]pyrimidin-2-amine; (S)-4-Cyclopropylmethyl-6-(3-methylpiperazin-1-yl)pyrimidin-2-amine; (R)-4-Cyclopropylmethyl-6-(3-methylpiperazin-1-yl)pyrimidin -2-amine; 4-Cyclopropylmethyl-6-[3-(pyrrolidin-1-yl)azetidin-1-yl]pyrimidin-2-amine; 4-(Cyclopropylmethyl)-6-(hexahydropyrrolo[1,2-a]pyrazin-2(1H)-yl)pyrimidin-2-amine; (S)-4-(Cyclopropylmethyl)-6-(hexahydropyrrolo[1,2-a)]-2(1H)-yl)pyrimidin-2-amine; 4-Isopropyl-6-(3-(methylamino)azetidin-1-yl)pyrimidin-2-amine; 4-Isopropyl-6-((3R)-3-(methylamino)pyrrolidin-1-yl)pyrimidin-2-amine; 4-tert-Butyl-6-(3-(methylamino)azetidin-1-yl)pyrimidin-2-amine; 4-tert-Butyl-6-((3R)-3-(methylamino)pyrrolidin-1-yl)pyrimidin-2-amine; 4-(3-(Methylamino)azetidin-1-yl)-6-propylpyrimidin-2-amine; 4-((3R)-3-(Methylamino)pyrrolidin-1-yl)-6-propylpyrimidin-2-amine; 4-Cyclopropyl-6-(3-(methylamino)azetidin-1-yl)pyrimidin-2-amine; 4-Cyclopropyl-6-((3R)-3-(methylamino)pyrrolidin-1-yl)pyrimidin-2-amine; 4-Ethyl-6-(3-(methylamino)azetidin-1-yl)pyrimidin-2-amine; 4-Ethyl-6-((3R)-3-(methylamino)pyrrolidin-1-yl)pyrimidin-2-amine; 4-Butyl-6-(3-(methylamino)azetidin-1-yl)pyrimidin-2-amine; 4-Butyl-6-((3R)-3-(methylamino)pyrrolidin-1-yl)pyrimidin-2-amine; 4-Cyclopentylmethyl-6-(3-(methylamino)azetidin-1-yl)pyrimidin-2-amine; 4-Cyclopentylmethyl-6-((3R)-3-(methylamino)pyrrolidin-1-yl)pyrimidin-2-amine; 4-Isobutyl-6-((3R)-3-(methylamino)pyrrolidin-1-yl)pyrimidin-2-amine; 4-Isobutyl-6-(3-(methylamino)azetidin-1-yl)pyrimidin-2-amine; 4-(2,2-Dimethylpropyl)-6-((3R)-3-(methylamino)pyrrolidin-1-yl) pyrimidin-2-amine; 4-(2,2-Dimethylpropyl)-6-(3-(methylamino)azetidin-1-yl)pyrimidin-2-amine; trans-4-(2-Phenylcyclopropyl)-6-((3R)-3-(methylamino)pyrrolidin-1-yl)pyrimidin-2-amine; (R)-4-tert-Butyl-6-[(N-methylpyrrolidin-3-yl)amine]pyrimidin-2-amine; 4-(2-Cyclopentylethyl)-6-((3R)-3-(methylamino)pyrrolidin-1-yl)pyrimidin-2-amine; 4-(2-Cyclopentylethyl)-6-(3-(methylamino)azetidin-1-yl) pyrimidin-2-annine; 4-(2-Cyclopropylethyl)-6-((3R)-3-(methylamino)pyrrolidin-1-yl)pyrimidin-2-amine; 4-((3R)-3-(Methylamino)pyrrolidin-1-yl)-6-(4-methylpentyl) pyrimidin-2-amine; 4-(3-(Methylamino)azetidin-1-yl)-6-(4-methylpentyl)pyrimidin-2-amine; 4-(3-Cyclopentylpropyl)-6-((3R)-3-(methylamino)pyrrolidin-1-yl)pyrimidin-2-amine; 4-(4-Cyclohexylbutyl)-6-((3R)-3-(methylamino)pyrrolidin-1-yl)pyrimidin-2-amine; 4-(4-Cyclohexylbutyl)-6-(3-(methylamino)azetidin-1-yl)pyrimidin-2-amine; (S)-4-(2-Cyclopropylethyl)-6-(3-methylpiperazin-1-yl)pyrimidin-2-amine; 4-(3-Aminoazetidin-1-yl)-6-(cyclopentylmethyl) pyrimidin-2-amine; 4-(3-(Methylamino)azetidin-1-yl)-6-(2,2,3,3-tetramethylcyclopropyl)pyrimidin-2-amine; 4-Cyclobutyl-6-(3-(methylamino)azetidin-1-yl)pyrimidin-2-amine; 4-Cyclopentyl-6-(3-(methylamino)azetidin-1-yl) pyrimidin-2-amine; 4-((3R)-3-(Methylamino)pyrrolidin-1-yl)-6-(2,2,3,3-tetramethylcyclopropyl)pyrimidin-2-amine; 4-Isobutyl-6-(3-methyl-3-(methylamino)azetidin-1-yl)pyrimidin-2-amine; 4-(3-Methyl-3-(methylamino)azetidin-1-yl)-6-neopentylpyrimidin-2-amine; (S)-4-(3-Methylpiperazin-1-yl)-6-neopentylpyrimidin-2-amine; 4-(3-(Methylamino)azetidin-1-yl)-6-(1-methylcyclopropyl) pyrimidin-2-amine; (R)-4-(Cyclopropylmethyl)-6-(hexahydropyrrolo[1,2-a]pyrazin-2(1H)-yl)pyrimidin-2-amine; 4-Cyclopentyl-6-(3-methyl-3-(methylamino) azetidin-1-yl)pyrimidin-2-amine; 4-Cyclobutyl-6-(3-methyl-3-(methylamino)azetidin-1-yl)pyrimidin-2-amine; 4-(3-Methyl-3-(methylamino)azetidin-1-yl)-6-(2,2,3,3-tetramethylcyclopropyl)pyrimidin-2-amine; (S)-4-(3-Methylpiperazin-1-yl)-6-(2,2,3,3-tetramethylcyclopropyl)pyrimidin-2-amine; 4-(3-(Methylamino)azetidin-1-yl)-6-(pentan-3-yl)pyrimidin-2-amine; 4-((3R)-3-(Methylamino)pyrrolidin-1-yl)-6-(pentan-3-yl) pyrimidin-2-amine; 4-((1S,2S,4S)-Bicyclo[2.2.1]heptan-2-yl)-6-(3-(methylamino) azetidin-1-yl)pyrimidin-2-amine; and 4-((1S,2R,4S)-Bicyclo[2.2.1]heptan-2-yl)-6-(3-(methylamino)azetidin-1-yl)pyrimidin-2-amine and salts thereof.

In another embodiment, selective Histamine H4 antagonists are selected from those described in the international Patent Application WO2009/080721: 2-Isobutyl-6-((3R)-3-(methylamino)pyrrolidin-1-yl)pyrimidin-4-amine; 2-Cyclohexylmethyl-6-((3R)-3-(methylamino)pyrrolidin-1-yl)pyrimidin-4-amine; 2-(4-Fluorobenzyl)-6-(3-(methylamino) azetidin-1-yl)pyrimidin-4-amine; 2-Isobutyl-6-(3-(methylamino)azetidin-1-yl)pyrimidin-4-amine; 2-Cyclopropyl-6-(3-(methylamino)azetidin-1-yl)pyrimidin-4-amine; 2-tert-Butyl-6-(3-(methylamino)azetidin-1-yl)pyrimidin-4-amine; 2-Isopropyl-6-(3-(methylamino)azetidin-1-yl)pyrimidin-4-amine; 2-(Cyclopropylmethyl)-6-(3-(methylamino)azetidin-1-yl)pyrimidin-4-amine; 6-(3-(Methylamino)azetidin-1-yl)-2-(phenoxymethyl)pyrimidin-4-amine; 2-Cyclopropyl-6-((3R)-3-(methylamino) pyrrolidin-1-yl)pyrimidin-4-amine; 2-tert-Butyl-6-((3R)-3-(methylamino)pyrrolidin-1-yl)pyrimidin-4-amine; 2-Isopropyl-6-((3R)-3-(methylamino)pyrrolidin-1-yl)pyrimidin-4-amine; 6-((3R)-3-(Methylamino)pyrrolidin-1-yl)-

2-(phenoxymethyl)pyrimidin-4-amine; 6-(3-Aminoazetidin-1-yl)-2-isobutylpyrimidin-4-amine; 2-Isobutyl-6-(3-methyl-3-(methylamino)azetidin-1-yl) pyrimidin-4-amine; 6-((3R)-3-aminopyrrolidin-1-yl)-2-isobutylpyrimidin-4-amine; 2-Cyclobutyl-6-(3-(methylamino)azetidin-1-yl)pyrimidin-4-amine; 2-Cyclobutyl-6-((3R)-3-(methylamino)pyrrolidin-1-yl)pyrimidin-4-amine; 2-Cyclopentyl-6-(3-(methylamino)azetidin-1-yl)pyrimidin-4-amine; 2-Cyclopentyl-6-((3R)-3-(methylamino)pyrrolidin-1-yl)pyrimidin-4-amine; 2-(2,2-Dimethylpropyl)-6-(3-(methylamino)azetidin-1-yl)pyrimidin-4-amine; 2-(2,2-Dimethylpropyl)-6-((3R)-3-(methylamino)pyrrolidin-1-yl)pyrimidin-4-amine; 2-(2-Cyclopentylethyl)-6-((3R)-3-(methylamino)pyrrolidin-1-yl)pyrimidin-4-amine; 2-Cyclohexylmethyl-6-(3-(methylamino)azetidin-1-yl)pyrimidin-4-amine; 2-Cyclopropylmethyl-6-((3R)-3-(methylamino)pyrrolidin-1-yl)pyrimidin-4-amine; 2-Cyclohexyl-6-(3-(methylamino)azetidin-1-yl)pyrimidin-4-amine; 2-Cyclohexyl-6-((3R)-3-(methylannino)pyrrolidin-1-yl)pyrimidin-4-amine; and 2-(4-Fluorobenzyl)-6-((3R)-3-(methylamino)pyrrolidin-1-yl)pyrimidin-4-amine, or a salt thereof.

In another embodiment, selective Histamine H4 antagonists are selected from those described in the international Patent Application WO2009/115496: 7-Cyclopropyl-4-(4-methylpiperazin-1-yl)furo[3,2-d]pyrimidin-2-amine; 7-Cyclopropyl-4-[(3S)-(3-methylpiperazin-1-yl)furo[3,2-d]pyrimidin-2-amine; 7-Ethyl-4-[4-methylpiperazin-1-yl)furo[3,2-d]pyrimidin-2-amine; 4-[4-methylpiperazin-1-yl)-7-propylfuro[3,2-d]pyrimidin-2-amine; 7-Cyclopropyl-4-(3-(methylamino)azetidin-1-yl)furo[3,2-d]pyrimidin-2-amine; 7-Cyclopropyl-4-[(3R)-3-(methylamino)pyrrolidin-1-yl)furo[3,2-d]pyrimidin-2-amine; 4-[(3R)-3-Aminopyrrolidin-1-yl)-7-cyclopropylfuro[3,2-d]pyrimidin-2-amine; 4-(3-Aminoazetidin-1-yl)-7-cyclopropylfuro[3,2-d]pyrimidin-2-amine; 7-Cyclopropyl-4-(3-methyl-3-(methylamino)azetidin-1-yl)furo[3,2-d]pyrimidin-2-amine; 7-Cyclopropyl-4-(piperazin-1-yl)furo[3,2-d]pyrimidin-2-amine; 7-Cyclopropyl-4-(1,4-diazepan-1-yl)furo[3,2-d]pyrimidin-2-amine; 7-Ethyl-4-(3-(methylamino)azetidin-1-yl)furo[3,2-d]pyrimidin-2-amine; 7-Ethyl-4-[(3R)-3-(methylamino)pyrrolidin-1-yl)furo[3,2-d]pyrimidin-2-amine; 4-[(3R)-3-Aminopyrrolidin-1-yl]-7-ethylfuro[3,2-d]pyrimidin-2-amine; 7-Ethyl-4-(3-methyl-3-(methylamino)azetidin-1-yl)furo[3,2-d]pyrimidin-2-amine; 7-Ethyl-4-(piperazin-1-yl)furo[3,2-d]pyrimidin-2-amine; 4-(3-(Methylamino)azetidin-1-yl)-7-propylfuro[3,2-d]pyrimidin-2-amine; 4-[(3R)-3-(Methylamino)pyrrolidin-1-yl]-7-propylfuro[3,2-d]pyrimidin-2-amine; 4-[(3R)-3-(Aminopyrrolidin-1-yl)-7-propylfuro[3,2-d]pyrimidin-2-amine; 4-(3-Methyl-3-(methylamino)azetidin-1-yl]-7-propylfuro[3,2-d]pyrimidin-2-amine; 4-(Piperazin-1-yl]-7-propylfuro[3,2-d]pyrimidin-2-amine; 7-Isopropyl-4-(3-(methylamino)azetidin-1-yl]furo[3,2-d]pyrimidin-2-amine; 7-Isopropyl-4-[(3R)-3-(methylamino)pyrrolidin-1-yl]furo[3,2-d]pyrimidin-2-amine; 7-Benzyl-4-(3-(methylamino)azetidin-1-yl]furo[3,2-d]pyrimidin-2-amine; 7-Benzyl-4-[(3R)-3-(methylamino)pyrrolidin-1-yl]furo[3,2-d]pyrimidin-2-amine; 7-Cyclobutyl-4-(3-(methylamino)azetidin-1-yl)furo[3,2d]pyrimidin-2-amine; 7-Cyclobutyl-4-[(3R)-3-methylamino)pyrrolidin-1-yl)furo[3,2d]pyrimidin-2-amine; 7-Cyclopentyl-4-(3-(methylamino)azetidin-1-yl)furo[3,2d]pyrimidin-2-amine; 7-Cyclopentyl-4-[(3R)-3-methylamino)pyrrolidin-1-yl)furo[3,2d]pyrimidin-2-amine; 7-Isobutyl -4-(3-(methylamino)azetidin-1-yl)furo[3,2d]pyrimidin-2-amine; 7-Isobutyl-4-[(3R)-3-methylamino)pyrrolidin-1-yl)furo[3,2d]pyrimidin-2-amine; 4-(3-(Methylamino)azetidin-1-yl)-7-phenylfuro[3,2d]pyrimidin-2-amine; 4-[(3R)-3-(Methylamino)pyrrolidin-1-yl]-7-phenylfuro[3,2d]pyrimidin-2-amine; 7-tert-butyl-4-(3-(methylamino)azetidin-1-yl)furo[3,2d]pyrimidin-2-amine; 7-tert-butyl-4-[(3R)-3-(methylamino)pyrrolidin-1-yl)furo[3,2d]pyrimidin-2-amine; 7-Cyclopropyl-4-(3-(methylamino)azetidin-1-yl)furo[3,2d]pyrimidin-2-amine; 6-Chloro-7-cyclobutyl-4-(3-(methylamino)azetidin-1-yl)furo[3,2-d]pyrimidin-2-amine; 6-Chloro-7-cyclopropyl-4-(3-(methylamino)azetidin-1-yl)furo[3,2-d]pyrimidin-2-amine; 6-Chloro-7-cyclopropyl-4-[(3R)-3-(methylamino)pyrrolidin-1-yl]furo[3,2-d]pyrimidin-2-amine; 6-Chloro-7-isopropyl-4-(3-(methylamino)azetidin-1-yl)furo[3,2-d]pyrimidin-2-amine; 6-Chloro-7-isopropyl-4-[(3R)-3-(methylamino)pyrrolidin-1-yl]furo[3,2-d]pyrimidin-2-amine; 6-Chloro-7-cyclopentyl-4-[(3R)-3-(methylamino)pyrrolidin-1-yl]furo[3,2-d]pyrimidin-2-amine; 4-(3-(Methylamino)azetidin-1-yl)-7-(tetrahydro-2H-pyran-4-yl)furo[3,2-d]pyrimidin-2-amine; 2-Amino-7-isopropyl-4-((3R)-3-(methylamino)pyrrolidin-1-yl)furo[3,2-d]pyrimidine-6-carbonitrile; 2-Amino-7-cyclopropyl-4-(3-(methylamino)azetidin-1-yl) furo[3,2-d]pyrimidine-6-carbonitrile; 7-(1-(Methoxymethyl)cyclopropyl)-4-(3-(methylamino)azetidin-1-yl)furo[3,2-d]pyrimidin-2-amine and salts thereof.

In another embodiment, selective Histamine H4 antagonists are selected from those described in the international Patent Application WO2007/090852: [(R)-1-(2-Amino-8-chlorobenzo[4,5]furo[3,2-d]-pyrimidin-4-yl)pyrrolidin-3-yl]N-methylamine; [(S)-1-(2-Amino-8-chlorobenzo[4,5]furo[3,2-d]-pyrimidin-4-yl)pyrrolidin-3-yl]N-methylamine; [1-(2-Ethylamino-8-chlorobenzo[4,5]furo[3,2-d]-pyrimidin-4-yl)azetidin-3-yl]N-ethylamine; 4-((R)-3-Methylamino-pyrrolidin-1-yl)-benzo[4,5]furo[3,2-d]pyrimidin-2-ylamine; 8-Methyl-4-((R)-3-methylamino-pyrrolidin-1-yl)-benzo[4,5]furo[3,2-d]pyrimidin-2-ylamine; 8-Fluoro-4-((R)-3-methylamino-pyrrolidin-1-yl)-benzo[4,5]furo[3,2-d]pyrimidin-2-ylamine; 8-Bromo-4-((R)-3-methylamino-pyrrolidin-1-yl)-benzo[4,5]furo[3,2-d]pyrimidin-2-ylamine; 7-Chloro-4-((R)-3-methylamino-pyrrolidin-1-yl)-benzo[4,5]furo[3,2-d]pyrimidin-2-ylamine; N-[1-(2-Amino-8-chlorobenzo[4,5]furo[3,2-d]pyrimidin-4-yl)azetidin-3-yl]N-methylamine; 4-(3-Methylamino-azetidin-1-yl)-benzo[4,5]furo[3,2-d]pyrimidin-2-ylamine; 8-Bromo-4-(3-methylamino-azetidin-1-yl)-benzo[4,5]furo[3,2-d]pyrimidin-2-ylamine; 8-Methyl-4-(3-methylamino-azetidin-1-yl)-benzo[4,5]furo[3,2-d]pyrimidin-2-ylamine; 8-Fluoro-4-(3-methylamino-azetidin-1-yl)-benzo[4,5]furo[3,2-d]pyrimidin-2-ylamine; 8-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-8-trifluoromethoxy-benzo[4,5]furo[3,2-d]pyrimidin-2-ylamine; 9-Fluoro-4-((R)-3-methylamino-pyrrolidin-1-yl)-benzo[4,5]furo[3,2-d]pyrimidin-2-ylamine; 9-Methyl-4-((R)-3-methylamino-pyrrolidin-1-yl)-benzo[4,5]furo[3,2-d]pyrimidin-2-ylamine; 9-Methoxy-4-((R)-3-methylamino-pyrrolidin-1-yl)-benzo[4,5]furo[3,2-d]pyrimidin-2-ylamine; 7-Methyl-4-((R)-3-methylamino-pyrrolidin-1-yl)-benzo[4,5]furo[3,2-d]pyrimidin-2-ylamine; 7-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-7-trifluoromethyl-benzo[4,5]furo[3,2-d]pyrimidin-2-ylamine; 6-Chloro-4-((R)-3-methylamino-pyrrolidin-1-yl)-benzo[4,5]furo[3,2-d]pyrimidin-2-ylamine; 6-Methyl-4-((R)-3-methylamino-pyrrolidin-1-yl)-benzo[4,5]furo[3,2-d]pyrimidin-2-ylamine; 6-Methoxy-4-((R)-3-methylamino-pyrrolidin-1-yl)-benzo[4,5]furo[3,2-d]pyrimidin-2-ylamine; 8-Methoxy-4-(3-methylamino-azetidin-1-yl)-benzo[4,5]furo[3,2-d]pyrimidin-2-ylamine; 4-(3-Methylamino-azetidin-1-yl)-8- trifluoromethoxy-benzo[4,5]furo[3,2-d]pyrimidin-2-ylamine; 9-Fluoro-4-(3-methylamino-azetidin-1-yl)-benzo[4,5]furo[3,2-d]pyrimidin-2-ylamine; 9-Methyl-4-(3-methylamino-azetidin-1-yl)-benzo[4,5]furo[3,2-d]pyrimidin-2-ylamine; 9-Methoxy-4-(3-methylamino-azetidin-1-yl)-benzo[4,5]furo[3,2-d]pyrimidin-2-ylamine; 7-Methyl-4-(3-methylamino-azetidin-1-yl)-benzo[4,5]furo[3,2-d]pyrimidin-2-ylamine; 7-Methoxy-4-(3-methylamino-azetidin-1-yl)-benzo[4,5]furo[3,2-d]pyrimidin-2-ylamine; 4-(3-Methylamino-azetidin-1-yl)-7-trifluoromethyl-benzo[4,5]furo[3,2-d]pyrimidin-2-ylamine; 6-Chloro-4-(3-methylamino-azetidin-1-yl)-benzo[4,5]furo[3,2-d]pyrimidin-2-ylamine; 6-Methyl-4-(3-methylamino-azetidin-1-yl)-benzo[4,5]furo[3,2-d]pyrimidin-2-ylamine; 6-Methoxy-4-(3-methylamino-azetidin-1-yl)-benzo[4,5]furo[3,2-d]pyrimidin-2-ylamine; 8-Chloro-4-[3-(cyclopropylmethyl-amino)-pyrrolidin-1-yl]-benzo[4,5]furo[3,2-d]pyrimidin-2-ylamine; 8-Chloro-4-((R)-3-dimethylamino-pyrrolidin-1-yl)-benzo[4,5]furo[3,2-d]pyrimidin-2-ylamine; 4-((R)-3-Amino-pyrrolidin-1-yl)-8-chloro-benzo[4,5]furo[3,2-d]pyrimidin-2-ylamine; 8-Chloro-4-(4-methylamino-piperidin-1-yl)-benzo[4,5]furo[3,2-d]pyrimidin-2-ylamine; 4-(4-Amino-piperidin-1-yl)-8-chloro-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; [8-Chloro-4-((R)-3-methylamino-pyrrolidin-1-yl)-benzo[4,5]furo[3,2-d]pyrimidin-2-yl]-methyl-amine; [8-Chloro-4-((R)-3-methylamino-pyrrolidin-1-yl)-benzo[4,5]furo[3,2-d]pyrimidin-2-yl]-dimethyl-amine; N-[8-Chloro-4-((R)-3-methylamino-pyrrolidin-1-yl)-benzo[4,5]furo[3,2-d]pyrimidin-2-yl]-acetamide; N-[8-Chloro-4-((R)-3-methylamino-pyrrolidin-1-yl)-benzo[4,5]furo[3,2-d]pyrimidin-2-yl]-methanesulfonamide; [8-Chloro-4-((R)-3-methylamino-pyrrolidin-1-yl)-benzo[4,5]furo[3,2-d]pyrimidin-2-yl]-cyclopropyl-amine; [8-Chloro-4-(3-methylamino-azetidin-1-yl)-benzo[4,5]furo[3,2-d]pyrimidin-2-yl]-methyl-amine; [8-Chloro-4-(3-methylamino-azetidin-1-yl)benzo[4,5]furo[3,2-d]pyrimidin-2-yl]-dimethyl-amine; N-[8-Chloro-4-(3-methylamino-azetidin-1-yl)benzo[4,5]furo[3,2-d]pyrimidin-2-yl]-acetamide; N-[8-Chloro-4-(3-methylamino-azetidin-1-yl)benzo[4,5]furo[3,2-d]pyrimidin-2-yl]-methanesulfonamide; [8-Chloro-4-(3-methylamino-azetidin-1-yl)benzo[4,5]furo[3,2-d]pyrimidin-2-yl]-cyclopropyl-amine and salts thereof.

In another embodiment, selective Histamine H4 antagonists are selected from those described in the international Patent Application WO2007/090853: [(R)-1-(2-Amino-8-chlorobenzo[4,5]furo[3,2-d]-pyrimidin-4-yl)pyrrolidin-3-yl]N-methyl amine; 4-((R)-3-Methylamino-pyrrolidin-1-yl)-benzo[4,5]furo[3,2-d]pyrimidin-2-ylamine; 8-Methyl-4-((R)-3-methylamino-pyrrolidin-1-yl)-benzo[4,5]furo[3,2-d]pyrimidin-2-ylamine; 8-Fluoro-4-((R)-3-methylamino-pyrrolidin-1-yl)-benzo[4,5]furo[3,2-d]pyrimidin-2-ylamine; 8-Bromo-4-((R)-3-methylamino-pyrrolidin-1-yl)-benzo[4,5]furo[3,2-d]pyrimidin-2-ylamine; 7-Chloro-4-((R)-3-methylamino-pyrrolidin-1-yl)-benzo[4,5]furo[3,2-d]pyrimidin-2-ylamine; 8-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-8-trifluoromethoxy-benzo[4,5]furo[3,2-d]pyrimidin-2-ylamine; 9-Fluoro-4-((R)-3-methylamino-pyrrolidin-1I-yl)-benzo[4,5]furo[3,2-d]pyrimidin-2-ylamine; 9-Methyl-4-((R)-3-methylamino-pyrrolidin-1-yl)-benzo[4,5]furo[3,2-d]pyrimidin-2-ylamine; 9-Methoxy-4-((R)-3-methylamino-pyrrolidin-1-yl)-benzo[4,5]furo[3,2-d]pyrimidin-2-ylamine; 7-Methyl-4-((R)-3-methylamino-pyrrolidin-1-yl)-benzo[4,5]furo[3,2-d]pyrimidin-2-ylamine; 7-Methoxy-4-((R)-3-methylamino-pyrrolidin-1-yl)-benzo[4,5]furo[3,2-d]pyrimidin-2-ylamine; 4-((R)-3-Methylamino-pyrrolidin-1-yl)-7-trifluoromethyl-benzo[4,5]furo[3,2-d]pyrimidin-2-ylamine; 6-Chloro-4-((R)-3-methylamino-pyrrolidin-1-yl)-benzo[4,5]furo[3,2-d]pyrimidin-2-ylamine; 6-Methyl-4-((R)-3-methylamino-pyrrolidin-1-yl)-benzo[4,5]furo[3,2-d]pyrimidin-2-ylamine; 6-Methoxy-4-((R)-3-methylamino-pyrrolidin-1-yl)-benzo[4,5]furo[3,2-d]pyrimidin-2-ylamine; 8-Chloro-4-[3-(cyclopropylmethyl-amino)-pyrrolidin-1-yl]-benzo[4,5]furo[3,2-d]pyrimidin-2-ylamine; 8-Chloro-4-((R)-3-dimethylamino-pyrrolidin-1-yl)-benzo[4,5]furo[3,2-d]pyrimidin-2-ylamine; 4-((R)-3-Amino-pyrrolidin-1-yl)-8-chloro-benzo[4,5]furo[3,2-d]pyrimidin-2-ylamine; [8-Chloro-4-((R)-3-methylamino-pyrrolidin-1-yl)-benzo[4,5]furo[3,2-d]pyrimidin-2-yl]-methyl-amine; [8-Chloro-4-((R)-3-methylamino-pyrrolidin-1-yl)-benzo[4,5]furo[3,2-d]pyrimidin-2-yl]-dimethyl-amine; N-[8-Chloro-4-((R)-3-methylamino-pyrrolidin-1-yl)-benzo[4,5]furo[3,2-d]pyrimidin-2-yl]-acetamide; N-[8-Chloro-4-((R)-3-methylamino-pyrrolidin-1-yl)-benzo[4,5]furo[3,2-d]pyrimidin-2-yl]-methanesulfonamide; [8-Chloro-4-((R)-3-methylamino-pyrrolidin-1-yl)-benzo[4,5]furo[3,2-d]pyrimidin-2-yl]-cyclopropyl-amine. Some of said compounds and/or salts or esters thereof, will exist in different stereoisomeric forms. All of these forms are subjects of the invention, provided that the amino group attached to the pyrrolidine ring in 4-position of the pyrimidine ring shows R-configuration.

In another embodiment, selective Histamine H4 antagonists are selected from those described in the international Patent Application WO2007/090854: [1-(2-Ethylamino-8-chlorobenzo[4,5]furo[3,2-d]-pyrimidin-4-yl)azetidin-3-yl]N-ethyl amine; N-[1-(2-Amino-8-chlorobenzo[4,5]furo[3,2-d]pyrimidin-4-yl)azetidin-3-yl]N-methyl amine; 4-(3-Methylamino-azetidin-1-yl)-benzo[4,5]furo[3,2-d]pyrimidin-2-ylamine; 8-Bromo-4-(3-methylamino-azetidin-1-yl)-benzo[4,5]furo[3,2-d]pyrimidin-2-ylamine; 8-Methyl-4-(3-methylamino-azetidin-1-yl)-benzo[4,5]furo[3,2-d]pyrimidin-2-ylamine; 8-Fluoro-4-(3-methylamino-azetidin-1-yl)-benzo[4,5]furo[3,2-d]pyrimidin-2-ylamine; 8-Methoxy-4-(3-methylamino-azetidin-1-yl)-benzo[4,5]furo[3,2-d]pyrimidin-2-ylamine; 4-(3-Methylamino-azetidin-1-yl)-8-trifluoromethoxy-benzo[4,5]furo[3,2-d]pyrimidin-2-ylamine; 9-Fluoro-4-(3-methylamino-azetidin-1-yl)-benzo[4,5]furo[3,2-d]pyrimidin-2-ylamine; 9-Methyl-4-(3-methylamino-azetidin-1-yl)-benzo[4,5]furo[3,2-d]pyrimidin-2-ylamine; 9-Methoxy-4-(3-methylamino-azetidin-1-yl)-benzo[4,5]furo[3,2-d]pyrimidin-2-ylamine; 7-Methyl-4-(3-methylamino-azetidin-1-yl)-benzo[4,5]furo[3,2-d]pyrimidin-2-ylamine; 7-Methoxy-4-(3-methylamino-azetidin-1-yl)-benzo[4,5]furo[3,2-d]pyrimidin-2-ylamine; 4-(3-Methylamino-azetidin-1-yl)-7-trifluoromethyl-benzo[4,5]furo[3,2-d]pyrimidin-2-ylamine; 6-Chloro-4-(3-methylamino-azetidin-1-yl)-benzo[4,5]furo[3,2-d]pyrimidin-2-ylamine; 6-Methyl-4-(3-methylamino-azetidin-1-yl)-benzo[4,5]furo[3,2-d]pyrimidin-2-ylamine; 6-Methoxy-4-(3-methylamino-azetidin-1-yl)-benzo[4,5]furo[3,2-d]pyrimidin-2-ylamine; 4-(3-Amino-azetidin-1-yl)-8-chloro-benzo[4,5]furo[3,2-d]pyrimidin-2-ylamine; [8-Chloro-4-(3-methylamino-azetidin-1-yl)-benzo[4,5]furo[3,2-d]pyrimidin-2-yl]-methyl-amine; [8-Chloro-4-(3-methylamino-azetidin-1-yl)benzo[4,5]furo[3,2-d]pyrimidin-2-yl]-dimethyl-amine; N-[8-Chloro-4-(3-methylamino-azetidin-1-yl)benzo[4,5]furo[3,2-d]pyrimidin-2-yl]-acetamide; N-[8-Chloro-4-(3-methylamino-azetidin-1-yl)benzo[4,5]furo[3,2-d]pyrimidin-2-yl]-methanesulfonamide; [8-Chloro-4-(3- methylamino-azetidin-1-yl)benzo[4,5]furo[3,2-d]pyrimidin-2-yl]-cyclopropyl-amine. Some of said compounds and/or salts or esters thereof, will exist in different stereoisomeric forms In another embodiment, selective Histamine H4 antagonists are selected from those described in the international Patent Application WO2007/039467: N-[(R,S)-1-(8-Chloro-2-methylbenzo[4,5]furo[3,2-d]-pyrimidin-4-yl)-pyrrolidin-3-yl]-N-methyl amine; N-[(R,S)-1-(8-Chlorobenzo[4,5]furo[3,2-d]-pyrimidin-4-yl)-pyrrolidin-3-yl]-N-methyl amine; [(R,S)-1-(8-Chloro-2-methylbenzo[4,5]furo[3,2-d]pyrimidin-4-yl)pyrrolidin-3-yl] dimethyl amine; N—[(R)-1-(8-chlorobenzo[4,5]furo[3,2-d]pyrimidin-4-yl)pyrrolidin-3-yl] N-methyl amine; N—[(S)-1-(8-chlorobenzo[4,5]furo[3,2-d]pyrimidin-4-yl)pyrrolidin-3-yl] N-methyl amine; N-[1-(8-chlorobenzo[4,5]furo[3,2-d]pyrimidin-4-yl)azetidin-3-yl] amine; N-[1-(8-chlorobenzo[4,5]furo[3,2-d]pyrimidin-4-yl)azetidin-3-ylN-methyl amine; N-1-(8-Chlorobenzo[4,5]furo[3,2-d]pyrimidin-4-yl)azetidin-3-yl]N,N-dimethyl amine; N-[1-(8-Chlorobenzo[4,5]furo[3,2-d]pyrimidin-4-yl)azetidin-3-yl]N,N-dimethyl amine; [(R,S)-1-(8-chlorobenzo[4,5]furo[3,2-d]pyrimidin-4-yl)pyrrolidin-3-yl]amine; [(R,S)-1-(8-chlorobenzo[4,5]furo[3,2-d]pyrimidin-4-yl)pyrrolidin-3-yl]dimethyl amine; [(R,S)-1-(8-methylbenzo[4,5]furo[3,2-d]pyrimidin-4-yl)pyrrolidin-3-yl]-N-methyl amine; [(R)-1-(8-chlorobenzo[4,5]furo[3,2-d]pyrimidin-4-yl)pyrrolidin-3-yl] amine; [(S)-1-(8-chlorobenzo[4,5]furo[3,2-d]pyrimidin-4-yl)pyrrolidin-3-yl]; N-[(R)-1-(8-trifluoromethylbenzo[4,5]furo[3,2-d]pyrimidin-4-yl)pyrrolidin-3-yl]N-methyl amine; N—[(S)-1-(8-trifluoromethylbenzo[4,5]furo[3,2-d]pyrimidin-4-yl)pyrrolidin-3-yl]N-methyl amine; N—[(R)-1-(8-methylbenzo[4,5]furo[3,2-d]pyrimidin-4-yl)pyrrolidin-3-yl]N-methyl amine; N—[(S)-1-(8-methylbenzo[4,5]furo[3,2-d]pyrimidin-4-yl)pyrrolidin-3-yl]N-methyl amine; N-[(R)-1-(8-chloro-2-trifluoromethylbenzo[4,5]furo[3,2-d]pyrimidin-4-yl)pyrrolidin-3-yl]N-methyl amine; N—[(S)-1-(8-chloro-2-trifluoromethylbenzo[4,5]furo[3,2-d]pyrimidin-4-yl)pyrrolidin-3-yl]N-methyl amine; N-[1-(8-chlorobenzo[4,5]furo[3,2-d]pyrimidin-4-yl)azetidin-3-yl]N-ethyl amine; [(R,S)-1-(8-chlorobenzo[4,5]furo[3,2-d]pyrimidin-4-yl)-3-methylpyrrolidin-3-yl]-N-methyl amine; N-[1-(8-chlorobenzo[4,5]furo[3,2-d]pyrimidin-4-yl)azetidin-3-yl]N-cyclopropyl amine; and [(3RS,4RS)-1-(8-chlorobenzo[4,5]furo[3,2-d]pyrimidin-4-yl)-4-fluoropyrrolidin-3-yl]N-methyl amine. Some of said compounds and/or salts or esters thereof, will exist in different stereoisomeric forms.

In another embodiment, selective Histamine H4 antagonists are selected from those described in the international Patent Application WO2009/071625: 10-[(3R)-1-azabicyclo[2.2.2]oct-3-ylmethyl]-10H-phenothiazine (dextrorotatory enantiomer); 10-[(3S)-1-azabicyclo[2.2.2]oct-3-ylmethyl]-10H-phenothiazine (levorotatory enantiomer); the racemic mixture of the two enantiomers 10-[(3R,3S)-1-azabicyclo[2.2.2]oct-3-ylmethyl]-10H-phenothiazine.

In another embodiment, selective Histamine H4 antagonists are selected from those described in the international Patent Application WO2009/134726: 4-piperazin-1-yl-5,6,7a,8,9,10,11,11a-octahydro[1]benzofuro[2,3-h]quinazolin-2-amine; 4-[(3R)-3-(methylamino)pyrrolidin-1-yl]-5,6,7a,8,9,10,11,11a-octahydro[1]benzofuro[2,3-h]quinazolin-2-amine; (7aS,11aS)-4-piperazin-1-yl-5,6,7a,8,9,10,11,11a-octahydro[1]benzofuro[2,3-h]quinazolin-2-amine; (7aR,11aR)-4-piperazin-1-yl-5,6,7a,8,9,10,11,11a-octahydro[1]benzofuro[2,3-h]quinazolin-2-amine; 4-(4-methyl-1,4-diazepan-1-yl)-5,6,7a,8,9,10,11,11a-octahydro[1]benzofuro[2,3-h]quinazolin-2-amine; 4-(4-methylpiperazin-1-yl)-5,6,7a,8,9,10,11,11a-octahydro[1]benzofuro[2,3-h]quinazolin-2-amine; 4-[(3R)-3-aminopyrrolidin-1-yl]-7a,8,9,10,11,11a-hexahydro[1]benzofuro[2,3-h]quinazolin-2-amine; 4-[(1R,5S)-3,6-diazabicyclo[3.2.0]hept-6-yl]-7a,8,9,10,11,11a-hexahydro[1]benzofuro[2,3-h]quinazolin-2-amine; 4-(1,4-diazepan-1-yl)-5,6,7a,8,9,10,11,11a-octahydro[1]benzofuro[2,3-h]quinazolin-2-amine; 4-(4-isopropyl-1,4-diazepan-1-yl)-5,6,7a,8,9,10,11,11a-octahydro[1]benzofuro[2,3-h]quinazolin-2-amine; 4-(4-cyclobutyl-1,4-diazepan-1-yl)-5,6,7a,8,9,10,11,11a-octahydro[1]benzofuro[2,3-h]quinazolin-2-amine; trans-4-piperazin-1-yl-5,6,6a,7,8,9,10,10a-octahydrobenzo[h]quinazolin-2-amine; cis-4-piperazin-1-yl-5,6,6a,7,8,9,10,10a-octahydrobenzo[h]quinazolin-2-amine; trans-4-[3-(methylamino)azetidin-1-yl]-5,6,6a,7,8,9,10,10a-octahydrobenzo[h]quinazolin-2-amine; trans-4-[3-(ethylamino)azetidin-1-yl]-5,6,6a,7,8,9,10,10a-octahydrobenzo[h]quinazolin-2-amine; trans-4-[(3R)-3-(methylamino)pyrrolidin-1-yl]-5,6,6a,7,8,9,10,10a-octahydrobenzo[h]quinazolin-2-amine; trans-4-[(3R)-3-aminopyrrolidin-1-yl]-5,6,6a,7,8,9,10,10a-octahydrobenzo[h]quinazolin-2-amine; trans-4-octahydro-6H-pyrrolo[3,4-b]pyridin-6-yl-5,6,6a,7,8,9,10,10a-octahydrobenzo[h]quinazolin-2-amine; cis-4-[(3R)-3-(methylamino)pyrrolidin-1-yl]-5,6,6a,7,8,9,10,10a-octahydrobenzo[h]quinazolin-2-amine; cis-4-[(3R)-3-aminopyrrolidin-1-yl]-5,6,6a,7,8,9,10,10a-octahydrobenzo[h]quinazolin-2-amine; cis-4-[cis-octahydro-6H-pyrrolo[3,4-b]pyridin-6-yl]-5,6,6a,7,8,9,10,10a-octahydrobenzo[h]quinazolin-2-amine; cis-4-[3-(methylamino)azetidin-1-yl]-5,6,6a,7,8,9,10,10a-octahydrobenzo[h]quinazolin-2-amine; cis-4-[3-(ethylamino)azetidin-1-yl]-5,6,6a,7,8,9,10,10a-octahydrobenzo[h]quinazolin-2-amine; 4-cis-octahydro-6H-pyrrolo[3,4-6]pyridin-6-yl-6,7,7a,8,11,11a-hexahydro-5H-8,11-ethanobenzo[6,7]cyclohepta[1,2-d]pyrimidin-2-amine; 4-[(3R)-3-(methylamino)pyrrolidin-1-yl]-6,7,7a,8,11,11a-hexahydro-5H-8,11-ethanobenzo[6,7]cyclohepta[1,2-d]pyrimidin-2-amine; 4-piperazin-1-yl-6,7,7a,8,11,11a-hexahydro-5H-8,11-ethanobenzo[6,7]cyclohepta[1,2-d]pyrimidin-2-amine; 4-cis-octahydro-6H-pyrrolo[3,4-b]pyridin-6-yl-6,7,7a,8,9,10,11,11a-octahydro-5H-8,11-ethanobenzo[6,7]cyclohepta[1,2-d]pyrimidin-2-amine; or 4-[(3R)-3-(methylamino)pyrrolidin-1-yl]-6,7,7a,8,9,10,11,11a-octahydro-5H-8,11-ethanobenzo[6,7]cyclohepta[1,2-d]pyrimidin-2-amine.

In another embodiment, selective Histamine H4 antagonists are selected from those described in the international Patent Application WO2009/114575: (R)-4'-(3-(methylamino)pyrrolidin-1-yl)-6',7'-dihydro-5H-spiro[cyclopentane-1,8'-quinazolin]-2'-amine; 4'-(piperazin-1-yl)-6',7'-dihydro-5H-spiro[cyclopentane-1,8'-quinazolin]-2'-amine; 4'-(3-(methylamino)azetidin-1-yl)-6',7'-dihydro-5H-spiro[cyclopentane-1,8'-quinazolin]-2'-amine; (R)-4'-(3-aminopyrrolidin-1-yl)-6'7'-dihydro-5'H-spiro[cyclopentane-1,8'-quinazolin]-2'-amine; (S)-4'-(3-aminopyrrolidin-1-yl)-6'7'-dihydro-5'H-spiro[cyclopentane-1,8'-quinazolin]-2'-amine; 4'-((3aR,6aR)-hexahydropyrrolo[3,4-b]pyrrol-1(2H)-yl)-6I,7I-dihydro-5H-spiro[cyclopentane-1,8'-quinazolin]-2'-amine; 4'-((3aS,6aS)-hexahydropyrrolo[3,4-b]pyrrol-1(2H)-yl)-6'7'-dihydro-5H-spiro[cyclopentane-1,8'-quinazolin]-2'-amine; 4'-(1,4-diazepan-1-yl)-6',7'-dihydro-5'H-spiro[cyclopentane-1,8'-quinazolin]-2'-amine; 4'-((4aR,7aR)-tetrahydro-1H-pyrrolo[3,4-b]pyridin-6(2H,7H,7aH)-yl)-6',7'-dihydro-5'H-spiro[cyclopentane-1,8'-quinazolin]-2'-amine; N4'-(1-methylpiperidin-4-yl)-6',7'-dihydro-5H-spiro[cyclopentane-1,8'-quinazoline]-2',4'-diamine; methyl 4-amino-1-(2'-amino-6',7'-dihydro-5'H-spiro[cyclopentane-1,8'-quinazoline]-4'-yl)piperidine-4-carboxylate; 4-amino-1-(2'-amino-6',7'-dihydro-5H-spiro

[cyclopentane-1,8'-quinazoline]-4'-yl)piperidine-4-carboxylic acid; 4'-(3-aminoazetidin-1-yl)-6',7'-dihydro-5'H-spiro[cyclopentane-1,8'-quinazolin]-2'-amine; 4'-(2-(dimethylamino)ethoxy)-6',7'-dihydro-5'H-spiro[cyclopentane-1,8'-quinazolin]-2'-amine; (R)-4'-(1-methylpyrrolidin-3-yloxy)-6'7'-dihydro-5'H-spiro[cyclopentane-1,8'-quinazolin]-2'-amine; 4-(piperazin-1-yl)-5,6,7,8-tetrahydrospiro[cyclohepta[d]pyrimidine-9,1'-cyclohexan]-2-amine; (R)-4-(3-aminopyrrolidin-1-yl-5,6,7,8-tetrahydrospiro[cyclohepta[d]pyrimidine-9,1'-cyclohexan]-2-amine; 4-((4aR,7aR)-tetrahydro-1H-pyrrolo[3,4-b]pyridin-6(2H,7H,7aH)-yl)-5,6,7,8-tetrahydrospiro[cyclohepta[d]pyrimidine-9,1'-cyclohexan]-2-amine; 4-(piperazin-1-yl)-1',3',5,6,7,8-hexahydrospiro[cyclohepta[d]pyrimidine-9,2'-inden]-2-amine; and (R)-4-(3-aminopyrrolidin-1-yl)-1',3',5,6,7,8-hexahydrospiro[cyclohepta[d]pyrimidine-9,2'-inden]-2-amine.

In another embodiment, selective Histamine H4 antagonists are selected from those described in the international Patent Application WO2008/060767: 6-Methyl-4-[(3R)-3-methylamino-pyrrolidin-1-yl]-5,6-dihydro-benzo[h]quinazolin-2-ylamine; 6-Methyl-4-(3-methylamino-azetidin-1-yl)-5,6-dihydro-benzo[h]quinazolin-2-ylamine; 4-(3-Methylamino-azetidin-1-yl)-6,7-dihydro-5H-benzo[6,7]cyclohepta[1,2-d]pyrimidin-2-ylamine; 6-Methyl-4-piperazin-1-yl-5,6-dihydro-benzo[h]quinazolin-2-ylamine; 4-(3-(R)-Methylamino-pyrrolidin-1-yl)-6,7-dihydro-5H-benzo[6,7]cydohepta[1,2-d]pyrimidin-2-ylamine; 4-Piperazin-1-yl-6,7-dihydro-5H-benzo[6,7]cyclohepta[1,2-d]pyrimidin-2-ylamine; 1-(3-Methylamino-azetidin-1-yl)-10H-9-oxa-2,4-diaza-phenanthren-3-ylamine; 1-{3-(R)-Methylamino-pyrrolidin-1-yl)-10H-9-oxa-2,4-diaza-phenanthren-3-ylamine; 1-Piperazin-1-yl-10H-9-oxa-2,4-diaza-phenanthren-3-ylamine; 10-Fluoro-4-(3-(R)-methylamino-pyrrolidin-1-yl)-6,7-dihydro-5H-benzo[6,7]cyclohepta[1,2-d]pyrimidin-2-ylamine; 10-Fluoro-4-(3-methylamino-azetidin-1-yl)-6,7-dihydro-5H-benzo[6,7]cyclohepta[1,2-d]pyrimidin-2-ylamine; 10-Fluoro-4-piperazin-1-yl-6,7-dihydro-5H-benzo[6,7]cyclohepta[1,2-d]pyrimidin-2-ylamine; 4-[(3S)-3-Methylamino-pyrrolidin-1-yl]-6,7-dihydro-5H-benzo[6,7]cyclohepta[1,2-d]pyrimidin-2-ylamine; 4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine; 4-((3R)-3-Amino-pyrrolidin-1-yl)-6,7-dihydro-5H-benzo[6,7]cyclohepta[1,2-d]pyrimidin-2-ylamine; 4-((1S,4S)-2,5-Diaza-bicyclo[2.2.1]hept-2-yl)-6,7-dihydro-5H-benzo[6,7]cyciohepta[1,2-d]pyrimidin-2-ylamine; 4-(3-Piperidin-1-yl-pyrrolidin-1-yl)-6,7-dihydro-5H-benzo[6,7]cyclohepta[1,2-d]pyrimidin-2-ylamine; 4-{(3aR,6aR)-Hexahydro-pyrrolo[3,4-b]pyrrol-1-yl)-6,7-dihydro-5H-benzo[6,7]cyclohepta[1,2-d]pyrimidin-2-ylamine; 4-Piperazin-1-yl-5,6,7,8-tetrahydro-1,3-diaza-dibenzo[a,c]cycloocten-2-ylamine; 4-Piperazin-1-yl-6,7,8,9-tetrahydro-5H-1,3-diaza-dibenzo[a,c]cyclononen-2-ylamine; 4-(Hexahydro-pyrrolo[3,4-c]pyrrol-2-yl)-6,7-dihydro-5H-benzo[6,7]cyclohepta[1,2-d]pyrimidin-2-ylamine; 4-{3-(R)-Methylamino-pyrrolidin-1-yl)-6,7,8,9-tetrahydro-5H-1,3-diaza-dibenzo[a,c]cyclononen-2-ylamine; 4-({R)-3-Amino-pyrrolidin-1-yl)-6,7,8,9-tetrahydro-5H-1,3-diaza-dibenzo[a,c]cyclononen-2-ylamine; 4-{(S)-3'Amino-pyrrolidin-1-yl)-6,7,8,9-tetrahydro-5H-1,3-diaza-dibenzo[a,c]cyclononen-2-ylamine; 4-(3-Methylamino-azetidin-1-yl)-6,7,8,9-tetrahydro-5H-1,3-diaza-dibenzo[a,c]cyclononen-2-ylamine; 4-{(3aS,6aS)-Hexahydro-pyrrolo[3,4-b]pyrrol-1-yl)-6,7,8,9-tetrahydro-5H-1,3-diaza-dibenzo[a,c]cyclononen-2-ylamine; 4-((1S,4S)-2,5-Diaza-bicyclo[2.2.1]hept-2-yl)-6,7,8,9-tetrahydro-5H-1,3-diaza-dibenzo[a,c]cyclononen-2-ylamine; 4-{4-Methyl-piperazin-1-yl)-5,6-dihydro-7-oxa-1,3-diaza-dibenzo[a,c]cyclohepten-2-ylamine; 4-Piperazin-1-yl-5,6-dihydro-7-oxa-1,3-diaza-dibenzo[a,c]cyclohepten-2-ylamine; 4-((R)-3-Methylamino-pyrrolidin-1-yl)-5,6-dihydro-7-oxa-1,3-diaza-dibenzo[a,c]cyclohepten-2-ylamine, 4-(3-Methylamino-azetidin-1-yl)-5,6-dihydro-7-oxa-1,3-diaza-dibenzo[a,c]cyclohepten-2-ylamine; 4-(3-Methylamino-azetidin-1-yl)-5,6-dihydro-7-thia-1,3-diaza-dibenzo[a,c]cyclohepten-2-ylamine; 4-(3-(R)-Methylamino-pyrrolidin-1-yl)-5,6-dihydro-7-thia-1,3-diaza-dibenzo[a,c]cyclohepten-2-ylamine; 4-{3-(R)-Amino-pyrrolidin-1-yl)-5,6-dihydro-7-thia-1,3-diaza-dibenzo[a,c]cyclohepten-2-ylamine; 4-Piperazin-1-yl-5,6-dihydro-7-thia-1,3-diaza-dibenzo[a,c]cyclohepten-2-ylamine; 4-(3-Methylamino-azetidin-1-yl)-7-oxo-6,7-dihydro-5H-7λ4-thia-1,3-diaza-dibenzo[a,c]cyclohepten-2-ylamine; 4-(3-Methylamino-azetidin-1-yl)-7,7-dioxo-6,7-dihydro-5H-7λ6-thia-1,3-diaza-dibenzo[a,c]cyclohepten-2-ylamine; 4-(3-(R)-Methylamino-pyrrolidin-1-yl)-5,6-dihydro-benzo[h]quinazolin-2-ylamine; 4-(3-Methylamino-azetidin-1-yl)-5t6-dihydro-benzo[h]quinazolin-2-ylamine; 4-Piperazin-1-yl-5,6-dihydro-benzo[h]quinazolin-2-ylamine; 10-chloro-4-[(3R)-3-(methylamino)pyrrolidin-1-yl]-5,6-dihydro[1]benzoxepino[5,4-d]pyrimidin-2-amine; 10-methyl-4-[(3R)-3-{methylamino)pyrrolidin-1-yl)-5,6-dihydro[1]benzoxepino[5,4-of]pyrimidin-2-amine; 10-methoxy-4-[(3R)-3-(methylamino)pyrrolidin-1-yl]-5,6-dihydro[1]benzoxepino[5,4-d]pyrimidin-2-amine; 9-chloro-4-[(3R)-3-(methylamino)pyrrolidin-1-yl]-5,6-dihydro[1]benzoxepino[5,4-d]pyrimidin-2-amine; 9-nrrethyl-4-[{3R)-3-(methylamino)pyrrolidin-1-yl]-5,6'-dihydro[1]benzoxepino[5,4-d]pyrimidin-2-amine; 9-methoxy-4-[(3R)-3-{methylamino)pyrrolidin-1-yl]-5,6-dihydro[1]benzoxepino[5,4-d]pyrimidin-2-amine; 8-chloro-4-[(3R)-3-(methylamino)pyrrolidin-1yl]-5,6-dihydro[1]benzoxepino[5,4-d]pyrimidin-2-amine; 8-Methyl-4-((R)-3-methylamino-pyrrolidin-1-yl)-5,6-dihydro-7-oxa-1,3-diaza-dibenzo[a,c]cyclohepten-2-ylamine; 8-methoxy-4-[(3R)-3-(methylamino)pyrrolidin-1-yl]-5,6-dihydro[1]benzoxepino[5,4-d]pyrimidin-2-amine; 4-[(3R)-3-(methylamino)pyrrolidin-1-yl]-5,6,7,8-tetrahydrobenzo[7,8]cycloocta[1,2-d]pyrimidin-2-amine; 4-[(3R)-3-aminopyrrolidin-1-yl]-5,6,7,8-tetrahydrobenzo[7,8]cycloocta[1,2-d]pyrimidin-2-amine; 4-[(3S)-3-aminopyrroiidin-1-yl]-5,6,7,8-tetrahydrobenzo[7,8]cycloocta[1,2-d]pyrimidin-2-amine; 4-(3-aminoazetidin-1-yl)-5,6,7,8-tetrahydrobenzo[7,8]cycloocta[1,2-d]pyrimidin-2-amine; 4-[(3aR,6aR)-hexahydropyrrolo[3,4-b]pyrrol-1(2H)-yl]-5,6,7,8-tetrahydrobenzo[7,8]cycloocta[1,2-d]pyrimidin-2-amine; 4-octahydro-6H-pyrrolo[3,4-b]pyridin-6-yl)-6,7-dihydro-5H-benzo[6,7]cyclohepta[1,2-d]pyrimidin-2-amine; 4-(2,8-diazaspiro[4.5]dec-8-yl)-6,7-dihydro-5H-benzo[6,7]cyclohepta[1,2-d]pyrimidin-2-amine; 4-(1,5-diazocan-1-yl)-6,7-dihydro-5H-benzo[6,7]cyclohepta[1,2-d]pyrimidin-2-amine; 4-{4-aminopiperidin-1-yl)-6,7-dihydro-5H-benzo[6,7]cyclohepta[1,2-d]pyrimidin-2-amine; N4-(2-azetidin-2-ylethyl)-6,7-dihydro-5H-benzo[6,7]cyclohepta[1,2-d]pyrimidine-2,4-diamine; N4-[(2R)-azetidin-2-ylmethyl]-6,7-dihydro-5H-benzo[6,7]cyclohepta[1,2-d]pyrimidine-2,4-diamine; N4-(1-methylpiperidin-4-yl)-6,7-dihydro-5H-benzo[6,7]cyclohept[1,2-d]pyrimidine-2,4-diamine; N4-[(1R,5S)-8-methyl-8-azabicyclo[3.2.1]oct-3-yl]-6,7-dihydro-5H-benzo[6,7]cyclohepta[1,2-d]pyrimidine-2,4-diamine; 4-(5-methyl-1,4-diazepan-1-yl)-6,7-dihydro-5H-benzo[6,7]cyclohepta[1,2-d]pyrimidin-2-amine; 4-(1-Methylpiperidin-4-yloxy)-6,7-dihydro-5H-benzo[6,7]cyclohepta[1,2-d]pyrimidin-2-ylamine; 4-(1-methyl-piperidin-3-yloxy)-6,7-dihydro-5H-benzo[6,7]cyclohepta[1,2-d]pyrimidin-2-ylamine; 4-((R)-1-Methyl-pyrrolidin-3-yloxy)-6,7-dihydro-5H-benzo[6,7]cyclohepta[1,2-d]pyrimidin-2-ylamine; 4-((S)-1-Methyl-pyrrolidin-3-yloxy)-6,7-dihydro-5H-benzo[6,7]cyclohepta[1,2-d]pyrimidin-2-ylamine, 4-(Piperidin-4-yloxy)-6,7-dihydro-5H-benzo[6,7]cyclohepta[1,2-d]pyrimidin-2-ylamine; 4-((S)-Pyrrolidin-3-yloxy)-6,7-dihydro-5H-benzo[6,7]cyclohepta[1,2-d]pyrimidin-2-ylamine, 4-(2-Dimethylamino-ethoxy)-6,7-dihydro-5H-benzo[6,7]cyclohepta[1,2-d]pyrimidin-2-ylamine; 4-(1,9-Diaza-spiro[5.5]undec-9-yl)-6,7-dihydro-5H-benzo[6,7]cyclohepta[1,2-d]pyrimidin-2-ylamine; 4-((R)-3-Dimethylamino-pyrrolidin-1-yl)-6,7-dihydro-5H-benzo[6,7]cyclohepta[1,2-d]pyrimidin-2-ylamine; 4-(2,6-Diaza-spiro[3.5]non-2-yl)-6,7-dihydro-5H-benzo[6,7]cyclohepta[1,2-d]pyrimidin-2-ylamine; 4-(2,5-Diaza-spiro[3.5]non-2-yl)-6,7-dihydro-5H-benzo[6,7]cyclohepta[1,2-d]pyrimidin-2-ylamine; 4-(Octahydro-pyrrolo[3,4-c]pyridin-2-yl)-6,7-dihydro-5H-benzo[6,7]cyclohepta[1,2-d]pyrimidin-2-ylamine; 4-(Octahydro-pyrrolo[1,2-a]pyrazin-2-yl)-6,7-dihydro-5H-benzo[6,7]cyclohepta[1,2-d]pyrimidin-2-ylamine; 4-(3,6-Diaza-bicyclo[3.2.1]oct-6-yl)-6,7-dihydro-5H-benzo[6,7]cyclohepta[1,2-d]pyrimidin-2-ylamine; 4-(2,6-Diaza-bicyclo[3.2.1]oct-2-yl)-6,7-dihydro-5H-benzo[6,7]cyclohepta[1,2-d]pyrimidin-2-ylamine; N-(4-Piperazin-1-yl-6,7-dihydro-5H-benzo[6,7]cyclohepta[1,2-d]pyrimidin-2-yl)-acetamide, N-(4-Piperazin-1-yl-6,7-dihydro-5H-benzo[6,7]cyclohepta[1,2-d]pyrimidin-2-yl)-benzamide, 4-(5-Methyl-octahydro-pyrrolo[3,4-c]pyridin-2-yl)-6,7-dihydro-5H-benzo[6,7]cyclohepta[1,2-d]pyrimidin-2-ylamine, 4-(3-Methyl-3,6-diaza-bicyclo[3.2.1]oct-6-yl)-6,7-dihydro-5H-benzo[6,7]cyclohepta[1,2-d]pyrimidin-2-ylamine, 2-Dimethylamino-N-(4-piperazin-1-yl-6,7-dihydro-5H-benzo[6,7]cyclohepta[1,2-d]pyrimidin-2-yl)-acetamide; 2-Methylamino-N-(4-piperazin-1-yl-6,7-dihydro-5H-benzo[6,7]cyclohepta[1,2-d]pyrimidin-2-yl)-acetamide; 2-Amino-N-(4-piperazin-1-yl-6,7-dihydro-5H-benzo[6,7]cyclohepta[1,2-d]pyrimidin-2-yl)-acetamide; 1-Methyl-3-(4-piperazin-1-yl-6,7-dihydro-5H-benzo[6,7]cyclohepta[1,2-d]pyrimidin-2-yl)-urea; 4-Amino-N-(4-piperazin-1-yl-6,7-dihydro-5H-benzo[6,7]cyclohepta[1,2-d]pyrimidin-2-yl)-butyramide; 6-{2-pyridin-3-ylmethylamino-6,7-dihydro-5H-benzo[6,7]cyclohepta[1,2-d]pyrimidin-4-yl)octahydro-1H-pyrrolo[3,4-b]pyridine; 3-Amino-N-(4-piperazin-1-yl-6,7-dihydro-5H-benzo[6,7]cyclohepta[1,2-d]pyrimidin-2-yl)-propionamide; 4-[1,4,7]Triazonan-1-yl-6,7-dihydro-5H-benzo[6,7]cydohepta[1,2-d]pyrimidin-2-ylamine; N,N-Dimethyl-N'-(4-piperazin-1-yl-6,7-dihydro-5H-benzo[6,7]cyclohepta[1,2-d]pyrimidin-2-yl)-ethane-1,2-diamine; 4-(Octahydro-pyrrolo[3,4-b]pyridin-6-yl)-5,6-dihydro-7-thia-1,3-diaza-dibenzo[a,c]cyclohepten-2-ylamine; 4-((R)-3-Methylamino-pyrrolidin-1-yl)-6,7,9,10,11,12-hexahydro-5H-1,3-diaza-benzo[3,4]cyclohepta[1,2-b]naphthalen-2-ylamine; 4'(Octahydro-pyrrolo[3,4-b]pyridin-6-yl)-6,7,9,10,11,12-hexahydro-5H-1,3-diaza-benzo[3,4]cyclohepta[1,2-Nnaphthalen-2-ylamine; 4-Piperazin-1-yl-6,7,9,10,11,12-hexahydro-5H-1,3-diaza-benzo[3,4]cyclohepta[1,2-Nnaphthalen-2-ylamine; 9-Iodo-4-({R)-3-methylamino-pyrrolidin-1-yl)-5,6-dihydro-7-oxa-1,3-diaza-dibenzo[a,c]cyclohepten-2-ylamine; 9-lodo-4-piperazin-1-yl-5,6-dihydro-7-oxa-1,3-diaza-dibenzo[a,c]cyclohepten-2-ylamine; 9-Iodo-4-octahydro-pyrrolo[3,4-b]pyridin-6-yl-5,6-dihydro-7-oxa-1,3-diaza-dibenzo[a,c]cyclohepten-2-ylamine; 2,4-Di-piperazin-1-yl-6,7-dihydro-5H-benzo[6,7]cyclohepta[1,2-d]pyrimidine; 2-Amino-4-octahydro-pyrrolo[3,4-b]pyridin-6-yl-5,6-dihydro-7-oxa-1,3-diaza-dibenzo[a,c]cycloheptene-9-carbonitrile; 4-Octahydro-pyrrolo[3,4-b]pyridin-6-yl-9-phenyl-5,6-dihydro-7-oxa-1,3-diaza-dibenzo[a,c]cyclohepten-2-ylamine; 4-Octahydro-pyrrolo[3,4-b]pyridin-6-yl-9-pyridin-3-yl-5,6-dihydro-7-oxa-1,3-diaza-dibenzo[a,c]cyclohepten-2-ylamine; 4-((R)-3-Methylamino-pyrrolidin-1-yl)-6,7-dihydro-5-thia-1,3-diaza-dibenzo[a,c]cyclohepten-2-ylamine; 2-Amino-4-octahydro-pyrrolo[3,4-b]pyridin-6-yl-5,6-dihydro-7-oxa-1,3-diaza-dibenzo[a,c]cycloheptene-9-carboxylic acid methyl ester; 4-P iperazin-1-yl-6,7-dihydro-5-thia-1,3-diaza-dibenzo[a,c]cyclohepten-2-ylamine; 4-(Octahydro-pyrrolo[3,4-b]pyridin-6-yl)-6,7-dihydro-5-thia-1,3-diaza-dibenzo[a.c]cyclohepten-2-ylamine; 4-((R)-3-Methylamino-pyrrolidin-1-yl)-5,5-dioxo-6,7-dihydro-5H-5λ6-thia-1,3-diaza-dibenzo[a,c]cyclohepten-2-ylamine; 4-((R)-3-Methylamino-pyrrolidin-1-yl)-5-oxo-6,7-dihydro-5-thia-1,3-diaza-dibenzo[a,c]cyclohepten-2-ylamine; N4-(3-Piperidin-1-yl-propyl)-6,7-dihydro-5H-benzo[6,7]cyclohepta[1,2-]pyrimidine-2,4-diamine; 4-(4-Dimethylamirro-piperidin-1-yl)-6,7-dihydro-5H-benzo[6,7]cyclohepta[1,2-d]pyrimidin-2-ylamine; 10-fluoro-4-octahydro-6H-pyrrolo[3,4-b]pyridin-6-yl-6,7-dihydro-5H-benzo[6,7]cyclohepta[1,2-d]pyrimidin-2-amine; 4-[1,4]Diazepan-1-yl-6,7-dihydro-5H-benzo[6,7]cyclohepta[1,2-d]pyrimidin-2-ylamine; (1R,5S)-4-(3,6-Diaza-bicyclo[3.2.0]hept-6-yl-6,7-dihydro-5H-benzo[6,7]cyclohepta[1,2-d]pyrimidin-2-ylamine; 4-Piperazin-1-yl-6,7-dihydro-5H-benzo[6,7]cyclohepta[1,2-d]pyrimidine; (3aS,6aS)-4-(Hexahydro-pyrrolo[3,4-b]pyrrol-1-yl)-6,7-dihydro-5H-benzo[6,7]cyclohepta[1,2-d]pyrimidin-2-ylamine; {1S,5S)-4-(3,6-Diaza-bicyclo[3.2.0]hept-3-yl)-6,7-dihydro-5H-benzo[6,7]cyclohepta[1,2-d]pyrimidin-2-ylamine; N4-Piperidin-3-yl-6,7-dihydro-5H-benzo[6,7]cyclohepta[1,2-d]pyrimidine-2,4-diamine; N4(Octahydro-isoindol-4-yl)-6,7-dihydro-5H-benzo[6,7]cyclohepta[1,2-d]pyrimidine-2,4-diamine; Methyl-{4-piperazin-1-yl-6,7-dihydro-5H-benzo[6,7]cyclohepta[1,2-d]pyrimidin-2-yl)-amine; 4-{3-(R)-Methylamino-pyrrolidin-1-yl)-6,7-dihydro-5H-benzo[6,7]cyclohepta[1,2-d]pyrimidine; [1-(6,7-Dihydro-5H-benzo[6,7]cyclohepta[1,2-d]pyrimidin-4-yl)-azetidin-3-yl]-amine; 8,10-Dimethyl-piperazin-1-yl-6,7-dihydro-5H-benzo[6,7]cyclohepta[1,2-d]pyrimidin-2-ylamine; 6-{2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine; (2-Amino-4-piperazin-1-yl-6,7-dihydro-5H-benzo[6,7]cyclohepta[1,2-d]pyrimidin-10-yl)-methyl-carbannic acid methyl ester; 10-N-Methyl-4-piperazin-1-yl-6,7-dihydro-5H-benzo[6,7]cyclohepta[1,2-d]pyrimidine-2,10-diamine; (2-Amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester; 10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine; N-{2-Amino-4-piperazin-1-yl-6,7-dihydro-5H-benzo[6,7]cyclohepta[1,2-d]pyrimidin-11-yl)-acetamide; 4-(Octahydro-pyrrolo[3,4-b]pyridin-6-yl)-6,7-dihydro-5H-benzo[6,7]cyclohepta[1,2-d]pyrimidine-2-carboxylic acid methyl ester; 4-(Octahydro-pyrrolo[3,4-b]pyridin-6-yl)-6,7-dihydro-5H-benzo[6,7]cyclohepta[1,2-d]pyrimidine-2-carboxylic acid.

In another embodiment, selective Histamine H4 antagonists are selected from those described in the international Patent Application WO2009137492: 4-octahydro-6H-pyrrolo[3,4-b]pyridin-6-yl-6,7-dihydro-5H-thieno[2',3':6,7]cyclohepta[1,2-d]pyrimidin-2-amine; 4-[(3R)-3-aminopyrrolidin-1-yl]-6,7-dihydro-5H-thieno[2', 3': 6,7]cyclohepta[1,2- d]pyrimidin-2-amine; 4-[(3R)-3-(methylamino)pyrrolidin-1-yl]-6,7-dihydro-5H-thieno[2',3':6,7]cyclohepta[1,2-d]pyrimidin-2-amine; 4-octahydro-6H-pyrrolo[3,4-b]pyridin-6-yl-6,7-dihydro-5H-furo[2',3':6,7]cyclohepta[1,2-d]pyrimidin-2-amine; 9-methyl-4-octahydro-6H-pyrrolo[3,4-b]pyridin-6-yl-6,7-dihydro-5H-furo[2',3':6,7]cyclohepta[1,2-d]pyrimidin-2-amine; 4-[(3R)-3-aminopyrrolidin-1-yl]-9-methyl-6,7-dihydro-5H-furo[2',3':6,7]cyclohepta[1,2-d]pyrimidin-2-amine; 4-octahydro-6H-pyrrolo[3,4-b]pyridin-6-yl-6,7-dihydro-5H-furo[3',2':6,7]cyclohepta[1,2-d]pyrimidin-2-amine; 4-[(3R)-3-aminopyrrolidin-1-yl]-8-methyl-5,6,7,8-tetrahydropyrazolo[3',4':6,7]cyclohepta[1,2-d]pyrimidin-2-amine; 8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine; 4-[(3R)-3-(methylamino)pyrrolidin-1-yl]-8-phenyl-5,6,7,8-tetrahydropyrazolo[3',4':6,7]cyclohepta[1,2-d]pyrimidin-2-amine; 9-bromo-4-octahydro-6H-pyrrolo[3,4-b]pyridin-6-yl-6,7-dihydro-5H-thieno[2',3':6,7]cyclohepta[1,2-d]pyrimidin-2-amine; 4-octahydro-6H-pyrrolo[3,4-b]pyridin-6-yl-9-phenyl-6,7-dihydro-5H-thieno[2',3':6,7]cyclohepta[1,2-d]pyrimidin-2-amine; 4-[(3R)-3-aminopyrrolidin-1-yl]-6,7-dihydro-5H-pyrido[3',2':6,7]cyclohepta[1,2-d]pyrimidin-2-amine; 4-[(3R)-3-aminopyrrolidin-1-yl]-10-methyl-6,7-dihydro-5H-isoxazolo[5',4':6,7]cyclohepta[1,2-d]pyrimidin-2-amine; 4-[(4aR,7aR)-octahydro-6H-pyrrolo[3,4-b]pyridin-6-yl]-6,7-dihydro-5H-thieno[2',3':6,7]cyclohepta[1,2-d]pyrimidin-2-amine; or a pharmaceutically acceptable salt thereof.

In another embodiment, selective Histamine H4 antagonists are selected from those described in the international Patent Application WO2009123967: (R)-4-(3-aminopyrrolidin-1-yl)-9,9-dimethyl-6,7,8,9-tetrahydro-5H-cyclohepta[d]pyrimidin-2-amine; 9,9-dimethyl-4-(piperazin-1-yl)-6,7,8 9-tetrahydro-5H-cyclohepta[d]pyrimidin-5 2-amine; (R)-4-(3-aminopyrrolidin-1-yl)-9,9-diethyl-6,7,8,9-tetrahydro-5H-cyclohepta[d]pyrimidin-2-amine; (R)-4-(3-aminopyrrolidin-1-yl)-9,9-dibenzyl-6,7,8,9-tetrahydro-5H-cyclohepta[d]pyrimidin-2-amine; 8-phenyl-4-(piperazin-1-yl)-6,7,8,9-tetrahydro-5H-cyclohepta[d]pyrimidin-2-amine; 8-phenyl-4-(tetrahydro-1H-pyrrolo[3,4-b]pyridine-6 92H,7H,7aH0-yl)-6,7,8,9-tetrahydro-5H-cyclohepta[d]pyrimidin-2-amine; 4-((R)-3-(methylamino)pyrrolidin-1-yl)-8-phenyl-6,7,8,9-tetrahydro-5H-5-cyclohepta[d]pyrimidin-2-amine; 4-(3-aminoazetidin-1-yl)-8-phenyl-6,7,8,9-tetrahydro-5H-cyclohepta[d]pyrimidin-2-amine; 8-phenyl-4-(piperazine-1-yl)-5,6,7,8-tetrahydroquinazolin-2-amine; 8-phenyl-4-((4aR,7aR)-tetrahydro-1H-pyrrolo[3,4-b]pyridin-6(2H,7H ,7aH)-yl)-5,6,7,8-tetrahydroquinazolin-2-amine; 4-((R)-3-(methylamino)pyrrolidin-1-yl)-8-phenyl-5,6,7,8-tetrahydroquinazolin-2-amine; 8,8-dimethoxy-4-(piperazin-1-yl)-5,6,7,8-tetrahydroquinazolin-2-amine; 4-(piperazin-1-yl)-6,7,8,9-tetrahydro-5H-cyclohepta[d]pyrimidin-2-amine; 9-(2-methylpyridin-4-yl)-4-(piperazin-1-yl)-6,7,8,9-tetrahydro-5H-cyclohepta[d]pyrimidin-2-amine; methyl 5-(2-amino-4-(piperazin-1-yl)-6,7,8,9-tetrahydro-5H-cyclohepta[d]pyrimidin-9-yl)nicotinate; 5-(2-amino-4-(piperazin-1-yl)-6,7,8,9-tetrahydro-5H-cyclohepta[d]pyrimidin-9-yl)nicotinic acid; 4-((R)-3-(methylamino)pyrrolidin-1-yl)-9-phenyl-6,7,8,9-tetrahydro-5H-cyclohepta[d]pyrimidin-2-amine; 4-(3-(methylamino)azetidin-1-yl)-9-phenyl-6,7,8,9-tetrahydro-5H-cyclohepta[d]pyrimidin-2-amine; 9-phenyl-4-(piperazin-1-yl)-6,7,8,9-tetrahydro-5H-cyclohepta[d]pyrimidin-2-amine; 9-phenyl-4-tetrahydro-1H-pyrrolo[3,4-b]pyridine-6(2H,7H,7aH))-6,7,8,9-tetrahydro-5H-cyclohepta[d]pyrimidin-2-amine; or 5,9-phenyl-4-((4aR,7aR)-tetrahydro-1H-pyrrolo[3,4-b]pyridin-6(2H,7H,7aH)-yl)-6,7,8,9-tetrahydro-5H-cyclohepta[d]pyrimidin-2-amine.

In another embodiment, selective Histamine H4 antagonists are selected from those described in the international Patent Application WO2005/054239: 4-[octahydro-6H-pyrrolo[3,4-b]pyridin-6-yl]-6-phenylpyrimidin-2-amine; 4-(3-methoxyphenyl)-6-[octahydro-6H-pyrrolo[3,4-b]pyridin-6-yl]pyrimidin-2-amine; 3-{2-amino-6-[octahydro-6H-pyrrolo[3,4-b]pyridin-6-yl]pyrimidin-4-yl}benzonitrile; 4-(1-naphthyl)-6-[octahydro-6H-pyrrolo[3,4-b]pyridin-6-yl]pyrimidin-2-amine; 4-(3-methylphenyl)-6-[octahydro-6H-pyrrolo[3,4-b]pyridin-6-yl]pyrimidin-2-amine; 4-(3-chlorophenyl)-6-[octahydro-6H-pyrrolo[3,4-b] pyridin-6-yl]pyrimidin-2-amine 4-[octahydro-6H-pyrrolo[3,4-b]pyridin-6-yl]-6-[3-(trifluoromethyl)phenyl]pyrimidin-2-amine; 1-(3-{2-amino-6-[octahydro-6H-pyrrolo[3,4-b]pyridin-6-yl]pyrimidin-4-yl}phenyl)ethanone; 4-(3-nitrophenyl)-6-[octahydro-6H-pyrrolo [3,4-b]pyridin-6-yl]pyrimid in-2-amine; (3-{2-amino-6-[octahydro-6H-pyrrolo[3,4-b]pyridin-6-yl]pyrimidm-4-yl}phenyl)methanol; 4-(3,4-dichlorophenyl)-6-[octahydro-6H-pyrrolo[3,4-b]pyridin-6-yl]pyrimidin-2-amine; 4-(4-nitrophenyl)-6-[octahydro-6H-pyrrolo[3,4-b]pyridin-6-yl]pyrimidin-2-amine; 4-(3-fluorophenyl)-6-[octahydro-6H-pyrrolo[3,4-b]pyridin-6-yl]pyrimidin-2-amine; 5-methyl-4-[octahydro-6H-pyrrolo[3,4-b]pyridin-6-yl]-6-phenylpyrimidin-2-amine; 4-[octahydro-6H-pyrrolo[3,4-b]pyridin-6-yl]-6-(3-thienyl)pyrimidin-2-amine; 4-(3-chlorophenyl)-5-methyl-6-[octahydro-6H-pyrrolo[3,4-b]pyridin-6-yl]pyrimidin-2-amine; 5-methyl-4-(3-methylphenyl)-6-[octahydro-6H-pyrrolo [3,4-b]pyridin-6-yl]pyrimidin-2-amine; 4-(3-fluorophenyl)-5-methyl-6-[octahydro-6H-pyrrolo[3,4-b]pyridin-6-yl]pyrimidin-2-amine; 4-(3-aminopyrrolidin-1-yl)-6-phenylpyrimidin-2-amine; 4-[3-(methylamino)azetidin-1-yl]-6-phenylpyrimidin-2-amine; 4-[3-(dimethylamino)azetidin-1-yl]-6-phenylpyrimidin-2-amine; 4-(3-chlorophenyl)-6-[3-(methylamino)azetidin-1-yl]pyrimidin-2-amine; 4-[3-(methylamino)azetidin-1-yl]-6-(3-methylphenyl)pyrimidin-2-amine; 4-(3-fluorophenyl)-6-[3-(methylamino)azetidin-1-yl]pyrimidin-2-amine; 4-(3-methoxyphenyl)-6-[3-(methylamino)azetidin-1-yl]pyrimidin-2-amine; 3-{2-amino-6-[3-(methylamino)azetidin-1-yl]pyrimidin-4-yl}benzonitrile; 1-(3-{2-amino-6-[3-(methylamino)azetidin-1-yl]pyrimidin-4-yl}phenyethanone; 4-(methylamino) azetidin-1-yl]-6-(3-nitrophenyl)pyrimidin-2-amine; 3-{2-amino-6-[3-(methylamino) azetidin-1-yl]pyrimidin-4-yl}phenol; 4-(3-aminophenyl)-6-[3-(methylamino)azetidin-1-yl]pyrimidin-2-amine; 5-fluoro-4-[3-(methylamino)azetidin-1-yl]-6-phenylpyrimidin-2-amine; 5-methyl-4-[methylamino)azetidin-1-yl]-6-phenylpyrimidin-2-amine; 4-[3-(methylamino)azetidin-1-yl]-6-[3-(trifluoromethyl)phenyl] pyrimidin-2-amine; 4-[3-(dimethylamino)phenyl]-6-[3-(methylamino)azetidin-1-yl] pyrimidin-2-amine; 4-[3-(methylamino)azetidin-1-yl]-6-(1-naphthyl)pyrimidin-2-amine; 4-[3-(methylamino)azetidin-1-yl]-6-(4-methylphenyl)pyrimidin-2-amine; 4-(4-chlorophenyl)-6-[3-(methylamino)azetidin-1-yl]pyrimidin-2-amine; 4-(4-fluorophenyl)-6-[3-(methylamino)azetidin-1-yl]pyrimidin-2-amine; 4-(4-methoxyphenyl)-6-[3-(methylamino)azetidin-1-yl]pyrimidin-2-amine; 4-{2-amino-6-[3-(methylamino)azetidin-1-yl]pyrimidin-4-yl]benzonitrile; 4-[3-(methylamino)azetidin-1-yl]-6-(4-nitrophenyl)pyrimidin-2-amine; and 4-{2-amino-6-[3-(methylamino)azetidin-1-yl]pyrimidin-4-yl}phenol; 4-[(4aR,7aR)-octahydro-6H-pyrrolo[3,4-b]pyridin-6-yl]-6-phenylpyrimidin-2-amine trihydrochloride; 4-(3-methoxyphenyl)-6-[(4aR,7aR)-octahydro-6H-pyrrolo[3,4-b]pyridin-6-yl]pyrimidin-2-amine trihydrochloride; 3-{2-amino-6-[(4aR,7aR)-octahydro-6H-pyrrolo[3,4-b]pyridin-6-yl]pyrimidin-4-yl}benzonitrile trihydrochloride; 4-(1-naphthyl)-6-[(4aR,7aR)-octahydro-6H-pyrrolo[3,4-b]pyridin-6-yl]pyrimidin-2-amine trihydrochloride; 4-(3-methylphenyl)-6-[(4aR,7aR)-octahydro-6H-pyrrolo[3,4-b]pyridin-6-yl]pyrimidin-2-amine trihydrochloride; 4-(3-chlorophenyl)-6-[(4aR,7aR)-octahydro-6H-pyrrolo[3,4-b]pyridin-6-yl]pyrimidin-2-amine trihydrochloride; 4-[(4aR,7aR)-octahydro-6H-pyrrolo[3,4-b]pyridin-6-yl]-6-[3-(trifluoromethyl)phenyl]pyrimidin-2-amine trihydrochloride; 1-(3-{2-amino-6-[(4aR,7aR)-octahydro-6H-pyrrolo[3,4-b]pyridin-6-yl]pyrimidin-4-yl}phenyl)ethanone trihydrochloride; 4-(3-nitrophenyl)-6-[(4aR,7aR)-octahydro-6H-pyrrolo[3,4-b]pyridin-6-yl]pyrimidin-2-amine trihydrochloride; (3-{2-amirio-6-[(4aR,7aR)-octahydro-6H-pyrrolo[3,4-b]pyridin-6-yl]pyrimidin-4-yl}phenyl)methanol trihydrochloride; 4-(3,4-dichlorophenyl)-6-[(4aR,7aR)-octahydro-6H-pyrrolo[3,4-b]pyridin-6-yl]pyrimidin-2-amine dihydrochloride; 4-(4-nitrophenyl)-6-[(4aR,7aR)-octahydro-6H-pyrrolo[3,4-b]pyridin-6-yl]pyrimidin-2-amine dihydrochloride; 4-(3-fluorophenyl)-6-[(4aR,7aR)-octahydro-6H-pyrrolo[3,4-b]pyridin-6-yl]pyrimidin-2-amine dihydrochloride; 5-methyl-4-[(4aR,7aR)-octahydro-6H-pyrrolo[3,4-b]pyridin-6-yl]-6-phenylpyrimidin-2-amine dihydrochloride; 4-[(4aR,7aR)-octahydro-6H-pyrrolo[3,4-b]pyridin-6-yl]-6-(3-thienyl)pyrimidin-2-amine dihydrochloride; 4-(3-chlorophenyl)-5-methyl-6-[(4aR,7aR)-octahydro-6H-pyrrolo[3,4-b]pyridin-6-yl]pyrimidin-2-amine dihydrochloride; 5-methyl-4-(3-methylphenyl)-6-[(4aR,7aR)-octahydro-6H-pyrrolo[3,4-b]pyridin-6-yl]pyrimidin-2-amine dihydrochloride; and 4-(3-fluorophenyl)-5-methyl-6-[(4aR,7aR)-6ctahydro-6H-pyrrolo[3,4-b]pyridin-6-yl]pyrimidin-2-amine dihydrochloride.

In another embodiment, selective Histamine H4 antagonists are selected from those described in the international Patent Application WO2005/014556: 4-(3-aminopyrrolidin-1-yl)-6-phenylpyrimidin-2-amine trihydrochloride; 4-[3-(dimethylamino) pyrrolidin-1-yl]-6-phenylpyrimidin-2-amine trihydrochloride; 4-[3-(methylamino) pyrrolidin-1-yl]-6-phenylpyrimidin-2-amine trihydrochloride; 4-[3-(methylamino) pyrrolidin-1-yl]-6-(3-nitrophenyl)pyrimidin-2-amine trihydrochloride; 4-[(3R)-3-(methylamino)pyrrolidin-1-yl]-6-(3-nitrophenyl)pyrimidin-2-amine trihydrochloride; 4-[(3S)-3-(methylamino)pyrrolidin-1-yl]-6-(3-nitrophenyl)pyrimidin-2-amine trihydrochloride; 4-[(3S)-3-(methylamino)pyrrolidin-1-yl]-6-phenylpyrimidin-2-amine trihydrochloride; 4-[(3R)-3-(methylamino)pyrrol id in-1-yl]-6-phenylpyrimidin-2-amine trihydrochloride; 4-[3-(methylamino)pyrrolidin-1-yl]-6-(3-methylphenyl)pyrimidin-2-amine trihydrochloride; 1-(3-{2-amino-6-[3-(methylamino)pyrrolidin-1-yl]pyrimidin-4-yl}phenyl) ethanone trihydrochloride; 3-{2-amino-6-[3-(methylamino) pyrrolidin-1-yl]pyrimidin-4-yl}phenol trihydrochloride; (3-{2-amino-6-[3-(methylamino)pyrrolidin-1-yl]pyrimidin-4-yl}phenyl)methanol trihydrochloride; and 3-{2-amino-6-[3-(methylamino)pyrrolidin-1-yl]pyrimidin-4-yl}benzonitrile trihydrochloride; 3-[2-amino-6-(4-methylpiperazin-1-yl)pyrimidin-4-yl]phenol; 1-{3-[2-amino-6-(4-methylpiperazin-1-yl)pyrimidin-4-yl]phenyl}ethanone; {3-[2-amino-6-(4-methylpiperazin-1-yl)pyrimidin-4-yl]phenyl}methanol; 4-(4-methylpiperazin-1-yl)-6-[3-(trifluoromethyl)phenyl] pyrimidin-2-amine; 4-biphenyl-3-yl-6-(4-methylpiperazin-1-yl)pyrimidin-2-amine trihydrochloride; 4-[3-(dimethylamino)phenyl]-6-(4-methylpiperazin-1-yl)pyrimidin-2-amine; 4-(4-methylpiperazin-1-yl)-6-(1-naphthyl)pyrimidin-2-amine; and 3-[2-amino-6-(4-methylpiperazin-1-yl) pyrimidin-4-yl] benzonitrile.

In another embodiment, selective Histamine H4 antagonists are selected from those described in the international Patent Application WO2006/056848: (5-chloro-1H-indol-2-yl)-(4-methyl-piperazin-1-yl)-methanone; in WO02/072548: 6-bromo-4-methyl-2-{[(3aR,6aS)-5-methylhexahydropyrrolo[3,4-c]pyrrol-2(1H)-yl]carbonyl}-1H-benzimidazole and 6-fluoro-4-methyl-2-{[(3aR,6aS)-5-methylhexahydropyrrolo[3,4-c]pyrrol-2(1H)-yl]carbonyl}-1H-benzimidazole.

In another embodiment, selective Histamine H4 antagonists are selected from those described in the international Patent Application WO2007/072163: $N^4$-(Cyclopropylmethyl)-6-[(3R)-3-(methylamino)pyrrolidin-1-yl]pyrimidine-2,4-diamine, $N^4$-(Cyclopropylmethyl)-6-[(3R)-3-(methylamino)pyrrolidin-1-yl]pyrimidine-2,4-diamine tartrate, $N^4$-Isobutyl-6-[(3R)-3-(methylamino)pyrrolidin-1-yl]pyrimidine-2,4-diamine, $N^4$-(2,2-Dimethylpropyl)-6-[(3R)-3-(methylamino)pyrrolidin-1-yl]pyrimidine-2,4-diamine-N-Isobutyl-6-[(3R)-3-(methylamino)pyrrolidin-1-yl] pyrimidin-4-amine, N-(Cyclopropylmethyl)-6-[(3R)-3-(methylamino)pyrrolidin-1-yl]pyrimidin-4-amine, $N^4$-(2,2-Dimethylpropyl)-6-[(4aR*,7aR*)-octahydro-6H-pyrrolo[3,4-b]pyridin-6-yl]pyrimidine-2,4-diamine, $N^4$-Cyclopropyl-6-[(4aR*,7aR*)-octahydro-6H-pyrrolo[3,4-b]pyridin-6-yl] pyrimidine-2,4-diamine, $N^4$-Cyclobutyl-6-[(4aR*,7aR*)-octahydro-6H-pyrrolo[3,4-b]pyridin-6-yl]pyrimidine-2,4-diamine, $N^4$-(2,2-Dimethylpropyl)-6-[3-(methylamino) azetidin-1-yl]pyrimidine-2,4-diamine, 6-(3-Methylamino-azetidin-1-yl)-$N^4$-(3,3,3-trifluoro-propyl)-pyrimidine-2,4-diamine, $N^4$-Cyclopropylmethyl-6-(3-methylamino-azetidin-1-yl)-pyrimidine-2,4-diamine, $N^4$-(3,3-Dimethyl-butyl)-6-(3-methylamino-azetidin-1-yl)-pyrimidine-2,4-diamine, $N^4$-(3-Fluoro-benzyl)-6-(3-methylamino-azetidin-1-yl)-pyrimidine-2,4-diamine, $N^4$-Cyclopentylmethyl-6-(3-methylamino-azetidin-1-yl)-pyrimidine-2,4-diamine, $N^4$-Isobutyl-6-[3-(methylamino)azetidin-1-yl]pyrimidine-2,4-diamine, 6-[3-(Methylamino)azetidin-1-yl]-$N^4$-propylpyrimidine-2,4-diamine, $N^4$-(2-Methoxybenzyl)-6-[3-(methylamino)azetidin-1-yl]pyrimidine-2,4-diamine, $N^4$-(2,2-Dimethylpropyl)-6-[(3R)-3-methylpiperazin-1-yl] pyrimidine-2,4-diamine, $N^4$-Ethyl-6-(4-methylpiperazin-1-yl)pyrimidine-2,4-diamine, $N^4$-(Cyclopropylmethyl)-6-(4-methylpiperazin-1-yl)pyrimidine-2,4-diamine, 6-[3-(Methylamino)azetidin-1-yl]-$N^4$-(2-methylbutyl) pyrimidine-2,4-diamine, $N^4$-(2,5-Difluorobenzyl)-6-[3-(methylamino)azetidin-1-yl]pyrimidine-2,4-diamine, $N^4$-(2,3-Difluorobenzyl)-6-[3-(methylamino)azetidin-1-yl] pyrimidine-2,4-diamine, $N^4$-Butyl-6-[3-(methylamino) azetidin-1-yl]pyrimidine-2,4-diamine, 6-[(3R)-3-(Methylamino)pyrrolidin-1-yl]-$N^4$-(2-methylcyclopropyl) pyrimidine-2,4-diamine, $N^4$-Isobutyl-6-(4-methyl-1,4-diazepan-1-yl)pyrimidine-2,4-diamine, $N^4$-(Cyclopropylmethyl)-6-(3-pyrrolidin-1-ylazetidin-1-yl) pyrimidine-2,4-diamine, $N^4$-Bicyclo[1.1.1]pent-1-yl-6-[(3R)-3-(methylamino)pyrrolidin-1-yl]pyrimidine-2,4-diamine, 6-[3-Methyl-3-(methylamino)azetidin-1-yl]-$N^4$-propylpyrimidine-2,4-diamine, $N^4$-(2,2-Dimethylpropyl)-6-(hexahydropyrrolo[1,2-a]pyrazin-2(1H)-yl)pyrimidine-2,4-diamine, $N^4$-(2,2-Dimethylpropyl)-6-(3-pyrrolidin-1-ylazetidin-1-yl)pyrimidine-2,4-diamine, N4-(2,2-Dimethylpropyl)-6-[3-(isopropylamino)azetidin-1-yl] pyrimidine-2,4-diamine, N4-(tert-Butyl)-6-[(3R)-3-(methylamino)pyrrolidin-1-yl]pyrimidine-2,4-diamine, 6-[(3R)-3-(Methylamino)pyrrolidin-1-yl]-N$^4$-(1-methylcyclopropyl)pyrimidine-2,4-diamine, N$^4$-(tert-Butyl)-6-[(4aS*,7aS*)-octahydro-6H-pyrrolo[3,4-b]pyridin-6-yl]pyrimidine-2,4-diamine, N$^4$-(2,2-Dimethylpropyl)-6-piperazin-1-ylpyrimidine-2,4-diamine, N$^4$-(2,2-Dimethylpropyl)-6-[3-(methylamino)azetidin-1-yl]pyrimidine-2,4-diamine hydrochloride, N$^4$-(2,2-Dimethylpropyl)-6-[(3aR*,7aS*)-octahydro-5H-pyrrolo[3,2-c]pyridin-5-yl]pyrimidine-2,4-diamine, 6-Piperazin-1-yl-N$^4$-propylpyrimidine-2,4-diamine, N$^4$-(Cyclopropylmethyl)-6-[4aR,7aR]-octahydro-6H-pyrrolo[3,4-b]pyridin-6-yl]pyrimidine-2,4-diamine, N$^4$-(2,2-Dimethylpropyl)-6-[(4aS,7aS)-octahydro-6H-pyrrolo[3,4-b]pyridin-6-yl]pyrimidine-2,4-diamine N$^4$-(Cyclopropylmethyl)-6-[(3R)-3-(methylamino)pyrrolidin-1-yl]pyrimidine-2,4-diamine, N$^4$-Isopropyl-6-[(4aS,7aS)-octahydro-6H-pyrrolo[3,4-b]pyridin-6-yl]pyrimidine-2,4-diamine, 4-[3-(Methylamino)azetidin-1-yl]-6-(4-methylpiperidin-1-yl)pyrimidin-2-amine, N$^4$-(Cyclopentylmethyl)-6-[(3R)-3-(methylamino)pyrrolidin-1-yl]pyrimidine-2,4-diamine, N$^4$-Cyclobutyl-6-[(4aS,7aS)-octahydro-6H-pyrrolo[3,4-b]pyridin-6-yl]pyrimidine-2,4-diamine, 6-[(3R)-3-(Methylamino)pyrrolidin-1-yl]-N$^4$-propylpyrimidine-2,4-diamine, and, N$^4$-Ethyl-6-(4-methyl-1,4-diazepan-1-yl)pyrimidine-2,4-diamine.

In another embodiment, selective Histamine H4 antagonists are selected from those described in the international Patent Application WO2008/074445: 4-(4-Methyl-piperazin-1-yl)-benzo[4,5]furo[3,2-d]pyrimidin-2-ylamine; 8-Chloro-4-(4-methyl-piperazin-1-yl)-benzo[4,5]furo[3,2-d]pyrimidin-2-ylamine; 4-(4-Methylpiperazin-1-yl)pyrido[3',2':4,5]furo[3,2-d]pyrimidin-2-amine; 8-Chloro-4-(4-methylpiperazin-1-yl)[1]benzofuro[3,2-d]pyrimidin-2-amine; 8-Chloro-4-[(3S)-3-methylpiperazin-1-yl][1]benzofuro[3,2-d]pyrimidin-2-amine; 8-Methoxy-4-piperazin-1-yl[1]benzofuro[3,2-d]pyrimidin-2-amine, bis acetate salt; N$^4$-1-Azabicyclo[2.2.2]oct-3-yl-8-chloro[1]benzofuro[3,2-d]pyrimidine-2,4-diamine; 4-(3-Aminopyrrolidin-1-yl)-8-methoxy[1]benzofuro[3,2-d]pyrimidin-2-amine; 4-(3-Aminopyrrolidin-1-yl)-7-chloro[1]benzofuro[3,2-d]pyrimidin-2-amine; 7-Chloro-4-piperazin-1-yl[1]benzofuro[3,2-αf]pyrimidin-2-amine; 8-Chloro-4-piperazin-1-yl[1]benzofuro[3,2-d]pyrimidin-2-amine, dihydrochloride; 8-(2-Methoxyethoxy)-4-piperazin-1-yl[1]benzofuro[3,2-d]pyrimidin-2-amine; 8-Ethoxy-4-piperazin-1-yl[1]benzofuro[3,2-d]pyrimidin-2-amine; 8-Chloro-4-(3-ethylpiperazin-1-yl)[1]benzofuro[3,2-d]pyrimidin-2-amine; 8-Chloro-4-[(3S)-3-isopropylpiperazin-1-yl][1]benzofuro[3,2-d]pyrimidin-2-amine; 8-Chloro-4-piperazin-1-y1][1]benzofuro[3,2-d]pyrimidin-2-amine; 8-Chloro-4-(1,4-diazepan-1-yl)[1]benzofuro[3,2-d]pyrimidin-2-amine; 8-Chloro-4-[(3aR,6aS)-hexahydropyrrolo[3,4-c]pyrrol-2(1H)-yl][1]benzofuro[3,2-d]pyrimidin-2-amine; 8-Chloro-[(3S)-3-methyl-1,4-diazepan-1-yl][1]benzofuro[3,2-d]pyrimidin-2-amine; (8-Chloro-N4-[2-(methylamino)ethyl][1]benzofuro[3I2-c0pyrimidine-2,4-diamine; 8-Chloro-N$^4$-pyrrolidin-3-yl[1]benzofuro[3,2-d]pyrimidine-2,4-diamine (7-Chloro-4-(4-methylpiperazin-1-yl)[1]benzofuro[3,2-d]pyrimidin-2-amine, formate salt; 2-Amino-4-(3-aminopyrrolidin-1-yl)[1]benzofuro[3,2-d]pyrimidin-8-ol; 4-(4-Methyl-piperazin-1-yl)-5H-indeno[1,2-d]pyrimidin-2-ylamine; 8-Chloro-4-(4-methyl-piperazin-1-yl)-5H-indeno[1,2-d]pyrimidin-2-ylamine; 8-Bromo-4-[(3S)-3-methylpiperazin-1-yl][1]benzofuro[3,2-d]pyrimidin-2-amine); 8-Bromo-4-piperazin-1-yl[1]benzofuro[3,2-d]pyrimidin-2-amine; 8-Bromo-4-(1,4-diazepan-1-yl)[1]benzofuro[3,2-d]pyrimidin-2-amine; Methyl-2-amino-4-[(3S)-3-methylpiperazin-1-yl][1]benzofuro[3,2-d]pyrimidine-8-carboxylate; Methyl-2-amino-4-(1,4-diazepan-1-yl)[1]benzofuro[3,2-d]pyrimidine-8-carboxylate; 2-Amino-4-[(3S)-3-methylpiperazin-1-yl][1]benzofuro[3,2-d]pyrimidine-8-carboxylic acid; 4-(4-Methylpiperazin-1-yl)[1]benzofuro[3,2-d]pyrimidin-2-amine; 8-Chloro-4-(4-methylpiperazin-1-yl)[1]benzofuro[3,2-d]pyrimidin-2-amine; 4-(4-Methylpiperazin-1-yl)-5H-indeno[1,2-d]pyrimidin-2-amine; 8-Chloro-4-[(3R)-3-methylpiperazin-1-yl][1]benzofuro[3,2-d]pyrimidin-2-amine; 4-(3-Aminopyrrolidin-1-yl)-7-chloro[1]benzofuro[3,2-d]pyrimidin-2-amine; 7-Chloro-4-piperazin-1-yl[1]benzofuro[3,2-d]pyrimidin-2-amine; 7-Chloro-4-(4-methylpiperazin-1-yl)[1]benzofuro[3,2-d]pyrimidin-2-amine, formic acid salt; 4-(4-Methylpiperazin-1-yl)pyrido[3',2':4,5]furo[3,2-d]pyrimidin-2-amine; 8-Chloro-4-[(3aR,6aS)-hexahydropyrrolo[3,4-c]pyrrol-2(1H)-yl][1]benzofuro[3,2-d]pyrimidin-2-amine; 8-Chloro-4-(4-methylpiperazin-1-yl)-5H-indeno[1,2-d]pyrimidin-2-amine; 8-Chloro-4-[(3S)-3-methyl-1,4-diazepan-1-yl][1]benzofuro[3,2-d]pyrimidin-2-amine; 4-(3-Aminopyrrolidin-1-yl)-8-methoxy[1]benzofuro[3,2-d]pyrimidin-2-amine; 8-Chloro-4-piperazin-1-yl[1]benzofuro[3,2-d]pyrimidin-2-amine; 2-Amino-4-(3-aminopyrrolidin-1-yl)[1]benzofuro[3,2-d]pyrimidin-8-ol; 8-Chloro-N$^4$-[2-(methylamino)ethyl][1]benzofuro[3,2-d]pyrimidine-2,4-diamine; 8-Chloro-4-(1,4-diazepan-1-yl)[1]benzofuro[3,2-d]pyrimidin-2-amine; 8-Methoxy-4-piperazin-1-yl[1]benzofuro[3,2-d]pyrimidin-2-amine, diacetate; 8-Chloro-4-[(3S)-3-methylpiperazin-1-yl][1]benzofuro[3,2-d]pyrimidin-2-amine; 8-Chloro-4-piperazin-1-yl[1]benzofuro[3,2-cy]pyrimidin-2-amine, dihydrochloride; 8-Bromo-4-[(3S)-3-methylpiperazin-1-yl][1]benzofuro[3,2-d]pyrimidin-2-amine; 8-Bromo-4-piperazin-1-yl[1]benzofuro[3,2-d]pyrimidin-2-amine; 8-Bromo-4-(1,4-diazepan-1-yl)[1]benzofuro[3,2-d]pyrimidin-2-amine.

In another embodiment, selective Histamine H4 antagonists are selected from those described in the international Patent Application WO2008/031556: 4-(4-methylpiperazin-1-yl)-6-piperidin-1-ylpyrimidin-2-amine; 4-(1,3-dihydro-2H-isoindol-2-yl)-6-(4-methylpiperazin-1-yl)pyrimidin-2-amine; 4-(4-methylpiperazin-1-yl)-6-(4-methylpiperazin-1-yl)pyrimidin-2-amine; 4-[4-(2-methoxyphenyl)piperidin-1-yl]-6-(4-methylpiperazin-1-yl)pyrimidin-2-amine; 4-(3,4-dihydroisoquinolin-2(1H)-yl)-6-(4-methylpiperazin-1-yl)

pyrimidin-2-amine; 4-(5-fluoro-1,3-dihydro-2H-isoindol-2-yl)-6-(4-methylpiperazin-1-yl)pyrimidin-2-amine; 4-(3-aminopyrrolidin-1-yl)-6-(1,3-dihydro-2H-isoindol-2-yl)pyrimidin-2-amine; 4-(4-methylpiperazin-1-yl)-6-(2-methylpyrrolidin-1-yl)pyrimidin-2-amine; 4-(2-ethylpiperidin-1-yl)-6-(4-methylpiperazin-1-yl)pyrimidin-2-amine; 4-[3-(2-methoxyphenyl)pyrrolidin-1-yl]-6-(4-methylpiperazin-1-yl)pyrimidin-2-amine; 4-[3-(4-chlorophenyl)pyrrolidin-1-yl]-6-(4-methylpiperazin-1-yl)pyrimidin-2-amine; 4-(2-methylpyrrolidin-1-yl)-6-piperazin-1-ylpyrimidin-2-amine; 4-(4-methylpiperazin-1-yl)-6-[(2R)-2-methylpyrrolidin-1-yl]pyrimidin-2-amine; 4-(4-methylpiperazin-1-yl)-6-[(2S)-2-methylpyrrolidin-1-yl]pyrimidin-2-amine; 4-(2,6-dimethylpiperidin-1-yl)-6-(4-methylpiperazin-1-yl)pyrimidin-2-amine; 4-(6-azabicyclo[3.2.1]oct-6-yl)-6-(4-methylpiperazin-1-yl)pyrimidin-2-amine; 4-azepan-1-yl-6-(4-methylpiperazin-1-yl)pyrimidin-2-amine; 1-[2-amino-6-(4-methylpiperazin-1-yl)pyrimidin-4-yl]-4-(4-chlorophenyl)piperidin-4-ol; 4-(4-methylpiperazin-1-yl)-6-(3-phenylpiperidin-1-yl)pyrimidin-2-amine; $N^4$-cyclohexyl-6-(hexahydropyrrolo[1,2-a]pyrazin-2m(1H)-yl)pyrimidine-2,4-diamine; $N^4$-adamantan-1-yl-6-(4-methylpiperazin-1-yl)pyrimidine-2,4-diamine; 6-(4-methylpiperazin-1-yl)-$N^4$-(1,3,3-trimethylbicyclo[2.2.1]hept-2-yl)pyrimidine-2,4-diamine; $N^4$-adamantan-2-yl-6-(4-methylpiperazin-1-yl)pyrimidine-2,4-diamine; 6-(4-methylpiperazin-1-yl)-$N^4$(1R;4R)(1,7,7-trimethylbicyclo[2.2.1]hept-2-yl)pyrimidine-2,4-diamine; $N^4$-cyclohexyl-$N^4$-methyl-6-(4-methylpiperazin-1-yl)pyrimidine-2,4-cliamine; 4-(7-azabicyclo[2.2.1]hept-7-yl)-6-(4-methylpiperazin-1-yl)pyrimidin-2-amine; 4-(3-aminopyrrolidin-1-yl)-6-(5-fluoro-1,3-dihydro-2H-isoindol-2-yl)pyrimidin-2-amine; 4-(hexahydropyrrolo[1,2-a]pyrazin-2(1H)-yl)-6-(2-methylpyrrolidin-1-yl)pyrimidin-2-amine; $N^4$-1-azabicyclo[2.2.2]oct-3-yl-6-(1,3-dihydro-2H-isoindol-2-yl)pyrimidine-2,4-diamine; 4-(3-methyl-3,4-dihydroisoquinolin-2(1H)-yl)-6-(4-methylpiperazin-1-yl)pyrimidin-2-amine; $N^4$-1-azabicyclo[2.2.2]oct-3-yl-6-(2-methylpyrrolidin-1-yl)pyrimidine-2,4-diamine; 6-(2-methylpyrrolidin-1-yl)-$N^4$-pyrrolidin-3-ylpyrimidine-2,4-diamine; 4-[4-(methylamino)piperidin-1-yl]-6-(2-methylpyrrolidin-1-yl)pyrimidin-2-amine; 4-(1,3-dihydro-2H-isoindol-2-yl)-6-[4-(methylamino)piperidin-1-yl]pyrimidin-2-amine; 4-(1,3-dihydro-2H-isoindol-2-yl)-6-(4-methyl-1,4-diazepan-1-yl)pyrimidin-2-amine; 6-[(3R)-3-aminopyrrolidin-1-yl]-$N^4$-cyclohexylpyrimidine-2,4-diamine triacetate salt; 4(R)-(3-methyl-3,4-dihydroisoquinolin-2(1H)-yl)-6-(4-methylpiperazin-1-yl)pyrimidin-2-amine 4(S)-(3-methyl-3,4-dihydroisoquinolin-2(1H)-yl)-6-(4-methylpiperazin-1-yl)pyrimidin-2-amine; $N^4$-cyclohexyl-$N^6$-[2-(dimethylamino)ethyl]pyrimidine-2,4,6-triamine; N4-cyclohexyl-6-[4-(methylamino)piperidin-1-yl]pyrimidine-2,4-diamine; 6-[(3S)-3-aminopyrrolidin-1-yl]-$N^4$-cyclohexylpyrimidine-2,4-diamine; $N^4$-cyclopentyl-6-(4-methylpiperazin-1-yl)pyrimidine-2,4-diamine; $N^4$-cyclopentyl-N4-methyl-6-(4-methylpiperazin-1-yl)pyrimidine-2,4-diamine; $N^4$-cycloheptyl-6-(4-methylpiperazin-1-yl)pyrimidine-2,4-diamine; 4-[(1R*, 5S*)-8-azabicyclo[3.2.1]oct-8-yl]-6-(4-methylpiperazin-1-yl)pyrimidin-2-amine; $N^4$-[(1R*,2S*,4S*)-bicyclo[2.2.1]hept-2-yl]-6-(4-methylpiperazin-1-yl)pyrimidine-2,4-diamine; $N^4$-bicyclo[2.2.1]hept-2-yl-6-(4-methylpiperazin-1-yl)pyrimidine-2,4-diamine; $N^4$-[(1R*,2S*,4S*)-bicyclo[2.2.1]hept-2-yl]-$N^6$-dimethylaminoJethyllpyrimidine-2,4-triamine; $N^4$-[(1R*,2S*,4S*)-bicyclo[2.2.1]hept-2-yl]-6-[(3aR*,6aS*)-hexahydropyrrolo[3,4-c]pyrrol-2(1H)-yl]pyrimidine-2,4-diamine; 4-cyclohexyl-6-(4-methylpiperazin-1-yl)pyrimidin-2-amine; 4-adamantan-2-yl-6-(4-methylpiperazin-1-yl)pyrimidin-2-amine; 4-Isopropyl-6-(4-methylpiperazin-1-yl)pyrimidin-2-amine; 4-(1-methylpentyl)-6-(4-methylpiperazin-1-yl)pyrimidin-2-amine; 4-cyclopentyl-6-(4-methylpiperazin-1-yl)pyrimidin-2-amine; 4-(1-ethylpropyl)-6-(4-methylpiperazin-1-yl)pyrimidin-2-amine; 4-cyclohexyl-6-(hexahydropyrrolo[1,2-a]pyrazin-2(1H)-yl)pyrimidin-2-amine; 4-cyclohexyl-6-(4-methyl-1,4-diazepan-1-yl)pyrimidin-2-amine; 4-cyclohexyl-6-(4-ethylpiperazin-1-yl)pyrimidin-2-amine; 4-cyclohexyl-6-[3-(dimethylamino)pyrrolidin-1-yl]pyrimidin-2-amine; 6-cyclohexyl-$N^4$-methyl-$N^4$-(1-methylpyrrolidin-3-yl)pyrimidine-2,4-diamine; 6-cyclohexyl-$N^4$-(1-methylpyrrolidin-4-yl)pyrimidine-2,4-diamine; 4(R)-(4-methylpiperazin-1-yl)-6-(1-phenylethyl)pyrimidin-2-amine; 4(S)-(4-methylpiperazin-1-yl)-6-(1-phenylethyl)pyrimidin-2-amine; 4-(3-aminopyrrolidin-1-yl)-6-cyclopropylpyrimidin-2-amine; 4-cyclopropyl-6-[3-(methylamino)pyrrolidin-1-yl]pyrimidin-2-amine; 4-(3-aminopyrrolidin-1-yl)-6-(4-methylcyclohex-1-en-1-yl)pyrimidin-2-amine di-trifluoroacetic acid salt ; 6-cyclohex-1-en-1-yl-$N^4$-[2-(dimethylamino)ethyl]pyrimidine-2,4-diamine; 4-tert-butyl-6-(4-methylpiperazin-1-yl)pyrimidin-2-amine acetate salt; 4-tert-butyl-6-[3-(methylamino)pyrrolidin-1-yl]pyrimidin-2-amine acetate salt; 4-[adamantan-2-yl]-6-[(3S)-3-aminopyrrolidin-1-yl]pyrimidin-2-amine; 4-[adamantan-2-yl]-6-[(3S)-3-(methylamino)pyrrolidin-1-yl]pyrimidin-2-amine; 4-cyclohept-1-en-1-yl-6-(4-methylpiperazin-1-yl)pyrimidin-2-amine; 4-cyclopentyl-6-(3-methylpiperazin-1-yl)pyrimidin-2-amine; 4-(3-aminoazetidin-1-yl)-6-cyclohex-1-en-1-ylpyrimidin-2-amine; 4-cyclohexyl-6-(3-methylpiperazin-1-yl)pyrimidin-2-amine; 4-(3-aminoazetidin-1-yl)-6-cyclohexylpyrimidin-2-amine; 4-(4-methylpiperazin-1-yl)-6-(1,2,3,4-tetrahydronaphthalen-2-yl)pyrimidin-2-amine; 4-[3-(methylamino)pyrrolidin-1-yl]-6-(1,2,3,4-tetrahydronaphthalen-2-yl)pyrimidin-2-amine; 4-(3-aminopyrrolidin-1-yl)-6-(1,2,3,4-tetrahydronaphthalen-2-yl)pyrimidin-2-amine; 4-cyclopentyl-6-[(3S)-3-methylpiperazin-1-yl]pyrimidin-2-amine; 4-cyclopentyl-6-[(3R)-3-methylpiperazin-1-yl]pyrimidin-2-amine; 4-cyclohexyl-6-[(2S)-2-methylpiperazin-1-yl]pyrimidin-2-amine; 4-[(3R)-3-aminopyrrolidin-1-yl]-6-[(1E)-3,3-dimethylbut-1-en-1-yl]pyrimidin-2-amine 4-[3-(aminomethyl)azetidin-1-yl]-6-cyclohexylpyrimidin-2-amine; 4-(3-aminoazetidin-1-yl)-6-cyclopentylpyrimidin-2-amine; 4-cyclopentyl-6-(3-ethylpiperazin-1-yl)pyrimidin-2-amine; 4-cyclopentyl-6-[(3S)-3-isopropylpiperazin-1-yl]pyrimidin-2-amine; 4-cyclopentyl-6-(3,8-diazabicyclo[3.2.1]oct-3-yl)pyrimidin-2-amine; $N^4$-(2,3-dihydro-1H-inden-2-yl)-6-[3-methylamino)pyrrolidin-1-yl]pyrimidine-2,4-diamine; 4-cyclopentyl-6-[(3S)-3-isobutylpiperazin-1-yl]pyrimidin-2-amine; 4-cyclopentyl-6-[3-(ethylamino)azetidin-1-yl]pyrimidin-2-amine; 6-(4-methylpiperazin-1-yl)-$N^4$-(tetrahydro-2H-pyran-4-yl)pyrimidine-2,4-diamine; 6-(4-methylpiperazin-1-yl)-$N^4$-(tetrahydro-2H-pyran-4-yl)pyrimidine-2,4-diamine acetate; $N^4$-cyclohexyl-6-(4-methylpiperazin-1-yl)pyrimidine-2,4-diamine; 4-(1,3-dihydro-2H-isoindol-2-yl)-6-piperazin-1-ylpyrimidin-2-amine; 4-(3-aminopyrrolidin-1-yl)-6-(2-methylpyrrolidin-1-yl)pyrimidin-2-amine; 4-[3-(methylamino)pyrrolidin-1-yl]-6-(2-methylpyrrolidin-1-yl)pyrimidin-2-amine; 6-(3-aminopyrrolidin-1-yl)-$N^4$-[(1R*,2S*,4S*)-bicyclo[2.2.1]hept-2-yl]pyrimidine-2,4-diamine; $N^4$-[(1R*,2S*,4S*)-bicyclo[2.2.1]hept-2-yl]-6-[3-(methylamino)pyrrolidin-1-yl]pyrimidine-2,4-diamine; 6-[(3S)-3-aminopyrrolidin-1-yl]-$N^4$-[(1R*,2S*,4S*)-bicyclo[2.2.1]hept-2-yl]pyrimidine-2,4-diamine; 6-[(3R)-3-aminopyrrolidin-1-yl]-$N^4$-[(1R*,2S*,4S*)-bicyclo[2.2.1]

hept-2-yl]pyrimidine-2,4-diamine; 6-[(3S)-3-aminopyrrolidin-1-yl]-N$^4$-[(1R*,2R*,4S*)-bicyclo[2.2.1]hept-2-yl]pyrimidirre-2,4-diamine; 6-[(3R)-3-aminopyrrolidin-1-yl]-N$^4$-[(1R*,2R*,4S*)-bicyclo[2.2.1]hept-2-yl]pyrimidine-2,4-diamine; N4-[exo-bicyclo[2.2.1]hept-2-yl]-6-[(3S)-3-(methylamino)pyrrolidin-1-yl]pyrimidine-2,4-diamine; N$^4$-[(1R*,2S*,4S*)-bicyclo[2.2.1]hept-2-yl]-6-[3R]-3-(methylamino)pyrrolidin-1-yl]pyrimidine-2,4-diamine; N$^4$-[(1R*,2S*,4S*)-bicyclo[2.2.1]hept-2-yl]-6-[(3S)-3-(methylamino)pyrrolidin-1-yl]pyrimidine-2,4-diamine; N$^4$-[(1R*,2S*,4S*)-bicyclo[2.2.1]hept-2-yl]-6-[(3R)-3-(methylamino)pyrrolidin-1-yl]pyrimidine-2,4-diamine; N$^4$-[(1R*,2S*,4S*)-bicyclo[2.2.1]hept-2-yl]-6-(3-methylpiperazin-1-y)pyrimidine-2,4-diamine; N$^4$-[(1R*,2R*,4S*)-bicyclo[2.2.1]hept-2-yl]-6-(1,4-diazepan-1-yl)pyrimidine-2,4-diamine; N$^4$-[(1R*,2R*,4S*)-bicyclo[2.2.1]hept-2-yl]-6-((4aR*,7aR*)-octahydro-6H-pyrrolo[3,4-b]pyridin-6-yl)pyrimidine-2,4-diamine; N$^4$-[(1R*,2R*,4S*)-bicyclo[2.2.1]hept-2-yl]-6-(hexahydropyrrolo[1,2-a]pyrazin-2(1H)-yl)pyrimidine-2,4-diamine; N$^4$-[(1R*,2R*,4S*)-bicyclo[2.2.1]hept-2-yl]-6-piperazin-1-yl-pyrimidine-2,4-diamine; 4-(3-aminopyrrolidin-1-yl)-6-cyclopentylpyrimidin-2-amine; 4-adamantan-2-yl-6-(3-aminopyrrolidin-1-yl)pyrimidin-2-amine; 4-cyclopentyl-6-[3-(methylamino)pyrrolidin-1-yl]pyrimidin-2-amine; 4-[(3S)-3-aminopyrrolidin-1-yl]-6-cyclohexylpyrimidin-2-amine; 4-[(3R)-3-aminopyrrolidin-1-yl]-6-cyclohexylpyrimidin-2-amine; 4-(3-aminopyrrolidin-1-yl)-6-(cyclohexylmethyl)pyrimidin-2-amine; 4-cyclopentyl-6-piperazin-1-ylpyrimidin-2-amine; 4-[adamantan-2-yl]-6-[(3R)-3-(methylamino)pyrrolidin-1-yl]pyrimidin-2-amine; 4-[adamantan-2-yl]-6-[(3R)-3-aminopyrrolidin-1-yl]pyrimidin-2-amine; 4-(cyclopentylmethyl)-6-(3-methylpiperazin-1-yl)pyrimidin-2-amine; 4-(3-aminopyrrolidin-1-yl)-6-(cyclopentylmethyl)pyrimidin-2-amine; 4-cyclohexyl-6-[3-(methylamino)azetidin-1-yl]pyrimidin-2-amine; 4-cyclopentyl-6-[(4aR*,7aR*)-octahydro-6H-pyrrolo[3,4-b]pyridin-6-yl]pyrimidin-2-amine; 4-cyclohexyl-6-(1,4-diazepan-1-yl)pyrimidin-2-amine; 4-cyclopentyl-6-(1,4-diazepan-1-yl)pyrimidin-2-amine; 6-cyclopentyl-N$^4$-[2-(methylamino)ethyl]pyrimidine-2,4-diamine; 4-[(3R)-3-aminopyrrolidin-1-yl]-6-cyclohex-1-en-1-ylpyrimidin-2-amine; N$^4$-cyclohexyl-6-(4-methylpiperazin-1-yl)pyrimidine-2,4-diamine; 4-(1,3-dihydro-2H-isoindol-2-yl)-6-piperazin-1-ylpyrimidin-2-amine; 4-(3-aminopyrrolidin-1-yl)-6-(2-methylpyrrolidin-1-yl)pyrimidin-2-amine; 4-[3-(methylamino)pyrrolidin-1-yl]-6-(2-methylpyrrolidin-1-yl)pyrimidin-2-amine; 6-(3-aminopyrrolidin-1-yl)-N$^4$-[(1R*,2S*,4S*)-bicyclo[2.2.1]hept-2-yl]pyrimidine-2,4-diamine; N4-[(1R*,2S*,4S*)-bicyclo[2.2.1]hept-2-yl]-6-[3-(methylamino)pyrrolidin-1-yl]pyrimidine-2,4-diamine; 6-[(3S)-3-aminopyrrolidin-1-yl]-N$^4$-[(1R*,2S*,4S*)-bicyclo[2.2.1]hept-2-yl]pyrimidine-2,4-diamine; 6-[(3R)-3-aminopyrrolidin-1-yl]-N$^4$-[(1R*,2S*,4S*)-bicyclo[2.2.1]hept-2-yl]pyrimidine-2,4-diamine; 6-[(3S)-3-aminopyrrolidin-1-yl]-N$^4$-[(1R*,2R*,4S*)-bicyclo[2.2.1]hept-2-yl]pyrimidine-2,4-diamine; 6-[(3R)-3-aminopyrrolidin-1-yl]-N$^4$-[(1R*,2R*,4S*)-bicyclo[2.2.1]hept-2-yl]pyrimidine-2,4-diamine; N$^4$-[exo-bicyclo[2.2.1]hept-2-yl]-6-[(3S)-3-(methylamino)pyrrolidin-1-yl]pyrimidine-2,4-diamine; N$^4$-[(1R*,2R*,4S*)-bicyclo[2.2.1]hept-2-yl]-6-[(3R)-3-(methylamino)pyrrolidin-1-yl]pyrimidine-2,4-diamine; N$^4$-[(1R*,2S*,4S*)-bicyclo[2.2.1]hept-2-yl]-6-[(3S)-3-(methylamino)pyrrolidin-1-yl]pyrimidine-2,4-diamine; N$^4$-[(1R,2S*,4S*)-bicyclo[2.2.1]hept-2-yl]-6-[(3R)-3-(methylamino)pyrrolidin-1-yl]pyrimidine-2,4-diamine; N$^4$-[(1R*,2R*,4S*)-bicyclo[2.2.1]hept-2-yl]-6-(3-methylpiperazin-1-yl)pyrimidine-2,4-diamine; N$^4$-[(1R*,2R*,4S*)-bicyclo[2.2.1]hept-2-yl]-6-(1,4-diazepan-1-yl)pyrimidine-2,4-diamine; N$^4$-[(1R*,2R*,4S*)-bicyclo[2.2.1]hept-2-yl]-6-[((4aR*,7aR*)-octahydro-6H-pyrrolo[3,4-b]pyridin-6-yl)pyrimidine-2,4-diamine; N$^4$-[(1R*,2R*,4S*)-bicyclo[2.2.1]hept-2-yl]-6-(hexahydropyrrolo[1,2-a]pyrazin-2(1H)-yl)pyrimidine-2,4-diamine; N$^4$-[(1R*,2R*,4S*)-bicyclo[2.2.1]hept-2-yl]-6-piperazin-1-ylpyrimidine-2,4-diamine; 4-(3-aminopyrrolidin-1-yl)-6-cyclopentylpyrimidin-2-amine; 4-adamantan-2-yl-6-(3-aminopyrrolidin-1-yl)pyrimidin-2-amine; 4-cyclopentyl-6-[3-(methylamino)pyrrolidin-1-yl]pyrimidin-2-amine; 4-[(3S)-3-aminopyrrolidin-1-yl]-6-cyclohexylpyrimidin-2-amine; 4-[(3R)-3-aminopyrrolidin-1-yl]-6-cyclohexylpyrimidin-2-amine; 4-(3-aminopyrrolidin-1-yl)-6-(cyclohexylmethyl)pyrimidin-2-amine; 4-cyclopentyl-6-piperazin-1-ylpyrimidin-2-amine; 4-[adamantan-2-yl]-6-[(3R)-3-(methylamino)pyrrolidin-1-yl]pyrimidin-2-amine; 4-[adamantan-2-yl]-6-[(3R)-3-aminopyrrolidin-1-yl]pyrimidin-2-amine; 4-(cyclopentylmethyl)-6-(3-methylpiperazin-1-yl)pyrimidin-2-amine; 4-(3-aminopyrrolidin-1-yl)-6-(cyclopentylmethyl)pyrimidin-2-amine; 4-cyclohexyl-6-[3-(methylamino)azetidin-1-yl]pyrimidin-2-amine; 4-cyclopentyl-6-[(4aR*,7aR*)-octahydro-6H-pyrrolo[3,4-b]pyridin-6-yl]pyrimidin-2-amine; 4-cyclohexyl-6-(1,4-diazepan-1-yl)pyrimidin-2-amine; 4-cyclopentyl-6-(1,4-diazepan-1-yl)pyrimidin-2-amine; 6-cyclopentyl-N$^4$-(methylamino)ethyl]pyrimidine-2,4-diamine; 4-[(3R)-3-aminopyrrolidin-1-yl]-6-cyclohex-1-en-1-ylpyrimidin-2-amine.

In another embodiment, selective Histamine H4 antagonists are selected from those described in the international Patent Application WO2008122378: 6-cyclohex-1-en-1-yl-4-[3-(methylamino)pyrrolidin-1-yl]pyridin-2-amine; 6-(4-chlorophenyl)-4-(4-methylpiperazin-1-yl)pyridin-2-amine; 6-(4-methylcyclohex-1-en-1-yl)-4-(4-methylpiperazin-1-yl)pyridin-2-amine; 6-adamantan-2-yl-4-(4-methylpiperazin-1-yl)pyridin-2-amine; 4-(3-aminopyrrolidin-1-yl)-6-cyclohex-1-en-1-ylpyridin-2-amine; 6-(3-methylphenyl)-4-(4-methylpiperazin-1-yl)pyridin-2-amine; 4-[(3R)-3-aminopyrrolidin-1-yl]-6-(4-chlorophenyl)pyridin-2-amine; 4-(4-methylpiperazin-1-yl)-6-(4-methylpiperidin-1-yl)pyridin-2-amine; N-cycloheptyl-4-(4-methylpiperazin-1-yl)pyridine-2,6-diamine; 4-[3-(methylamino)pyrrolidin-1-yl]-6-(2-methylpyrrolidin-1-yl)pyridin-2-amine; 4-(4-methylpiperazin-1-yl)-6-(2-methylpyrrolidin-1-yl)pyridin-2-amine; 4-[3-(methylamino)pyrrolidin-1-yl]-6-(4-methylpiperidin-1-yl)pyridin-2-amine; 4-[(3-methylamino)pyrrolidin-1-yl]-6-(4-trifluoromethylphenyl)pyridin-2-amine; 4-[(3-methylamino)pyrrolidin-1-yl]-6-(4-trifluoromethoxyphenyl)pyridin-2-amine; 6-(4-chlorophenyl)-4-[(3-methylamino)pyrrolidin-1-yl]pyridin-2-amine; 4-[(3-methylamino)pyrrolidin-1-yl]-6-(3-methylphenyl)pyridin-2-amine; N-cycloheptyl-4-(4-methylpiperazin-1-yl)pyridine-2,6-diamine; 4-[3-(methylamino)pyrrolidin-1-yl]-6-(2-methylpyrrolidin-1-yl)pyridin-2-amine; 4-[(3-methylamino)pyrrolidin-1-yl]-6-(3-methylphenyl)pyridin-2-amine; 6-cyclohex-1-en-1-yl-4-[3-(methylamino)pyrrolidin-1-yl]pyridin-2-amine; 6-(4-chlorophenyl)-4-[(3-methylamino)pyrrolidin-1-yl]pyridin-2-amine.

In another embodiment, selective Histamine H4 antagonists are selected from those described in the international Patent Application WO2009047255: 4-(4-methylpiperazin-1-yl)-7-phenyl-5,6,7,8-tetrahydroquinazolin-2-amine; 4-(3-aminoazetidin-1-yl)-7-phenyl-5,6,7,8-tetrahydroquinazolin-2-amine; 4-(3-aminopyrrolidin-1-yl)-7-phenyl-5,6,7,8- tetrahydroquinazolin-2-amine; 4-[(4aR*,7aR*)-octahydro-6H-pyrrolo[3,4-b]pyridin-6-yl]-7-phenyl-5,6,7,8-tetrahydroquinazolin-2-amine; 4-(3-methylpiperazin-1-yl)-7-phenyl-5,6,7,8-tetrahydroquinazolin-2-amine; 7-(3-chlorophenyl)-4-(4-methylpiperazin-1-yl)-5,6,7,8-tetrahydroquinazolin-2-amine; 7-(3-chlorophenyl)-4-(1,4-diazepan-1-yl)-5,6,7,8-tetrahydroquinazolin-2-amine; 7-(3-chlorophenyl)-4-[(4aR*,7aR*)-octahydro-6H-pyrrolo[3,4-b]pyridin-6-yl]-5,6,7,8-tetrahydroquinazolin-2-amine; 7,7-dimethyl-4-(4-methylpiperazin-1-yl)-5,6,7,8-tetrahydroquinazolin-2-amine; 4-(1,4-diazepan-1-yl)-7,7-dimethyl-5,6,7,8-tetrahydroquinazolin-2-amine; 4-(3-aminopyrrolidin-1-yl)-7,7-dimethyl-5,6,7,8-tetrahydroquinazolin-2-amine; 7,7-dimethyl-4-[(4aR*,7aR*)-octahydro-6H-pyrrolo[3,4-b]pyridin-6-yl]-5,6,7,8-tetrahydroquinazolin-2-amine; 4-(3-aminopyrrolidin-1-yl)-7-(3-chlorophenyl)-5,6,7,8-tetrahydroquinazolin-2-amine; 7,7-dimethyl-4-(3-methylpiperazin-1-yl)-5,6,7,8-tetrahydroquinazolin-2-amine; 7,7-dimethyl-4-piperazin-1-yl-5,6,7,8-tetrahydroquinazolin-2-amine; 7-(2-chlorophenyl)-4-(4-methylpiperazin-1-yl)-5,6,7,8-tetrahydroquinazolin-2-amine; 7-(2-chlorophenyl)-4-(1,4-diazepan-1-yl)-5,6,7,8-tetrahydroquinazolin-2-amine; 4-(3-aminopyrrolidin-1-yl)-7-(2-chlorophenyl)-5,6,7,8-tetrahydroquinazolin-2-amine; 4-(1,4-diazepan-1-yl)-7-(4-fluorophenyl)-5,6,7,8-tetrahydroquinazolin-2-amine; 7-(4-fluorophenyl)-4-(4-methylpiperazin-1-yl)-5,6,7,8-tetrahydroquinazolin-2-amine; 4-piperazin-1-yl-7-pyridin-2-yl-5,6,7,8-tetrahydroquinazolin-2-amine; 4-(4-methylpiperazin-1-yl)-7-pyridin-2-yl-5,6,7,8-tetrahydroquinazolin-2-amine; 4-(1,4-diazepan-1-yl)-7-pyridin-2-yl-5,6,7,8-tetrahydroquinazolin-2-amine; 7-(5-chloro-2-thienyl)-4-piperazin-1-yl-5,6,7,8-tetrahydroquinazolin-2-amine; 5-(5-chloro-2-thienyl)-4-piperazin-1-yl-5,6,7,8-tetrahydroquinazolin-2-amine; 5-(5-chloro-2-thienyl)-4-(4-methylpiperazin-1-yl)-5,6,7,8-tetrahydroquinazolin-2-amine; 7-(5-chloro-2-thienyl)-4-(4-methylpiperazin-1-yl)-5,6,7,8-tetrahydroquinazolin-2-amine; 5-(5-chloro-2-thienyl)-4-(1,4-diazepan-1-yl)-5,6,7,8-tetrahydroquinazolin-2-amine; 7-(5-chloro-2-thienyl)-4-(1,4-diazepan-1-yl)-5,6,7,8-tetrahydroquinazolin-2-amine; 7-(4-fluorophenyl)-4-[(4aR*,7aR*)-octahydro-6H-pyrrolo[3,4-b]pyridin-6-yl]-5,6,7,8-tetrahydroquinazolin-2-amine trifluoroacetic acid salt; 7-(4-fluorophenyl)-N-4-[2-(methylamino)ethyl]-5,6,7,8-tetrahydroquinazoline-2,4-diamine; 7,7-dimethyl-N-4-[2-(methylamino)ethyl]-5,6,7,8-tetrahydroquinazoline-2,4-diamine; 4-(hexahydropyrrolo[3,4-c]pyrrol-2(1H)-yl)-7,7-dimethyl-5,6,7,8-tetrahydroquinazolin-2-amine; 7,7-dimethyl-4-[(3S)-3-methyl-1,4-diazepan-1-yl]-5,6,7,8-tetrahydroquinazolin-2-amine; 8,8-dimethyl-4-(3-methylpiperazin-1-yl)-5,6,7,8-tetrahydroquinazolin-2-amine; 4-(3-aminoazetidin-1-yl)-8,8-dimethyl-5,6,7,8-tetrahydroquinazolin-2-amine; 8,8-dimethyl-N-4-piperidin-4-yl-5,6,7,8-tetrahydroquinazoline-2,4-diamine; 8,8-dimethyl-N-4-pyrrolidin-3-yl-5,6,7,8-tetrahydroquinazoline-2,4-diamine; 8,8-dimethyl-4-[(3S)-3-methylpiperazin-1-yl]-5,6,7,8-tetrahydroquinazolin-2-amine; 6,6-dimethyl-4-(4-methylpiperazin-1-yl)-6,7-dihydro-5H-cyclopenta[d]pyrimidin-2-amine; 4-(4-methylpiperazin-1-yl)-7-[4-(trifluoromethyl)pyrimidin-2-yl]-5,6,7,8-tetrahydropyrido[3,4-d]pyrimidin-2-amine; 7,7-dimethyl-4-(4-methylpiperazin-1-yl)-5,6,7,8-tetrahydroquinazolin-2-amine; 4-(1,4-diazepan-1-yl)-7,7-dimethyl-5,6,7,8-tetrahydroquinazolin-2-amine; 4-(3-aminopyrrolidin-1-yl)-7,7-dimethyl-5,6,7,8-tetrahydroquinazolin-2-amine; 7,7-dimethyl-4-[(4aR*,7aR*)-octahydro-6H-pyrrolo[3,4-b]pyridin-6-yl]-5,6,7,8-tetrahydroquinazolin-2-amine; 7,7-dimethyl-4-(3-methylpiperazin-1-yl)-5,6,7,8-tetrahydroquinazolin-2-amine; 7,7-dimethyl-4-piperazin-1-yl-5,6,7,8-tetrahydroquinazolin-2-amine; 7-(5-chloro-2-thienyl)-4-piperazin-1-yl-5,6,7,8-tetrahydroquinazolin-2-amine; 7-(5-chloro-2-thienyl)-4-(1,4-diazepan-1-yl)-5,6,7,8-tetrahydroquinazolin-2-amine; 4-(3-aminoazetidin-1-yl)-7,7-dimethyl-5,6,7,8-tetrahydroquinazolin-2-amine; 7-isobutyl-4-piperazin-1-yl-5,6,7,8-tetrahydroquinazolin-2-amine; 8,8-dimethyl-4-(4-methylpiperazin-1-yl)-5,6,7,8-tetrahydroquinazolin-2-amine; 4-(1,4-diazepan-1-yl)-8,8-dimethyl-5,6,7,8-tetrahydroquinazolin-2-amine bis acetic acid salt; 7,7-dimethyl-4-[methylamino)pyrrolidin-1-yl]-5,6,7,8-tetrahydroquinazolin-2-amine; 7,7-dimethyl-4-[(3S)-3-methylpiperazin-1-yl]-5,6,7,8-tetrahydroquinazolin-2-amine; 4-(1,4-diazepan-1-yl)-7-isobutyl-5,6,7,8-tetrahydroquinazolin-2-amine acetic acid salt; 7-isobutyl-4-(4-methylpiperazin-1-yl)-5,6,7,8-tetrahydroquinazolin-2-amine acetic acid salt; 7,7-dimethyl-4-[methylamino)azetidin-1-yl]-5,6,7,8-tetrahydroquinazolin-2-amine; 8,8-dimethyl-4-[(4aR*,7aR*)-octahydro-6H-pyrrolo[3,4-b]pyridin-6-yl]-5,6,7,8-tetrahydroquinazolin-2-amine; 4'-(4-methyl piperazin-1-yl)-5',8'-dihydro-6'H-spiro[cyclohexane-1,7'-quinazolin]-2'-amine; 4'-[(4aR*,7aR*)-octahydro-6H-pyrrolo[3,4-b]pyridin-6-yl]-5',8'-dihydro-6'H-spiro[cyclohexane-1,7'-quinazolin]-2'-amine; 4'-[(3S)-3-methylpiperazin-1-yl]-5',8'-dihydro-6'H-spiro[cyclohexane-1,7'-quinazolin]-2'-amine bis acetic acid salt; 4'-(1,4-diazepan-1-yl)-5',8'-dihydro-6'H-spiro[cyclohexane-1,7'-quinazolin]-2'-amine bis acetic acid salt; 4'-piperazin-1-yl-5',8'-dihydro-6'H-spiro[cyclohexane-1,7'-quinazolin]-2'-amine bis acetic acid salt; 4'-[3-(methylamino)azetidin-1-yl]-5',8'-dihydro-6'H-spiro[cyclohexane-1,7'-quinazolin]-2'-amine bis acetate salt; 4-(3-aminopyrrolidin-1-yl)-7-isobutyl-5,6,7,8-tetrahydroquinazolin-2-amine bis acetate salt; 7-isopropyl-4-(4-methylpiperazin-1-yl)-5,6,7,8-tetrahydroquinazolin-2-amine; 7-isopropyl-4-[(3S)-3-methylpiperazin-1-yl]-5,6,7,8-tetrahydroquinazolin-2-amine bis acetic acid salt; 7-isopropyl-4-[(4aR*,7aR*)-octahydro-6H-pyrrolo[3,4-b]pyridin-6-yl]-5,6,7,8-tetrahydroquinazolin-2-amine; 7-isopropyl-4-[methylamino)azetidin-1-yl]-5,6,7,8-tetrahydroquinazolin-2-amine; tert-butyl-4-(2-amino-7,7-dimethyl-5,6,7,8-tetrahydroquinazolin-4-yl)-1,4-diazepane-1-carboxylate.

In another embodiment, selective Histamine H4 antagonists are selected from those described in the international Patent Application WO2008/003702 : 4-amino-6-chloro-2-(4-methylpiperazinyl)-quinazoline, 2-(4-methylpiperazinyl)-4-phenoxyquinazoline, 4-(benzyloxy)-2-(4-methylpiperazinyl)-quinazoline, 2-(4-methylpiperazinyl)-quinoline, 2-(4-methylpiperazinyl)-quinoxaline, 6-chloro-2-(4-methylpiperazinyl)-quinoline, 6-chloro-2-(4-methylpiperazinyl)-quinoxaline, 2-(4-methylpiperazinyl)-quinazoline, 3-(4-methylpiperazinyl)-isoquinoline, 1-(4-methylpiperazinyl)-isoquinoline, 3-benzyl-2-(4-methylpiperazinyl)-quinoxaline, 6,7-dichloro-2-methoxy-3-(4-methylpiperazinyl)-quinoxaline and 7-chloro-2-methoxy-3-(4-methylpiperazinyl)-quinoxaline.

In another embodiment, selective Histamine H4 antagonists are selected from those described in the international Patent Application WO2006/050965: 8-chloro-2-methyl-4-(4-methylpiperazin-1-yl)benzo[4,5]furo[3,2-d]pyrimidine; 8-chloro-4-(4-methylpiperazin-1-yl)benzo[4,5]furo[3,2-d]pyrimidine; 4-(4-methylpiperazin-1-yl)benzo[4,5]furo[3,2-d]pyrimidine; 6-chloro-1-(4-methylpiperazin-1-yl)-9H-2,4,9-triazafluorene; 4-(Piperazin-1-yl)benzo[4,5]furo[3,2-d]pyrimidine; 4-(piperazin-1-yl)benzo[4,5]thieno[3,2-d]pyrimidine; 8-Chloro-4-(1,4-diazepan-1-yl)benzo[4,5]

thieno[3,2-d]pyrimidine; 8-Chloro-2-cyclopropyl-4-(4-methylpiperazin-1-yl)benzo[4,5]furo[3,2-d]pyrimidine; 8-Chloro-4-(4-methylpiperazin-1-yl)-2-trifluoromethyl-benzo[4,5]furo[3,2-d]pyrimidine; 8-Chloro-4-(1-methylpiperidin-4-yl)benzo[4,5]furo[3,2-d]pyrimidine; 8-Chloro-4-[(1S,4S)-2,5-diazabicyclo[2.2.1]hept-2-yl]benzo[4,5]furo[3,2-d]pyrimidine; 8-Chloro-4-(3-methylpiperazin-1-yl)benzo[4,5]furo[3,2-d]pyrimidine; 8-Chloro-4-[(1S,4S)-5-methyl-2,5-diazabicyclo[2.2.1]hept-2-yl]benzo[4,5]furo[3,2-d]pyrimidine; 8-Chloro-4-(3,4-dimethylpiperazin-1-yl)benzo[4,5]furo[3,2-d]pyrimidine; 8-Cloro-4-(1-metylpyrrolidin-3-yl)benzo[4,5]furo[3,2-d]pyrimidine; 8-Chloro-4-(8-methyl-3,8-diazabicyclo[3.2.1]oct-3-yl)benzo[4,5]furo[3,2-d]pyrimidine; 8-Chloro-4-[(1R,4R)-5-methyl-2,5-diazabicyclo[2.2.1]hept-2-yl]benzo[4,5]furo[3,2-d]pyrimidine; 8-Chloro-4-[5-methyl-2,5-diazabicyclo[2.2.2]oct-2-yl]benzo[4,5]furo[3,2-d]pyrimidine; and 8-Chloro-4-[5-methyl-2,5-diazabicyclo[3.2.1]oct-2-yl]benzo[4,5]furo[3,2-d]pyrimidine.

In another embodiment, selective Histamine H4 antagonists are selected from those described in the international Patent Application WO2005/014579: 4-(1H-Imidazol-4-ylmethoxy)-1-(1-oxo-3-phenylbutyl)-piperidine; 4-(1H-Imidazol-4-ylmethoxy)-1-[[4-(trifluoromethyl)phenyl]acetyl]-piperidine; 1-[2-(4-Hydroxyphenyl)-1-oxopropyl]-4-[(5-methyl-1H-imidazol-4-yl)methoxy]-piperidine; 1-[(4-fluorophenyl)acetyl]-4-(1H-imidazol-4-ylmethoxy)-piperidine; 1-[(2-chlorophenyl)acetyl]-4-(1H-imidazol-4-ylmethoxy)-piperidine; 1-[(4-chlorophenyl)acetyl]-4-(1H-imidazol-4-ylmethoxy)-piperidine; 4-(H-imidazol-4-ylmethoxy)-1-(phenylacetyl)-piperidine; 1-(4-cyclohexylbenzoyl)-4-(1H-imidazol-4-ylmethoxy)-piperidine; 1-[(3,4-dichlorophenyl) acetyl]-4-(H-imidazol-4-ylmethoxy)-piperidine; 4-(1H-imidazol-4-ylmethoxy)-1-[(4-methylphenyl)acetyl]-piperidine; 1-[(3,4-difluorophenyl)acetyl]-4-(1H-imidazol-4-ylmethoxy)-piperidine; 1-[(2,4-difluorophenyl)acetyl]-4-(1H-imidazol-4-ylmethoxy)-piperidine; 4-(1H-imidazol-4-ylmethoxy)-1-[(4'-propyl[1,1'-biphenyl]-4-yl)carbonyl]-piperine; 1-[2-(4-hydroxyphenyl)-1-oxopropyl]-4-(1H-imidazol-4-ylmethoxy)-piperidine; 1-[(2E)-3-(3,4-dichlorophenyl)-1-oxo-2-propenyl]-4-(1H-imidazol-4-ylmethoxy)-piperidine; 1-[3-(2,4-dichlorophenyl)-1-oxopropyl]-4-(1H-imidazol-4-ylmethoxy)-piperidine; 1-[(2,4-dichlorophenyl)acetyl]-4-(1H-imidazol-4-ylmethoxy)-piperidine; 1-[(2-Bromophenyl)methyl]-4-(1H-imidazol-4-ylmethoxy)-piperidine; 1-[(3-Bromo-2-thienyl)methyl]-4-[(5-methyl-1H-imidazol-4-yl)methoxy]-piperidine; 1-[(3-bromo-2-thienyl)methyl]-4-(1H-imidazol-4-ylmethoxy)-piperidine; 1-[(4-ethynylphenyl)methyl]-4-(1H-imidazol-4-ylmethoxy)-piperidine; 4-(1H-imidazol-4-ylmethoxy)-1-[[3-(4-methylphenoxy)phenyl]methyl]-piperidine; 4-(1H-imidazol-4-ylmethoxy)-1-[[4-(2-propenyloxy)phenyl]methyl]-piperidine; 4-[[4-(1H-imidazol-4-ylmethoxy)-1-piperidinyl]methyl]-phenol; 4-(1H-imidazol-4-ylmethoxy)-1-[(2-methoxyphenyl)methyl]-piperidine; 4-(1H-imidazol-4-ylmethoxy)-1-[[3-(4-methoxyphenoxy)phenyl]methyl]-piperidine; 1-[(2,3-dichlorophenyl)methyl]-4-(1H-imidazol-4-ylmethoxy)-piperidine; 1-[(2-chloro-4-fluorophenyl)methyl]-4-(1H-imidazol-4-ylmethoxy)-piperidine; 1-(2-dibenzofuranylmethyl)-4-(1H-imidazol-4-ylmethoxy)-piperidine; 4-(1H-imidazol-4-ylmethoxy)-1-[[2-(methylthio)phenyl]methyl]-piperidine; 4-(1H-imidazol-4-ylmethoxy)-1-(thieno [2,3-b] [I] benzothien-2-ylmethyl)-piperidine; 1-[(2-chloro-5-nitrophenyl)methyl]-4-(1H-imidazol-4-ylmethoxy)-piperidine; 1H-pyrrole,2-[[4-(1H-imidazol-4-ylmethoxy)-1-piperidinyl]methyl]-1-[(4-methylphenyl)sulfonyl]-; 2-ethoxy-6-[[4-(1H-imidazol-4-ylmethoxy)-1-piperidinyl]methyl]-phenol; 1-(1,3-benzoidoxol-5-ylmethyl)-4-(1H-imidazol-4-ylmethoxy)-piperidine; 4-(1H-imidazol-4-ylmethoxy)-1-[[4-(phenylmethoxy)phenyl]methyl]-piperidine; 1-[[2-fluoro-4-(trifluoromethyl)phenyl] methyl]-4-(1H-imidazol-4-ylmethoxy)-piperidine; 1-[(4-bromophenyl)methyl]-4-(1H-imidazol-4-ylmethoxy)-piperidine; 4-(1H-imidazol-4-ylmethoxy)-1-[(4-methylphenyl)methyl]-piperidine; 4-(H-imidazol-4-ylmethoxy)-1-(2-thienylmethyl)-piperidine; 1-[(4-chlorophenyl)methyl]-4-(1H-imidazol-4-ylmethoxy)-piperidine; 1-[(2-chloro-6-fluorophenyl)methyl]-4-(1H-imidazol-4-ylmethoxy)-piperidine; 4-(1H-imidazol-4-ylmethoxy)-1-[(3-methyl-2-thienyl)methyl]-piperidine; 4-(1H-imidazol-4-ylmethoxy)-1-(2-naphthalenylmethyl)-piperidine; 4-(1H-imidazol-4-ylmethoxy)-1-(1-naphthalenylmethyl)-piperidine; 4-(1H-imidazol-4-ylmethoxy)-1-[(2-nitrophenyl) methyl]-piperidine; 4-(1H-imidazol-4-ylmethoxy)-1-(3-thienylmethyl)-piperidine; 1-([1,1'-biphenyl]-4-ylmethyl)-4-(1H-imidazol-4-ylmethoxy)-piperidine; 1-[(2,5-difluorophenyl)methyl]-4-(1H-imidazol-4-ylmethoxy)-piperidine; 4-(1H-imidazol-4-ylmethoxy)-1-[(3-phenoxyphenyl)methyl]-piperidine; 4-(1H-imidazol-4-ylmethoxy)-1-[(3-methylphenyl)methyl]-piperidine; 1-(2-furanylmethyl)-4-(1H-imidazol-4-ylmethoxy)-piperidine; 1-[(2,6-dichlorophenyl) methyl]-4-(1H-imidazol-4-ylmethoxy)-piperidine; 1-[(4-fluorophenyl)methyl]-4-(1H-imidazol-4-ylmethoxy)-piperidine; 1-[(3-fluorophenyl) methyl]-4-(1H-imidazol-4-ylmethoxy)-piperidine; 1-(3-furanylmethyl)-4-(1H-imidazol-4-ylmethoxy)-piperidine; 1-[(4-ethylphenyl)methyl]-4-(1H-imidazol-4-ylmethoxy)-piperidine; 4-(1H-imidazol-4-ylmethoxy)-1-[(2-methylphenyl)methyl]-piperidine; 1-[(3-chlorophenyl)methyl]-4-(1H-imidazol-4-ylmethoxy)-piperidine; 4-(1H-imidazol-4-ylmethoxy)-1-[(5-methyl-2-thienyl)methyl]-piperidine; 1-[(4-bromo-2-thienyl)methyl]-4-(1H-imidazol-4-ylmethoxy)-piperidine; 1-([2,2'-bithiophen]-5-ylmethyl)-(1H-imidazol-4-ylmethoxy)-piperidine; 3,5-dichloro-2-[[4-(1H-imidazol-4-ylmethoxy)-1-piperidinyl]methyl]-phenol; 1-[(3,4-difluorophenyl)methyl]-4-(1H-imidazol-4-ylmethoxy)-piperidine; 1-[(3,5-difluorophenyl)methyl]-4-(1H-imidazol-4-ylmethoxy)-piperidine; 1-[(6-chloro-1,3-benzodioxol-5-yl)methyl]-4-(1H-imidazol-4-ylmethoxy)-piperidine; 1-[[4-[4-(1,1-dimethylethyl)-2-thiazolyl]phenyl] methyl]-4-(1H-imidazol-4-ylmethoxy)-piperidine; 4-(1H-imidazol-4-ylmethoxy)-1-[(1-methyl-1H-pyrrol-2-yl) methyl]-piperidine; 1H-indole,3-[[4-(1H-imidazol-4-ylmethoxy)-1-piperidinyl]methyl]-1-(phenylmethyl)-; 1-[(5-chloro-2-thienyl)methyl]-4-(1H-imidazol-4-ylmethoxy)-piperidine; 1-(1,3-benzodioxol-4-ylmethyl)-4-(1H-imidazol-4-ylmethoxy)-piperidine; 2-thiophenecarbonitrile, 3-[[4-(1H-imidazol-4-ylmethoxy)-1-piperidinyl]methyl]phenoxy] methyl]-piperidine; 4-(1H-imidazol-4-ylmethoxy)-1-[[5-(phenylethynyl)-2-thienyl]methyl]-piperidine; 4-(1H-imidazol-4-ylmethoxy)-1-[[5-(4-nitrophenyl)-2-furanyl] methyl]-piperidine; 4-(1H-imidazol-4-ylmethoxy)-1-[[5-(3-nitrophenyl)-2-furanyl]methyl]-piperidine; 1-[(4-chloro-1H-pyrazol-3-yl) methyl]-4-(1H-imidazol-4-ylmethoxy)-piperidine; 1-[(4-bromo-1-methyl-1H-pyrazol-3-yl) methyl]-4-(1H-imidazol-4-ylmethoxy)-piperidine; 1-[(4-bromo-1H-pyrazol-3-yl)methyl]-4-(1H-imidazol-4-ylmethoxy)-piperidine; 2-[[4-(1H-imidazol-4-ylmethoxy)-1-piperidinyl]methyl]-benzonitrile; 4-(1H-imidazol-4-ylmethoxy)-1-[(4-iodophenyl)methyl]-piperidine; 1-[(5-ethyl-2-thienyl)methyl]-4-(1H-imidazol-4-ylmethoxy)-piperidine; 4-(1H-imidazol-4-ylmethoxy)-1-[[5-(methylthio)-2-thienyl]methyl]-piperidine; 1-[[1-(3,5- dichlorophenyl)-1H-pyrrol-2-yl]methyl]-4-(1H-imidazol-4-ylmethoxy)-piperidine; 1-[[1-(4-chlorophenyl)-IH-pyrrol-2-yl]methyl]-4-(1H-imidazol-4-ylmethoxy)-piperidine; 4-(1H-imidazol-4-ylmethoxy)-1-[[4-(phenylethynyl)-2-thienyl]methyl]-piperidine; 4-(1H-imidazol-4-ylmethoxy)-1-[(3-phenoxy-2-thienyl)methyl]-piperidine; 1-[[2-chloro-5-(trifluoromethyl)phenyl]methyl]-4-(1H-imidazol-4-ylmethoxy)-piperidine; 4-(1H-imidazol-4-ylmethoxy)-1-[(4-propoxyphenyl)methyl]-piperidine; 2-[[4-(1H-imidazol-4-ylmethoxy)-1-piperidinyl]methyl]-phenol; 1-[(2,4-difluorophenyl) methyl]-4-(1H-imidazol-4-ylmethoxy)-piperidine; 3-[[4-(1H-imidazol-4-ylmethoxy)-1-piperidinyl]methyl]-2-thiophenecarbonitrile; 1-(benzolb] thien-3-ylmethyl)-4-(IH-imidazol-4-ylmethoxy)-piperidine; 2-chloro-3-[[4-(1H-imidazol-4-ylmethoxy)-1-piperidinyl]methyl]-pyridine; 3-[[4-(1H-imidazol-4-ylmethoxy)-1-piperidinyl]methyl]-2-(2-propenyl)-phenol ; 1-[(4-chloro-3-fluorophenyl) methyl]-4-(1H-imidazol-4-ylmethoxy)-piperidine; 4-(1H-imidazol-4-ylmethoxy)-1-[[4-(trifluoromethoxy)phenyl]methyl]-piperidine; 1-[(2,6-difluorophenyl)methyl]-4-(1H-imidazol-4-ylmethoxy)-piperidine; 1-[(4-bromo-2-fluorophenyl) methyl]-4-(1H-imidazol-4-ylmethoxy)-piperidine; 1-[(2,2-difluoro-1,3-benzodioxol-5-yl)methyl]-4-(1H-imidazol-4-ylmethoxy)-piperidine; 1-[(4-butoxyphenyl)methyl]-4-(1H-imidazol-4-ylmethoxy)-piperidine; 4-(1H-imidazol-4-ylmethoxy)-1-[(2,3,5-trichlorophenyl) methyl]-piperidine; 1-[(2,5-dichlorophenyl)methyl]-4-(1H-imidazol-4-ylmethoxy)-piperidine; 4-(H-imidazol-4-ylmethoxy)-1-[[2-(trifluoromethyl)phenyl)methyl]-piperidine, or 1-[(4-chloro-2-nitrophenyl)methyl]-4-(1H-imidazol-4-ylmethoxy)-piperidine or pharmaceutically acceptable salts or solvates thereof.

In another embodiment, selective Histamine H4 antagonists are selected from those described in the international Patent Application WO2009107767.

In a particular embodiment, the Histamine H4 receptor antagonist is 1-[(5-chloro-1H-benzimidazol-2-yl)carbonyl]-4-methylpiperazine (also named JNJ 10191584 or VUF 6002) described by Herman D. et al. (2005). This selective antagonist binds with high affinity the human Histamine H4 receptor (Ki =26 nM). This affinity is 540-fold more selective over the H3 receptor (Ki =14.1 µM) (Zhang M. et al. 2007).

In a particular embodiment, the selective Histamine H4 receptor antagonist is 1-[(5-chloro-1H-indol-2-yl)carbonyl]-4-methylpiperazine (also named JNJ 7777120) described by Robin L. et al. (2004).

In a particular embodiment, the selective Histamine H4 receptor antagonist is 4-((3R)-3-Aminopyrrolidin-1-yl)-6,7-dihydro-5H-benzo[6,7]cyclohepta[1,2-d]pyrimidin-2-ylamine (also named A-943931) described by Cowart M D. et al. (2008).

In a particular embodiment, the selective Histamine H4 receptor antagonist is cis-4-(Piperazin-1-yl)-5,6,7a,8,9,10,11,11a-octahydrobenzofuro[2,3-h]quinazolin-2-amine (also named A-987306) described by Liu H et al. (2008).

In another embodiment the selective Histamine H4 receptor antagonist may consist in an antibody (the term including antibody fragment) that can block Histamine H4 receptor activation.

In particular, the selective Histamine H4 receptor antagonist may consist in an antibody directed against the Histamine H4 receptor or a ligand of the Histamine H4 receptor, in such a way that said antibody impairs the binding of a H4 ligand to said receptor.

Antibodies directed against the Histamine H4 receptor can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against Histamine H4 receptor or ligands of Histamine H4 receptors can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-H4, or anti-H4 ligands single chain antibodies. Histamine H4 receptor antagonists useful in practicing the present invention also include anti-H4, or anti-H4 ligands antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to Histamine H4 receptor.

Humanized anti-Histamine H4 receptor or anti-H4 ligands antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the Histamine H4 receptor as above described, the skilled man in the art can easily select those blocking Histamine H4 receptor activation.

In another embodiment the selective Histamine H4 receptor antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against the Histamine H4 receptor as above described, the skilled man in the art can easily select those blocking Histamine H4 receptor activation.

Another aspect of the invention relates to the use of an inhibitor of Histamine H4 receptor gene expression.

Histamine receptor (H1, H2, H3 or H4) sequences showing low sequence identity, the inhibitors of Histamine H4 receptor gene expression which may be used according to the invention advantageously provides selective inhibition of Histamine H4 receptor gene expression, by comparison with the other histamine receptors (H1, H2, or H3) expression.

Inhibitors of Histamine H4 receptor gene expression for use in the present invention may be based on anti-sense oligonucleotide constructs. Anti-sense oligonucleotides, including anti-sense RNA molecules and anti-sense DNA molecules, would act to directly block the translation of Histamine H4 receptor mRNA by binding thereto and thus preventing protein translation or increasing mRNA degradation, thus decreasing the level of Histamine H4 receptors, and thus activity, in a cell. For example, antisense oligonucleotides of at least about 15 bases and complementary to unique regions of the mRNA transcript sequence encoding Histamine H4 receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of Histamine H4 receptor gene expression for use in the present invention. Histamine H4 receptor gene expression can be reduced by contacting a subject or cell with a small double stranded RNA (dsRNA), or a vector or construct causing the production of a small double stranded RNA, such that Histamine H4 receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO01/36646, WO99/32619, and WO 01/68836).

Ribozymes can also function as inhibitors of Histamine H4 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Histamine H4 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of Histamine H4 receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing Histamine H4 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUCI9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another object of the invention relates to a method for treating and/or preventing vestibular disorders comprising administering a subject in need thereof with a selective Histamine H4 receptor antagonist or an inhibitor of Histamine H4 receptor gene expression.

Selective Histamine H4 receptor antagonists or inhibitors of Histamine H4 receptor gene expression may be administered in the form of a pharmaceutical composition, as defined below.

Preferably, said antagonists or inhibitors are administered in a therapeutically effective amount.

By a "therapeutically effective amount" is meant a sufficient amount of the selective Histamine H4 receptor antagonist or inhibitor of Histamine H4 receptor gene expression to treat and/or to prevent vestibular disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Inhibitors of the invention can be further identified by screening methods described in the state of the art. The screening methods of the invention can be carried out according to known methods.

The screening method may measure the binding of a candidate compound to the receptor, or to cells or membranes bearing the receptor, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist or agonist). Further, screening methods may test whether the candidate compound results in a signal generated by an antagonist of the receptor, using detection systems appropriate to cells bearing the receptor. Antagonists can be assayed in the presence of a known agonist (e.g. Histamine) and an effect on activation by the agonist by the presence of the candidate compound is observed. Competitive binding using known agonist such as histamine is also suitable.

The antagonistic activity of the candidate compounds towards the Histamine H4 receptor may be for example determined using various models. For example, methods that are described in Thurmond R L et al. (2004) or Venable J D. et al. (2005) may be used.

Pharmaceutical Compositions

The selective Histamine H4 receptor antagonists or inhibitors of Histamine H4 receptor gene expression may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The selective Histamine H4 receptor antagonists or inhibitors of Histamine H4 receptor gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The selective Histamine H4 receptor antagonists or inhibitors of Histamine H4 receptor gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular embodiment, the selective Histamine H4 receptor antagonists or inhibitors of Histamine H4 receptor gene expression are administered directly in the inner ear through the tympanic membrane. This administration mode may be preferred for introducing a direct and long term effect on the vestibule. Accordingly in a preferred embodiment, the selective Histamine H4 receptor antagonists or inhibitors of Histamine H4 receptor gene expression are administered in a gel formulation to allow a long term release of said antagonists or inhibitors in the inner ear.

The invention will further be illustrated in view of the following figures and examples.

FIGURES

FIG. 1. Effect of VUF 6002 on the depolarization-induced firing volley. (A) Representative traces obtained in an individual neuron after an application of 100 μM VUF 6002 (A), 10 μm (B) and 1 μM (C). The inhibitory responses were reversed during rinse with control medium. Inserts show individual volley before (a), during (b) and after (c) the application of VUF 6002.

Figure 2:
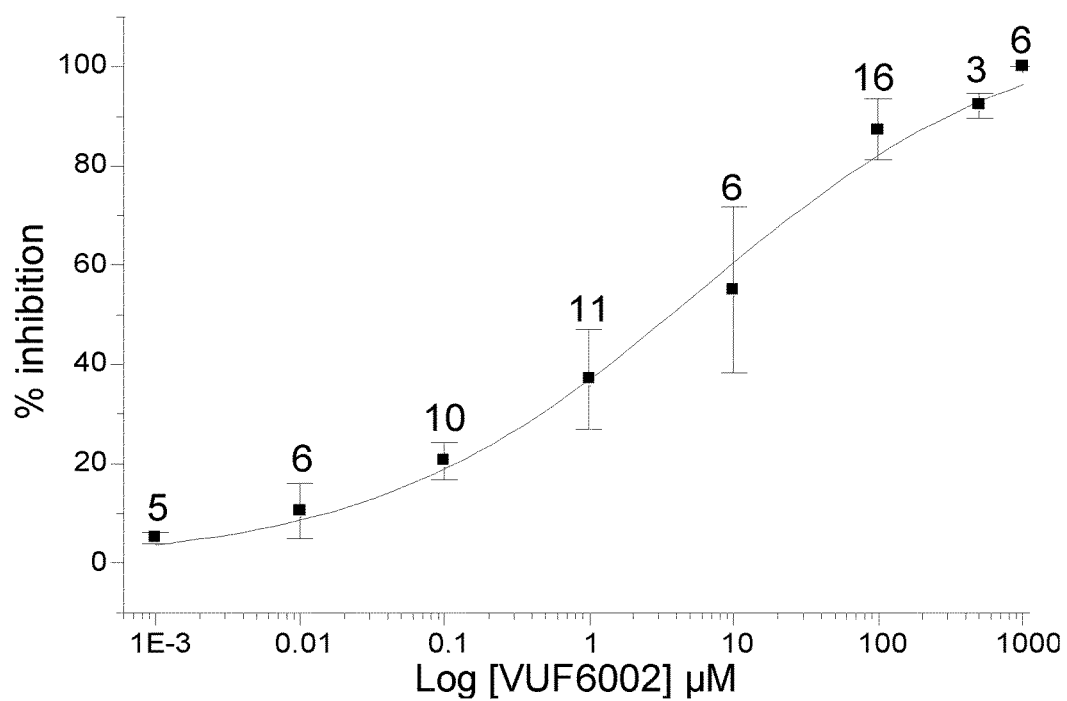

FIG. 2. Dose-dependent effect of VUF 6002 on the firing volley induced by standard depolarization. Curve fitting with one-term Hill equation (black line) gives an IC50 of 5.8 μM. Data are the mean percentage inhibition of control responses. Number of experiments are indicated above error bars.

Figure 3:
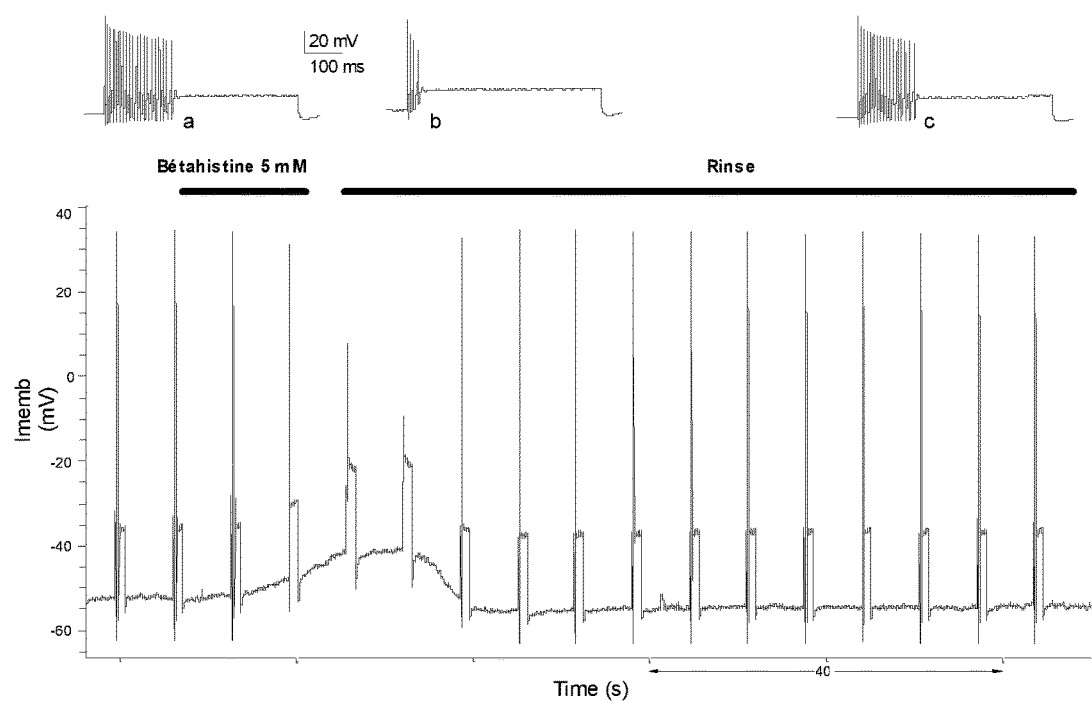

FIG. 3. Effect of betahistine on the depolarization-induced firing volley. Representative traces obtained in an individual neuron after an application of 5 mM betahistine. Inserts show individual volley before (a), during (b) and after (c) the application of betahistine. Note the strong depolarization of about 15 mV induced by betahistine. These responses were rapidly reversed during rinse with control medium.

Figure 4:
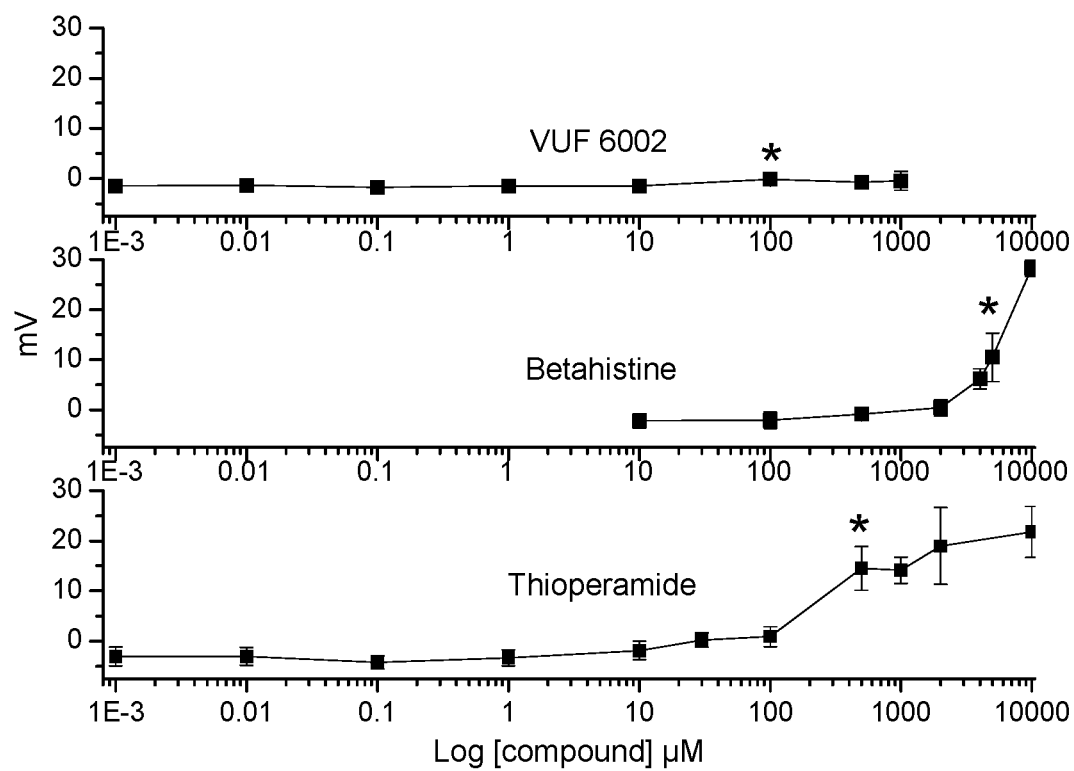

FIG. 4. Effect of VUF 6002, betahistidine and thioperamide on the variation of membrane potentials. Although VUF 6002 did not induce membrane variations, the two other compounds generated strong depolarisations at high concentrations. Stars indicate concentrations inducing 90% inhibition of the firing.

EXAMPLE

Methods:

Drugs/Chemicals: The 1-[(5-Chloro-1H-benzimidazol-2-yl) carbonyl]-4-methyl piperazine maleate (JNJ 10191584 maleate or VUF 6002) was purchase from Tocris Bioscience (Bristol, UK), and the 1-[(5-chloro-1H-indol-2-yl) carbonyl]-4-methyl piperazine maleate (JNJ 7777120) was obtained from Sigma (Sigma-Aldrich, St-Quentin Fallavier, France). Stock solutions were prepared at 50 mM in 100% dimethyl sulfoxide as recommended by the suppliers. Stock solutions of betahistine dihydrochloride (purchased from Sigma-Aldrich, St-Quentin Fallavier, France) and N-cyclohexyl-4-(1H-imidazol-4-yl)-1-piperidinecarbothioamide maleate (thioperamide, Sigma-Aldrich) were prepared in recording medium at respectively 1 M and 0.01 M. Drugs were then diluted in working solution before use.

Cell culture: Vestibular ganglion neurons were explanted aseptically from 2 to 6 days-old Wistar rats (Centre d'Elevage Janvier, Le Genest-Saint-Isle, France). All procedures were carried out in accordance to the French/European Communities Council Directive 86/609/EEC. The brainstem was hemi-sectioned and the eighth nerve was followed up to the level of the otocyst and cut just rostral to it.

The vestibular ganglia were excised, placed in Leibovitz medium (L15, Invitrogen, Cergy Pontoise, France), and dissociated by enzymatically (collagenase 0.75 mg/ml, dispase 1 mg/ml and dnase 0.75 mg/ml, 15 min at 25° C.). Enzymes were washed with Tyrode solution without $Ca^{2+}$ and $Mg^{2+}$, and the ganglion neurons were gently dissociated in culture medium with a pipette. The neurons were plated onto culture dishes previously coated with 5 μg/ml poly-L-ornithine, 10 μg/ml laminin and subsequently filled with 0.5 ml of a 1:1 mixture of Dulbecco's modified eagle medium and Ham's F-12 medium (Invitrogen) supplemented with 2% $N_2$ nutrient glucose (5 g/l), glutamine (1.5 mM), sodium bicarbonate (1.1 g/l), HEPES buffer (15 mM, pH 7.4), AraC 2 μM, brain-derived neurotrophic factor 10 μg/ml and 1% penicillin/streptomycin. The low density cultures were then maintained at 37° C. in 5% $CO_2$ for 7 to 8 days prior patch-clamp experiments.

Patch-clamp recordings: Whole-cell (current-clamp configuration) recording of responses were obtained using an Axopatch 200B amplifier (Axon Instruments; Molecular Devices Corp., Sunnyvale, Calif., USA). The extracellular solution contained (in mM): NaCl 135, HEPES 10, glucose 10, $MgCl_2$ 1, KCl 5, and $CaCl_2$ 4, pH 7.35 (with NaOH). Recording pipettes (2-3 MΩ) were drawn from microhematocrit tubes (Modulohm I/S Herlev, Denmark) and filled with the following solution (in mM): KCl 135, HEPES 10, glucose 10, NaCl5, EGTA 5, Mg-ATP3, GTP-Na 1, pH 7.35 (with KOH). The osmolarity of all solutions was set to 300 $mOsm/l^{-1}$. Experimental parameters and data acquisition were controlled with a PC computer and a Tecmar Labmaster analogue interface (Axon instruments, CA). Voltage transients were recorded from neurons presenting resting potentials lying between –45 and –65 mV. Trains of action potentials (APs) were elicited using 1 s, 200 pA depolarizing pulses applied every 6.5 s. Current signals were filtered at 10 KHz, digitized and stored using pCLAMP software (v 10.2, Axon instruments).

Drug application : The control and test solutions were applied using a multiple capillary perfusion system (flow rate 500 μl/min). After each application of the tested drug, the cells were washed with control buffer.

Data analysis and statistical methods : The results are expressed as means±S.E.M. The number of sample size (n) given is the number of neurons tested. Variations of the membrane potential and the number of APs were analysed using pCLAMP software (v10.2, Axon instruments). Drug concentration-effect relationships were fitted with a Hill equation of the form $I(x)=A*xn/(IC_{50}n+xn)$.

Results :

Immunochemical studies conducted by Western-blot and imunohistochemistry, using antibodies binding Histamine H4 receptor, revealed respectively the presence of Histamine H4 receptor protein in the primary vestibular ganglion and identified its cellular location to the membrane of neurones (data not shown).

Under phase contrast microscopy, cultured vestibular ganglion neurons had refringent soma with diameters ranging between 10 and 25 μm. All recorded neurons had long neuritic processes.

Recorded neurons displayed a resting potential of –50.3±3.6 mV (n=116, range–45 to –65 mV). Upon application of depolarizing pulses (1 s, 200 pA) two types of APs discharging volley were recorded. Phasic discharges constituted of 1 to 4 AP, while tonic discharges exhibited 10 to 80 APs (mean 29.3±14.3, n=92), (FIG. 1A-C a). Unless inhibitors application, these discharging patterns could be stable up to 30 minutes.

When the discharge pattern was phasic, application of 1 mM VUF 6002 completely abolished the firing (n=6). In neurons exhibiting tonic responses, application of VUF 6002 reduced the number of elicited APs in dose-dependant way. FIG. 1 illustrates the inhibitions of the discharge. At 100 μM the inhibition was 91% (FIG. 1A), while the compound induced only a slight membrane hyperpolarization (about –3 mV) (FIG. 4).

Application of 10 μm, 1 μM and 100 nM of VUF 6002 inhibited the firing by 55% (n=6), 37% (n=11) and 20% (n=10) respectively. These inhibitory effects were totally reversed by subsequent perfusion of control medium demonstrating the reversibility of the response (FIG. 1B-C). Action potentials intrinsic properties, such as spike amplitude, time to peak, rise and decay time constants, appeared to be not affected by VUF 6002.

The effect of another H4 receptor antagonist, the JNJ 7777120, was also studied. JNJ 7777120 was less efficient at low concentration (3% inhibition at 100 nM, n=7) than VUF 6002 while at higher concentrations the differences were not significant (p>0.05) (29% at 1 µM, n=7; 41% at 10 µM, n=9). Moreover, the 7777120 did not induce membrane depolarisation, even for high concentration application (1 mM).

The dose-response inhibition relationship of VUF 6002 was constructed with concentrations between 1 nM and 1 mM (FIG. 2). In our recording conditions, maximum inhibition occurred around 100 µM (90% inhibition) and the dose-response relationship had an $IC_{50}$ of 5.8 µM.

Dose-response inhibition relationship calculated for the JNJ 7777120 between 0.1 µM and 1000 µM gave an $IC_{50}$ of 10 µM.

The two selective H4 receptor antagonists VUF 6002 and JNJ 7777120 exhibit quite similar effects on both the firing and variation in membrane potentials.

By comparison, responses were established for applications of BH, an antagonist of the Histamine H3 receptor (Arrang et al, 1985). BH inhibited the discharge volley in the same way. Maximum inhibition of the discharge volley, elicited during standard depolarization stimulation, by BH was around 10 mM. During 2 mM application the membrane potential was not affected, but treatment by BH at 5 mM induced a strong depolarization of the neurons (14.3±4.7 mV, n=16) (FIG. 3, FIG. 4). The firing inhibition and depolarisation were rapidly abolished by subsequent perfusion of control medium indicating the reversibility of the response (FIG. 3). The dose-response relationship presented an $IC_{50}$ of 2.2 mM.

Thioperamide, a histamine antagonist of both H3 and H4 receptors (Gbahou et al. 2005) was tested on cultured vestibular neurons. At low concentration (0.01 to 10 µM), thioperamide inhibited the discharge volley without depolarizing the neurons (10% at 0.1 µM and 24% at 10 µM, n=9 and 13 respectively). Conversely, higher concentrations blocked the activity (87% at 500 µM, n=10) followed by strong membrane depolarisations of the neurons (FIG. 4). The firing inhibition by thioperamide applications was only slightly reversible during rinse, especially for high concentrations. The dose-response relationship presented an $IC_{50}$ of 100 µM.

Thioperamide exhibits effects lying between those of VUF 6002 and BH.

Present results are the first demonstration that selective Histamine H4 receptor antagonists are potent inhibitors of the mammal vestibular primary neurons firing.

Selective Histamine H4 receptor antagonists inhibit reversibly and on a dose-dependant manner the firing of vestibular neurons without inducing membrane depolarisations.

Betahistine (H3 antagonist) and thioperamide (H3 and H4 antagonist, ie non-selective Histamine H4 receptor antagonist) inhibit the firing on vestibular neurons, but their use request high concentration to get comparable responses as those of the selective Histamine H4 receptor antagonists. At these high concentrations, betahistine and thioperamide induce pronounced depolarisation of the neurons. Moreover, the application of thioperamide is only slightly reversible.

Selective Histamine H4 receptor antagonists are more efficient than classical antivertiginous prescribed drugs. The pharmacological properties of selective Histamine H4 receptor antagonists designs it as a powerful vestibuloplegic drug that could bring a therapeutic gain in the treatment of vestibular disorders.

Accordingly, selective inhibitors of Histamine H4 receptor gene expression and/or activity may be useful for the treatment of vestibular disorders.

REFERENCES

Throughout this application, various references describe the state of the art to which this invention pertains. The disclosures of these references are hereby incorporated by reference into the present disclosure.

Arrang J M, et al. (1985) Actions of betahistine at histamine receptors in the brain Eur J Pharmacol. 111:73-84.

Botta L, et al (1998) Effects of betahistine on vestibular receptors of the frog. Acta Otolaryngology 118:519-523.

Brummelkamp T R, et al. A system for stable expression of short interfering RNAs in mammalian cells. Science. 2002 Apr. 19; 296(5567):550-3.

Carter P, et al. Improved oligonucleotide site-directed mutagenesis using M13 vectors. Nucleic Acids Res. 1985 Jun. 25; 13(12):4431-43.

Chavez H, et al. (2005) Histamine (H3) receptors modulate the excitatory amino acid receptor response of the vestibular afferents. Brain Res. 1064:1-9

Cheng Y, et al. Relationship between the inhibition constant (Ki) and the concentration of inhibitor which causes 50 per cent inhibition (I50) of an enzymatic reaction, Biochem Pharmacol. 1973 Dec. 1; 22(23):3099-108.

Colas P, et al. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cote R J, et al. Generation of human monoclonal antibodies reactive with cellular antigens. Proc Natl Acad Sci USA. 1983 Apr.; 80(7):2026-30.

Cowart M D, et al. Rotationally constrained 2,4-diamino-5,6-disubstituted pyrimidines: a new class of Histamine H4 receptor antagonists with improved druglikeness and in vivo efficacy in pain and inflammation models. J Med Chem. 2008 Oct. 23; 51(20):6547-57. Epub 2008 Sep. 26.

Elbashir S M, et al. Duplexes of 21-nucleotide RNAs mediate RNA interference in cultured mammalian cells. Nature. 2001 May 24; 411(6836):494-8.

Gbahou F, et al. (2006) Compared pharmacology of human histamine H3 and H4 receptors: structure-activity relationships of histamine derivatives. Br J Pharmacol. 147: 744-54.

Hannon G J. RNA interference. Nature. 2002 Jul. 11; 418(6894):244-51.

Herman D. et al. Leurs Evaluation of Histamine H1 -, H2-, and H3-Receptor Ligands at the Human Histamine H4 Receptor: Identification of 4-Methylhistamine as the First Potent and Selective H4 Receptor Agonist Journal of Pharmacology And Experimental Therapeutics Housley G D, et al. (1988) Histamine and related substances influence neurotransmission in the semicircular canal. Hear Res. 35:87-97.

Jablonowski J A, et al. The first potent and selective non-imidazole human Histamine H4 receptor antagonists. J Med Chem. 2003 Sep. 11; 46(19):3957-60.

Jayasena S. D. (1999) Aptamers: an emerging class of molecules that rival antibodies in diagnostics. Clin Chem. 45(9):1628-50.

Kohler G, Milstein C. Continuous cultures of fused cells secreting antibody of predefined specificity. Nature. 1975 Aug. 7; 256(5517):495-7.

Kriegler, A Laboratory Manual," W. H. Freeman C.O., New York, 1990.

Lacour M, Sterkers O. (2001) Histamine and betahistine in the treatment of vertigo: elucidation of mechanisms of action. CNS Drugs;15:853-70

Liu C et al. (2001a) Cloning and pharmacological characterisation of a four histamine receptor (H4) expressed in bone marrow. Mol Pharmacol. 59:420-426.

Liu C et al (2001b) Comparison of human, mouse, rat and guinea pig histamine H4 receptors reveals substantial pharmacological species variation J Pharmacol Exp Ther 299:121-130

Liu H, et al. cis-4-(Piperazin-1-yl)-5,6,7a,8,9,10,11,11a-octahydrobenzofuro[2,3-h]quinazolin-2-amine (A-987306), A New Histamine Histamine H4 antagonist that Blocks Pain Responses against Carrageenan-Induced Hyperalgesia. J Med Chem. 2008 Nov. 5.

Lovenberg T W et al. (1999) Cloning and functional expression of the human histamine H3 receptor. Mol Pharmacol 55:1101-1107.

McManus M T, Sharp P A. Gene silencing in mammals by small interfering RNAs. Nat Rev Genet. 2002 October; 3(10):737-47.

Murry, "Methods in Molecular Biology," vol. 7, Humana Press, Inc., Cliffton, N.J., 1991.

Robin L. Thurmond, et al. A Potent and Selective Histamine H4 Receptor Antagonist with Anti-Inflammatory Properties Journal of Pharmacology And Experimental Therapeutics, JPET 309:404-413, 2004

Sambrook et al., "Molecular Cloning: A Laboratory Manual," Second Edition, Cold Spring Harbor Laboratory Press, 1989.

Soto E, et al. (2001) Betahistine produces post-synaptic inhibition of the excitability of the primary afferent neurons in the vestibular ndorgans. Acta Otolaryngology 545: 19-24.

Thurmond R L, et al. A potent and selective Histamine H4 receptor antagonist with anti-inflammatory properties. J Pharmacol Exp Ther. 2004 April; 309(1):404-13. Epub 2004 Jan. 13.

Tighilet B, et al. (2005) Dose- and duration-dependent effects of betahistine dihydrochloride treatment on histamine turnover in the cat. Eur J Pharmacol. 523: 54-63.

Tomoda K, et al. (1997) Effetc of betahistine on intracellular Ca concentration in guinea pig isolated vestibular hair cells. Acta Otolaryngology 528: 37-40.

Tuerk C. and Gold L. (1990) Systematic evolution of ligands by exponential enrichment: RNA ligands to bacteriophage T4 DNA polymerase. Science. 3;249(4968):505-10.

Tuschl T, et al.Targeted mRNA degradation by double-stranded RNA in vitro. Genes Dev. 1999 Dec. 15; 13(24): 3191-7.

Van Cauwenberge P B, De Moor S E. (1997) Physiopathology of H3-receptors and pharmacology of betahistine. Acta Otolaryngol Suppl. 526:43-6.

Venable J D, et al. Preparation and biological evaluation of indole, benzimidazole, and thienopyrrole piperazine carboxamides: potent human histamine h(4) antagonists. Med Chem. 2005 Dec. 29; 48(26):8289-98.

Wells J A, et al. Cassette mutagenesis: an efficient method for generation of multiple mutations at defined sites. Gene. 1985; 34(2-3):315-23.

Zhang M, et al. (2007) The histamine H(4) receptor: a novel modulator of inflammatory and immune disorders. Pharmacol Ther. 113:594-606.

Zoller M J, Smith M. Oligonucleotide-directed mutagenesis using M13-derived vectors: an efficient and general procedure for the production of point mutations in any fragment of DNA. Nucleic Acids Res. 1982 Oct. 25; 10(20):6487-500

The invention claimed is:

1. A method for treating a vestibular disorder in a subject in need thereof, comprising administering a selective Histamine H4 receptor antagonist to the subject, whereby treatment of the vestibular disorder, alleviates the progress of said vestibular disorder or of at least one symptom of said vestibular disorder, wherein the Histamine H4 receptor antagonist is selected from the group consisting of 2-isobutyl-6-(3-(methylamino)azetidin-1-yl)pyrimidin-4-amine and derivatives thereof, and wherein derivatives of 2-isobutyl-6-(3-(methylamino)azetidin-1-yl)pyrimidin-4-amine are selected from the group consisting of 2-(4-fluorobenzyl)-6-(3-(methylamino)azetidin-1-yl)pyrimidin-4-amine, 2-cyclopropyl-6-(3-(methylamino)azetidin-1-yl)pyrimidin-4-amine, 2-tert-butyl-6-(3-(methylamino)azetidin-1-yl)pyrimidin-4-amine, 2-isopropyl-6-(3-(methylamino)azetidin-1-yl)pyrimidin-4-amine, 2-(cyclopropylmethyl)-6-(3-(methylamino)azetidin-1-yl)pyrimidin-4-amine, 6-(3-(methylamino)azetidin-1-yl)-2-(phenoxymethyl)pyrimidin-4-amine, 6-(3-aminoazetidin-1-yl)-2-isobutylpyrimidin-4-amine, 2-isobutyl-6-(3-methyl-3-(methylamino)azetidin-1-yl)pyrimidin-4-amine, 2-cyclobutyl-6-(3-(methylamino)azetidin-1-yl)pyrimidin-4-amine, 2-cyclopentyl-6-(3-(methylamino)azetidin-1-yl)pyrimidin-4-amine, 2-(2,2-dimethylpropyl)-6-(3-(methylamino)azetidin-1-yl)pyrimidin-4-amine, 2-cyclohexylmethyl-6-(3-(methylamino)azetidin-1-yl)pyrimidin-4-amine and 2-cyclohexyl-6-(3-(methylamino)azetidin-1-yl)pyrimidin-4-amine.

2. The method according to claim 1, wherein said vestibular disorder is selected from the group consisting of vestibular neuritis, spell of Ménière's disease, endolymphatic hydrops, barotraumatism with vestibular disorders, vestibular syndromes after autoimmune inner ear disease, vestibular syndromes after chirurgical treatments of middle ear, chronic Menière, Ménière's disease, vestibular schwannomas and vestibular ataxia.

3. The method according to claim 1, wherein said selective H4 receptor antagonist is systemically administered.

4. The method according to claim 1, wherein said at least one symptom is selected from the group comprising vertigo, dizziness, imbalance and nausea.

5. The method according to claim 1, wherein said vestibular disorder is spell of Ménière's disease or chronic Ménière's disease.

* * * * *